(12) United States Patent
Hummel

(10) Patent No.: US 12,084,668 B2
(45) Date of Patent: Sep. 10, 2024

(54) HYBRID NUCLEIC ACID SEQUENCES FOR GENOME ENGINEERING

(71) Applicant: KWS SAAT SE & CO. KGAA, Einbeck (DE)

(72) Inventor: Aaron Hummel, Hillsborough, NC (US)

(73) Assignee: KWS SAAT SE & CO., KGAA, Einbeck (DE)

( * ) Notice: Subject to any disclaimer, the term of this patent is extended or adjusted under 35 U.S.C. 154(b) by 0 days.

(21) Appl. No.: 16/306,341

(22) PCT Filed: May 30, 2017

(86) PCT No.: PCT/EP2017/063067
§ 371 (c)(1),
(2) Date: Nov. 30, 2018

(87) PCT Pub. No.: WO2017/207589
PCT Pub. Date: Dec. 7, 2017

(65) Prior Publication Data
US 2019/0161760 A1    May 30, 2019

Related U.S. Application Data

(60) Provisional application No. 62/344,109, filed on Jun. 1, 2016.

(51) Int. Cl.
C12N 15/82    (2006.01)
C12N 15/113    (2010.01)

(52) U.S. Cl.
CPC ........ *C12N 15/8213* (2013.01); *C12N 15/113* (2013.01); *C12N 2310/20* (2017.05)

(58) Field of Classification Search
None
See application file for complete search history.

(56) References Cited

U.S. PATENT DOCUMENTS

| | | | |
|---|---|---|---|
| 8,932,814 B2 * | 1/2015 | Cong ................ | C12N 15/8509 435/6.1 |
| 9,580,701 B2 | 2/2017 | May et al. | |
| 2012/0042411 A1 | 2/2012 | Malcuit et al. | |
| 2015/0082478 A1 * | 3/2015 | Cigan ................ | C12N 15/8216 800/270 |
| 2015/0376645 A1 | 12/2015 | Zechiedrich et al. | |
| 2016/0060637 A1 | 3/2016 | Hommelsheim et al. | |
| 2016/0251675 A1 * | 9/2016 | Henry ..................... | A01H 5/10 800/267 |
| 2016/0298078 A1 | 10/2016 | Guay et al. | |
| 2017/0058298 A1 * | 3/2017 | Kennedy .................. | C12N 9/22 |
| 2017/0152507 A1 * | 6/2017 | Yin ........................ | C12N 15/102 |

FOREIGN PATENT DOCUMENTS

| | | |
|---|---|---|
| EP | 3 009 511 A2 | 4/2016 |
| WO | 2014/130955 A1 | 8/2014 |
| WO | 2014/150624 A1 | 9/2014 |
| WO | 2014/199358 A1 | 12/2014 |
| WO | 2015/006290 A1 | 1/2015 |
| WO | 2015/013583 | 1/2015 |
| WO | 2015/131101 A1 | 9/2015 |
| WO | 2015/191693 | 12/2015 |
| WO | 2016/021973 A1 | 2/2016 |
| WO | 2016/054326 A1 | 4/2016 |
| WO | 2016/065364 A1 | 4/2016 |
| WO | 2016/142719 A1 | 9/2016 |
| WO | 2017/040511 A1 | 3/2017 |
| WO | 2017/064546 A1 | 4/2017 |
| WO | 2017/070598 A1 | 4/2017 |
| WO | 2017/180711 A1 | 10/2017 |
| WO | 2017/186550 A1 | 11/2017 |

OTHER PUBLICATIONS

Paix et al 2015 Genetics 201:47-54 (Year: 2015).*
Zetsche et al 2015 Cell 163:759-771 (provided by Applicant) (Year: 2015).*
M.L. Schwartz et al., "SapTrap, a Toolkit for High-Throughput CRISPR/Cas9 Gene Modification in Caenorhabditis elegans", GENETICS, vol. 202, No. 4, Apr. 2016, pp. 1277-1288; Feb. 2, 2016, XP55381031, US ISSN: 0016-6731, DOI: 10.1534/genetics.115. 184275 figures S1, S2.
International Search Report and Written Opinion dated Aug. 23, 2017.
Office Action issued in Korean Patent Application No. 2018-7038125 dated Sep. 29, 2020.
Zetsche et al., "Cpf1 is a single RNA-Guides Endonuclease of Class 2 CRISPR-Cas System", Cell, vol. 163, No. 3, 2015, pp. 759-771.
Makarova et al., "An updated evolutionary classification of CRISPR-Cas systems", Nature Rev. Microbiol., 2015, vol. 13, No. 11, pp. 722-736.

(Continued)

*Primary Examiner* — Brent T Page
(74) *Attorney, Agent, or Firm* — Troutman Pepper Hamilton Sanders LLP

(57) ABSTRACT

The present invention relates to hybrid nucleic acid sequence constructs comprising a CRISPR nucleic acid sequence and a DNA repair template associated with each other in a covalent and/or non-covalent way for CRISPR based genome engineering. Further provided is a molecular complex additionally comprising at least one CRISPR polypeptide. All components within the complex are in physical proximity. In addition, there is provided a plant, plant cell, a plant material, or a derivative, or progeny thereof comprising the hybrid RNA/DNA sequence and/or the molecular complex. Further, there is provided a method for modifying at least one DNA target sequence in a prokaryotic or eukaryotic cell as well as a method for manufacturing a plant or plant cell. Finally, there is provided the use of at least one hybrid RNA/DNA sequence, or use of a molecular complex for gene editing or genome engineering in a prokaryotic or eukaryotic cell or organism.

10 Claims, 5 Drawing Sheets
Specification includes a Sequence Listing.

(56) References Cited

OTHER PUBLICATIONS

Jinek et al., "A programmable dual-RNA-guided DNA endonuclease in adaptive bacterial immunity", Science 2012, vol. 337, pp. 816-821.
Burstein et al., "New CRISPR-Cas systems from uncultivated microbes", Nature, 2017, vol. 542, No. 7640, pp. 237-241.
Wyman et al., "DNA double-strand break repair: all's well that ends well", Annu. Rev. Genet., 2006, vol. 40, pp. 363-383.
Kwon et al., "Microhomology-mediated and nonhomologous repair of a double-strand break in the chloroplast genome of *Arabidopsis*", Proceedings of the National Academy of Sciences of the United States of America, 2010, vol. 107, No. 31, 13954-13959.
Charbonnel et al., "Kinetic analysis of DNA double-strand break repair pathways in *Arabidopsis*", DNA Repair, 2011, vol. 10, pp. 611-619.
Nishimasu et al., "Crystal structure of Cas9 in complex with guide RNA and target DNA", Cell, 2014, vol. 156, No. 5. pp. 935-949.
Tsai et al., "Dimeric CRISPR RNA-guided FokI nucleases for highly specific genome editing", Nature Biotechnology, vol. 32, No. 6, 2014, pp. 569-576.
Shechner et al., "CRISPR Display: A modular method for locus-specific targeting of long noncoding RNAs and synthetic RNA devices in vivo", Nature Methods, 2015, vol. 12, No. 7, pp. 664-670.
Mach, "Geminivirus Vectors Deliver Reagents for Plant Genome Engineering", Plant Cell, 2014, vol. 26, 1 page.
Baltes et al., "DNA Replicons for Plant Genome Engineering", The Plant Cell, 2014, vol. 26, pp. 151-163.
Richardson et al., "Enhancing homology-directed genome editing by catalytically active and inactive CRISPR-Cas9 using asymmetric donor DNA", Nature Biotechnology, 2016.
Miyata et al., "Polyplexes from Poly(aspartamide) Bearing 1, 2-Diaminoethane Side Chaines Induce pH-Selective, Endosomal Membrane Destabilization with Amplified Transfection and Negligible Cytotoxicity", J. Am. Chem. Soc., 2008, vol. 130, No. 48, pp. 16287-16294.
Tros de Illarduya et al., "Gene delivery by lipoplexes and polyplexes", Eur. J. Pharm. Sci., 2010, vol. 40, No. 3, pp. 159-170.
Kufer et al., "A revival of bispecific antibodies", Trends in Biotechnology, 2004, vol. 22, No. 5, pp. 238-244.
Laitinen et al., "Rational Design of an Active Avidin Monomer", The Journal of Biological Chemistry, 2003, vol. 278, No. 6. pp. 4010-4014.
Ma et al., "CRISPR-Cas9 nuclear dynamics and target recognition in living cells", J. Cell Biol., 2016, vol. 214, No. 5, pp. 529-537.
Makarova et al., "Annotation and Classification of CRISPER-Cas Systems", Methods Mol. Biol., 2015, vol. 1311, pp. 47-75.
Mann et al., "Cell labeling and proximity dependent biotinylation with engineered monomeric streptavidin", Technology, 2016, vol. 4, No. 3, pp. 152-158.
Swarts et al., "Argonaute of the archaeon Pyrococcus furiosus is a DNA-guided nuclease that targets cognate DNA", Nucleic Acids Research, vol. 43, No. 10, 2015, pp. 5120-5129.
Swarts et al., "DNA-guided DNA interference by a prokaryotic Argonaute", Nature, 2014, vol. 507, pp. 258-261.
Tissot et al., "Protein biotinylation in higher plants: characterization of biotin holocarboxylase synthetase activity from pea (*Pisum sativum*) leaves", Biochemical Journal, 1996, vol. 314(Pt 2), pp. 391-395.
Xiong et al., "Development of tumor targeting anti-MUC-I multimer: effects of di-scFv unpaired cysteine location on PEGylation and tumor binding", Protein Engineering Design & Selection, 2006, vol. 19, No. 8, pp. 359-367.
Office Action issued in European Application No. 18 703 730.4 dated Jul. 31, 2020.
Ronning et al., "Active Site Sharing and Subterminal Hairpin Recognition in a New Class of DNA Transposases", 2005, Molecular Cell, vol. 20, pp. 143-154.
Woo et al., "DNA-free genome editing in plants with preassembled CRISPR-Cas9 ribonucleoproteins", Nature Biotechnology, 2015, vol. 33, No. 11, pp. 1162-1165.
Garst et al., "Genomne-wide mapping of mutations at single-nucleotide resolution for protein, metabolic and genome engineering", Nature Biotechnology, vol. 35., No. 1, 2017, pp. 48-55.
Weeks et al., "Use of designer nucleases for targeted gene and genome editing in plants", Plant Biotechnology Journal, vol. 14, No. 2, 2016, pp. 483-495.
Jo et al., "Efficient Mitochondrial Genome Editing by CRISPR/Cas9", BioMed Research International, vol. 2015, Article ID 305716, 2015, pp. 1-10.
Lee et al., "Synthetically modified guide RNA and donor DNA are a versatile platform for CRISPR-Cas9 engineering", ELIFE, vol. 6, May 2, 2017, 17 pages.
Zhang et al., "Efficient precise knockin with a double cut HDR donor after CRISPR/Cas9-mediated double-stranded DNA Cleavage", Genome Biology, vol. 18, No. 35, Feb. 20, 2017, 18 pages.
Carlson-Stevermer et al., "Assembly of CRISPR ribonucleoproteins with biotinylated oligonucleotides via an RNA aptamer for precise gene editing", Nature Communications, vol. 8, Article No. 1711, 2017, 13 pages.
International Search Report and Written Opinion Issued in corresponding Application No. PCT/EP2018/052313 dated Mar. 16, 2018.
Ali et al., "Fusion of the Cas9 endonuclease and the VirD2 relaxase facilitates homology-directed repair for precise genome engineering in rice", Communications Biology, 2020, vol. 3, No. 44, 13 pages.
Aird, "Increasing Cas9-mediated homology-directed repair efficiency through covalent tethering of DNA repair template", Communications Biology, 2018, vol. 1, No. 54, 6 pages.
Van Kregten et al., "Agrobacterium-Mediated T-DNA Transfer and Integration by Minimal VirD2 Consisting of the Relaxase Domain and Type IV Secretion System Translocation Signal", Molecular Plant-Microbe Interactions, 2009, vol. 22, No. 11, pp. 1356-1365.
Durrenberger et al., "Covalently bound VirD2 protein of Agrobacterium tumefaciens protects the T-DNA from exonucleolytic degradation", PNAS, 1989, vol. 86, pp. 9154-9158.

\* cited by examiner

HYBRID NUCLEIC ACID SEQUENCES FOR GENOME ENGINEERING

CROSS-REFERENCE TO RELATED APPLICATIONS

This application is a U.S. National Phase of International Patent Application No. PCT/EP2017/063067, filed May 30, 2017, which claims priority to U.S. Provisional Application No. 62/344,109, filed on Jun. 1, 2016, both of which are herein incorporated by reference in their entirety.

SEQUENCE LISTING

This application contains a Sequence Listing which has been submitted in ASCII format via EFS-Web and is hereby incorporated by reference herein in its entirety. The ASCII text file created on Nov. 28, 2018, is named SequenceListing.txt and is 4,848 bytes in size.

TECHNICAL FIELD

The present invention relates to hybrid nucleic acid sequence constructs comprising a CRISPR nucleic acid sequence and a DNA repair template nucleic acid sequence associated with each other in a covalent and/or non-covalent way to provide a flexible and stable tool for CRISPR based gene editing or genome engineering by increasing the local availability of a repair template around the site of a double strand break in the DNA. Further provided is a molecular complex additionally comprising at least one CRISPR polypeptide so that all components within the complex are in physical proximity and thus readily available in situ at the site of DNA target sequence to be modified in a targeted and controlled way. In addition, there is provided a plant, plant cell, a plant material, or a derivative, or a progeny thereof comprising or edited by the hybrid RNA/DNA sequence and/or the molecular complex. Based on these tools, there is provided a method for modifying at least one DNA target sequence in a prokaryotic or eukaryotic cell as well as a method for manufacturing a plant or plant cell. Finally, there is provided the use of at least one hybrid RNA/DNA nucleic acid sequence, or use of a molecular complex comprising associated with each other a CRISPR RNA, a repair template DNA and a CRISPR polypeptide sequence for gene editing or genome engineering in a prokaryotic or a eukaryotic cell or organism, preferably in a plant cell or organism.

BACKGROUND OF THE INVENTION

Precision gene editing or genome engineering has evolved as one of the most important areas of genetic engineering allowing the targeted and site-directed manipulation of a genome of interest. An indispensable prerequisite for site-directed genome engineering are programmable nucleases, which can be used to break a nucleic acid of interest at a defined position to induce either a double-strand break (DSB) or one or more single-strand breaks. Alternatively, said nucleases can be chimeric or mutated variants, no longer comprising a nuclease function, but rather operating as recognition molecules in combination with another enzyme. Those nucleases or variants thereof are thus key to any gene editing or genome engineering approach. In recent years, many suitable nucleases, especially tailored endonucleases have been developed comprising meganucleases, zinc finger nucleases, TALE nucleases and CRISPR nucleases, comprising, for example, Cas or Cpf1 nucleases as part of the Clustered Regularly Interspaced Short Palindromic Repeats (CRISPR) system.

CRISPRs (Clustered Regularly Interspaced Short Palindromic Repeats) in their natural environment originally evolved in bacteria where the CRISPR system fulfils the role of an adaptive immune system to defend against viral attack. Upon exposure to a virus, short segments of viral DNA are integrated into the CRISPR locus. RNA is transcribed from a portion of the CRISPR locus that includes the viral sequence. That RNA, which contains sequence complementary to the viral genome, mediates targeting of a CRISPR effector protein to a target sequence in the viral genome. The CRISPR effector protein cleaves and thereby interferes with replication of the viral target. Over the last years, the CRISPR system has successfully been adapted for gene editing or genome engineering also in eukaryotic cells. Editing in animal cells and therapeutic applications for human beings are presently of significant research emphasis. The targeted modification of complex animal and also plant genomes still represents a demanding task.

A CRISPR system in its natural environment describes a molecular complex comprising at least one small and individual non-coding RNA in combination with a Cas nuclease or another CRISPR nuclease like a Cpf1 nuclease (Zetsche et al., "Cpf1 Is a Single RNA-Guides Endonuclease of a Class 2 CRISPR-Cas System", Cell, 163, pp. 1-13, October 2015) which can produce a specific DNA double-stranded break. Presently, CRISPR systems are categorized into 2 classes comprising five types of CRISPR systems, the type II system, for instance, using Cas9 as effector and the type V system using Cpf1 as effector molecule (Makarova et al., Nature Rev. Microbiol., 2015). In artificial CRISPR systems, a synthetic non-coding RNA and a CRISPR nuclease and/or optionally a modified CRISPR nuclease, modified to act as nickase or lacking any nuclease function, can be used in combination with at least one synthetic or artificial guide RNA or gRNA combining the function of a crRNA and/or a tracrRNA (Makarova et al., 2015, supra). The immune response mediated by CRISPR/Cas in natural systems requires CRISPR-RNA (crRNA), wherein the maturation of this guiding RNA, which controls the specific activation of the CRISPR nuclease, varies significantly between the various CRISPR systems which have been characterized so far. Firstly, the invading DNA, also known as a spacer, is integrated between two adjacent repeat regions at the proximal end of the CRISPR locus. Type II CRISPR systems code for a Cas9 nuclease as key enzyme for the interference step, which system contains both a crRNA and also a trans-activating RNA (tracrRNA) as the guide motif. These hybridize and form double-stranded (ds) RNA regions which are recognized by RNAseIII and can be cleaved in order to form mature crRNAs. These then in turn associate with the Cas molecule in order to direct the nuclease specifically to the target nucleic acid region. Recombinant gRNA molecules can comprise both the variable DNA recognition region and also the Cas interaction region and thus can be specifically designed, independently of the specific target nucleic acid and the desired Cas nuclease. As a further safety mechanism, PAMs (protospacer adjacent motifs) must be present in the target nucleic acid region; these are DNA sequences which follow on directly from the Cas9/RNA complex-recognized DNA. The PAM sequence for the Cas9 from *Streptococcus pyogenes* has been described to be "NGG" or "NAG" (Standard IUPAC nucleotide code) (Jinek et al, "A programmable dual-RNA-guided DNA endonuclease in adaptive bacterial immunity", Science 2012, 337:

816-821). The PAM sequence for Cas9 from *Staphylococcus aureus* is "NNGRRT" or "NNGRR(N)". Further variant CRISPR/Cas9 systems are known. Thus, a *Neisseria meningitidis* Cas9 cleaves at the PAM sequence NNNNGATT. A *Streptococcus thermophilus* Cas9 cleaves at the PAM sequence NNAGAAW. Recently, a further PAM motif NNNNRYAC has been described for a CRISPR system of *Campylobacter* (WO 2016/021973 A1). For Cpf1 nucleases it has been described that the Cpf1-crRNA complex, without a tracrRNA, efficiently recognize and cleave target DNA proceeded by a short T-rich PAM in contrast to the commonly G-rich PAMs recognized by Cas9 systems (Zetsche et al., supra). Furthermore, by using modified CRISPR polypeptides, specific single-stranded breaks can be obtained. The combined use of Cas nickases with various recombinant gRNAs can also induce highly specific DNA double-stranded breaks by means of double DNA nicking. By using two gRNAs, moreover, the specificity of the DNA binding and thus the DNA cleavage can be optimized. Further CRISPR effectors like CasX and CasY effectors originally described for bacteria, are meanwhile available and represent further effectors, which can be used for genome engineering purposes (Burstein et al., "New CRISPR-Cas systems from uncultivated microbes", Nature, 2017, 542, 237-241).

Presently, for example, Type II systems relying on Cas9, or a variant or any chimeric form thereof, as endonuclease have been modified for genome engineering. Synthetic CRISPR systems consisting of two components, a guide RNA (gRNA) also called single guide RNA (sgRNA) and a non-specific CRISPR-associated endonuclease can be used to generate knock-out cells or animals by co-expressing a gRNA specific to the gene to be targeted and capable of association with the endonuclease Cas9. Notably, the gRNA is an artificial molecule comprising one domain interacting with the Cas or any other CRISPR effector protein or a variant or catalytically active fragment thereof and another domain interacting with the target nucleic acid of interest and thus representing a synthetic fusion of crRNA and tracrRNA ("single guide RNA" (sgRNA) or simply "gRNA" (Science 2012, supra). The genomic target can be any ~20 nucleotide DNA sequence, provided that the target is present immediately upstream of a PAM sequence. The PAM sequence is of outstanding importance for target binding and the exact sequence is dependent upon the species of Cas9 and, for example, reads 5' NGG 3' or 5' NAG 3' (Standard IUPAC nucleotide code) (Jinek et al., Science 2012, supra) for a *Streptococcus pyogenes* derived Cas9. The PAM sequence for Cas9 from *Staphylococcus aureus* is NNGRRT or NNGRR(N). Many further variant CRISPR/Cas9 systems are known, including inter alia, *Neisseria meningitidis* Cas9 cleaving the PAM sequence NNNNGATT. A *Streptococcus thermophilus* Cas9 cleaving the PAM sequence NNAGAAW. Using modified Cas nucleases, targeted single strand breaks can be introduced into a target sequence of interest. The combined use of such a Cas nickase with different recombinant gRNAs highly site specific DNA double strand breaks can be introduced using a double nicking system. Using one or more gRNAs can further increase the overall specificity and reduce off-target effects.

Once expressed, the Cas9 protein and the gRNA form a ribonucleoprotein complex through interactions between the gRNA "scaffold" domain and surface-exposed positively-charged grooves on Cas9. Cas9 undergoes a conformational change upon gRNA binding that shifts the molecule from an inactive, non-DNA binding conformation, into an active DNA-binding conformation. Importantly, the "spacer" sequence of the gRNA remains free to interact with target DNA. The Cas9-gRNA complex will bind any genomic sequence with a PAM, but the extent to which the gRNA spacer matches the target DNA determines whether Cas9 will cut. Once the Cas9-gRNA complex binds a putative DNA target, a "seed" sequence at the 3' end of the gRNA targeting sequence begins to anneal to the target DNA. If the seed and target DNA sequences match, the gRNA will continue to anneal to the target DNA in a 3' to 5' direction (relative to the polarity of the gRNA).

CRISPR/Cas9 and likewise CRISPR/Cpf1 and other CRISPR systems are highly specific when gRNAs are designed correctly, but especially specificity is still a major concern, particularly for clinical uses based on the CRISPR technology. The specificity of the CRISPR system is determined in large part by how specific the gRNA targeting sequence is for the genomic target compared to the rest of the genome.

The kingdom of Plantae comprises species of high heterogeneity and diversity given the genomic and phenotypic differences of green algae, bryophytes, pteridophytes and land plants. Plant genomes and their complexity represent a challenge for high precision gene editing or genome engineering. *Zea mays* (maize or corn), for example, has the highest world-wide production of all grain crops, yielding 875 million tonnes in 2012. It has a large genome of about 2.4 gigabases (Gb) with a haploid chromosome number of 10 (Schnable et al, 2009; Zhang et al, 2009). *Triticum aestivum* (bread wheat), for instance, is hexaploid, with a genome size estimated at ~17 Gb. *Beta vulgaris* ssp. *vulgaris* (sugar beet) has a genome size ranging from about 470 megabases (Mb) to about 569 Mb. The specific architecture and composition of plant cells and the peculiar development of plants demands a specific adaption for CRISPR tools when intended for use to modify a target sequence within a plant cell. Therefore, CRISPR tools and principles associated therewith established for animal, particularly mammalian, systems will not necessarily work in a plant cell of interest and there is a need for specific strategies for establishing the technology to achieve a broad application in plants.

Likewise, animal, and especially mammalian genomes are complex, for example comprising 2.7 Gb for the genome of *Mus musculus* or 3.2 Gb for the genome of *Homo sapiens*. Especially, when CRISPR based gene editing or genome engineering approaches are intended to be used for precision gene editing or genome engineering of targets within the human genome, there is thus an urgent need to provide high specificity, as any kind of off-target effect could be highly detrimental.

Another aspect to be critically considered for genome engineering is the repair mechanism necessary after the cleavage of a genomic target site of interest, as double-strand breaks (DSBs) or DNA lesions in general are detrimental for the integrity of a genome. DSBs in genomic material can be caused by ionizing radiation, chemicals, oxidation, enzymes, and single-strand breaks during replication and represent a serious form of DNA damage which can result in gene loss, stalled DNA replication, and cell death. It is thus of outstanding importance that the cellular machinery provides mechanisms of double-strand break (DSB) repair. Cells possess intrinsic mechanisms to attempt to repair any double or single-stranded DNA damage. DSB repair mechanisms have been divided into two major basic types, non-homologous end joining (NHEJ) and homologous recombination (HR). Homology based repair mechanisms in general are usually called homology-directed repair (HDR).

NHEJ is the dominant nuclear response in animals and plants which does not require homologous sequences, but is often error-prone and thus potentially mutagenic (Wyman C., Kanaar R. "DNA double-strand break repair: all's well that ends well", Annu. Rev. Genet. 2006; 40, 363-83). Repair by HDR requires homology, but those HDR pathways that use an intact chromosome to repair the broken one, i.e. double-strand break repair and synthesis-dependent strand annealing, are highly accurate. In the classical DSB repair pathway, the 3' ends invade an intact homologous template then serve as a primer for DNA repair synthesis, ultimately leading to the formation of double Holliday junctions (dHJs). dHJs are four-stranded branched structures that form when elongation of the invasive strand "captures" and synthesizes DNA from the second DSB end. The individual HJs are resolved via cleavage in one of two ways. Synthesis-dependent strand annealing is conservative, and results exclusively in non-crossover events. This means that all newly synthesized sequences are present on the same molecule. Unlike the NHEJ repair pathway, following strand invasion and D loop formation in synthesis-dependent strand annealing, the newly synthesized portion of the invasive strand is displaced from the template and returned to the processed end of the non-invading strand at the other DSB end. The 3' end of the non-invasive strand is elongated and ligated to fill the gap. There is a further pathway of HDR, called break-induced repair pathway not yet fully characterized. A central feature of this pathway is the presence of only one invasive end at a DSB that can be used for repair.

A further HDR pathway is single-strand annealing (SSA). SSA is non-conservative and occurs between direct repeats >30 bp and results in deletions. In recent years, microhomology-mediated end joining (MMEJ) has been recognized as a distinct type of DSB repair in eukaryotes. Only very short (2-14 bp) regions of homology are needed for this pathway, and it typically leaves deletions like SSA. It has also been distinguished genetically from the HR and NHEJ pathways and in mammalian cells acts as a backup to NHEJ (Kwon, T., Huq, E., & Herrin, D. L. (2010). Microhomology-mediated and nonhomologous repair of a double-strand break in the chloroplast genome of *Arabidopsis*. *Proceedings of the National Academy of Sciences of the United States of America*, 107(31), 13954-13959). Furthermore, in plants, so called alternative end-joining (AEJ) pathways have been described (Charbonnel C, Allain E, Gallego M E, White C I (2011) Kinetic analysis of DNA double-strand break repair pathways in *Arabidopsis*. DNA Repair (Amst) 10: 611-619). In sum, HR/HDR employs a homologous stretch of DNA on a sister chromatid as a template. It thus provides high fidelity, however, less efficiency. NHEJ in contrast is highly efficient and a straightforward pathway that can rejoin the two ends independently of significant homology, whereas this efficiency is accompanied by the drawback that this process is error-prone and can be associated with insertions or deletions.

For gene editing or genome engineering approaches seeking to influence the natural repair pathways thus require physical design of a repair template (RT), which is an important parameter. It can be possible to provide the RT as either ssDNA or as partially dsDNA. Short oligonucleotides have been used successfully for HR in a wide variety of animal systems when delivered either as ssDNA or as dsDNA. Reported gene editing frequencies are not as high as with long dsDNA RTs (Yang et al., 2013). Delivered as free molecules, ssDNA RTs in the range from about 70-99 bp have been used successfully in animal systems (Yang et al., 2013; Davis and Maizels, 2014), and in some cases these are better than longer ssDNA RTs (e.g., Yang et al., 2013). ssDNA RTs shorter than 70 bp are also commonly used, but with slightly reduced gene editing frequency. Strand bias relative to the gRNA in the context of CRISPR based gene editing or genome engineering editing has also been found with ssDNA RTs (Yang et al., 2013).

Current protocols relying on CRISPR tools for genome editing in combination with a repair template (RT) exclusively rely on the separate provision of the nucleic acid RT, either double or single-stranded, which in turn recognizes the break in the DNA to be repaired solely by base pairing and hybridization. The physical and temporal availability of the RT at the site where a DNA break is induced, can, however, not be controlled by the methods presently available, as those methods do not provide for the precise spatial and temporal provision of the RT in the right configuration, concentration and thus stochiometry at the compartment, where repair has to take place, preferably immediately after induction of a targeted DNA break to specifically control not only the break, but also the repair event.

In the literature, it has been documented that homologous recombination between two sequences occurs more frequently if the sequences are in close proximity within the nucleus rather than with a significant amount of separation. For example, analysis in *Arabidopsis* of the gene editing rate obtained between chromosomally located donor molecules and targets was higher in both cases where the donor existed on the same chromosome as the target than in the other cases where the two loci were located on distinct chromosomes (Fauser et al., 2012). However, these findings have never been exploited in a rational way to optimize CRISPR based gene editing or genome engineering approaches in eukaryotic cells.

US 2015/0376645 A1 discloses compositions and methods of gene therapy using MiniVectors™ comprising a nucleic acid sequence as a tool for DNA repair, alteration, or replacement. The MiniVector comprises a nucleic acid sequence template for homology-directed repair, alteration, or replacement of the targeted DNA sequence within a cell in vivo or in vitro, where the MiniVector lacks both a bacterial origin of replication and an antibiotic selection gene, and where the MiniVector has a size up to about 2,500 bp. The effect of the MiniVector encoded repair template, however, exclusively relies on the complementarity of the repair template sequence to a nucleic acid sequence near the target DNA sequence and the physical availability of the repair template at the target site of interest is not controlled at all.

US 2015/0082478 A1 is directed to the compositions and methods employing a guide RNA/Cas endonuclease system in plants for genome modification of a target sequence in the genome of a plant or plant cell, for selecting plants, for gene editing, and for inserting a polynucleotide of interest into the genome of a plant. The methods and compositions employ a guide RNA/Cas endonuclease system to provide for an effective system for modifying or altering target sites and nucleotides of interest within the genome of a plant, plant cell or seed. For mediating repair of the DSB introduced, a separate HDR repair DNA vector is disclosed and employed, or spontaneous repair via NHEJ is suggested.

EP 2 958 996 A1 seeks to overcome the problem of specific DSB repair by providing an inhibitor of NHEJ mechanisms in cell to increase gene disruption mediated by a nuclease (e.g., ZFN or TALEN) or nuclease system (e.g.

CRISPR/Cas). By inhibiting the critical enzymatic activities of these NHEJ DNA repair pathways, using small molecule inhibitors of DNA-dependent-protein kinase catalytic subunit (DNA-PKcs) and/or Poly-(ADP-ribose) polymerase 1/2 (PARP1/2), the level of gene disruption by nucleases is increased by forcing cells to resort to more error prone repair pathways than classic NHEJ, such as alternate NHEJ and/or microhomology mediated end-joining. Therefore, an additional chemical is added in the course of genome editing, which might, however, be disadvantageous for several cell types and assays. This could also affect the genome integrity of the treated cells and/or the regenerative potential.

Nishimasu et al. ("Crystal structure of Cas9 in complex with guide RNA and target DNA", Cell, 156(5): 935-49, 2014) discloses crystal structure of *Streptococcus pyogenes* Cas9 in complex with sgRNA and its target DNA at 2.5 Å resolution, specifically revealing the Cas9-sgRNA-DNA ternary complex and the two lobes of Cas9, i.e. a recognition lobe and a nuclease lobe. Despite the detailed structural information provided, there is, however, no further functional technical teaching how the structural knowledge could be made available for genome editing, let alone for DSB repair issues.

Tsai et al. ("Dimeric CRISPR RNA-guided FokI nucleases for highly specific genome editing", Nature Biotechnology, 32, 569-576 (2014), doi:10.1038/nbt.2908) discloses RNA-guided FokI nucleases (RFN) and Csy4-based multiplex gRNA expression systems. It was found, for human cells as targets, that Cas9 loaded with a gRNA possessing 28 bp of additional sequence on the 3' end plus an associated 187 amino acid (21.4 kD) Csy4 (Cash) protein maintained at least 90% activity in DSB induction compared to standard gRNA controls. There is, however, no disclosure on possible implications of these findings to bring together the concept of a DNA repair template with a gRNA to optimize CRISPR/Cas mediated genome editing.

Further, Shechner et al. ("Multiplexable, locus-specific targeting of long RNAs with CRISPR-Display", Nature Methods, 12(7), 664-670 (2015), doi: 10.1038/nmeth.3433) demonstrated the capacity for Cas9 to interact with specific genomic target sites even when loaded with sgRNAs transcriptionally fused to long noncoding, ssRNA sequences. The transcriptional fusions were tested at the 5'- and 3'-ends of sgRNAs and tracrRNAs, and at an internal stem-loop of the standard sgRNA structure. All configurations were capable of sequence-specific targeting by Cas9, although the 5' and 3' transcriptional fusions on the sgRNA were most effective. The 3' fusions showed specific targeting with ssRNA cargo as large as 4,819 bp. Shechner et al., however, exclusively focuses on the aspect of multiplexing and ectopic targeting and does not teach any repair template or a (s)gRNA associated with a repair template tool to address the problem of providing efficient sgRNA/repair template complexes for high precision genome engineering.

Therefore, there exists an ongoing need in providing suitable CRISPR tools, particularly tools optimized for the precision editing of plants, especially major crop plants, which combine high precision genome cleavage, for example by providing gRNAs optimized for the target site in a cell of interest and simultaneously providing the possibility for mediating highly precise and accurate HDR and thus targeted repair of a DSB, which is imperative to control a gene editing or genome engineering intervention.

It is thus an aim to present novel strategies to provide repair templates for precision genome editing, especially suitable for eukaryotic cells, including yeast, animal and plant cells.

Despite the tremendous advancements of genome editing in biotechnology, e.g. for therapeutic approaches, gene therapy or plant or microbe genome engineering for targeted trait development, there are still major problems and concerns with respect to the specificity of a targeted genome modification to be introduced or off-target effects. This problem is inter alia associated with the degree of precision which can be obtained when inducing a break and the associated repair of a genomic target nucleic acid of interest.

As any kind of gene editing or genome engineering approach inducing a DSB introduces a potentially harmful DNA break and possibly an undesired DNA repair mechanism leading to unwanted nucleic acid exchanges, there is an ongoing need in developing more efficient methods and tools to achieve highly precise and controlled gene editing or genome engineering which also implies the use of targeted DNA repair templates (RTs).

Another problem frequently associated with the provision of successful genome engineering without mediating off-target effects is the physical availability of a repair template at the site of the DSB exactly at the time the break is made and thus has to be repaired. Usually the desired editing event is outcompeted by repair through the non-homologous end-joining (NHEJ) pathway or through recombination with endogenous homologous sequence as detailed above. Depending on the target organism to be modified, this demands a concentred strategy for introducing a gene editing or genome engineering tool along with a repair template of interest so that all tools, i.e. the endonuclease scissors, the guiding gRNA and the repair template can, with the appropriate timing, reach the compartment within a cell comprising the genome, i.e. preferably the nucleus, or any other genome carrying compartment, like the mitochondria. One method to partially overcome this limitation is by amplifying the repair template and thus increasing the abundance of the template in the nucleus and presumably making it more available to use for repair of the DSB by help of a geminivirus vector (see e.g. Mach, Plant Cell. 2014, doi:10.1105/tpc.114.122606; and Baltes et al., Plant Cell. 2014, doi: 10.1105/tpc.113.119792). The repair template, however, is delivered as separate physical entity and thus there is no mechanism of control ascertaining that the repair template will indeed be present at the place DNA repair is needed exactly at the time point, when a DSB is introduced by an endonuclease.

Concerning CRISPR applications, there is the frequent suggestion to use free ssDNA nucleotides as repair templates or plasmid borne repair templates ([online] Retrieved from the Internet <URL:http://blog.addgene.org/cri spr-101-homology-directed-rep air). yet no strategy is disclosed or suggested, which would guarantee that the repair template is indeed brought into physical contact with the DSB to be repaired in situ when a DSB is generated.

At this point, the peculiar differences of the delivery of gene editing or genome engineering and/or repair template tools as necessary for different target cells become evident. In this regard, plant cells have certain distinguishing features, including cell walls, making gene editing or genome engineering in plant cells a completely different task than gene editing or genome engineering as established for animal/mammalian cells, as the delivery of genome editing and/or repair tools is mediated by different transformation, transfection and/or transduction methods than for other eukaryotic cells. These peculiarities, however, have to be taken into consideration for achieving highly precise plant genome editing. Currently, there exists a variety of plant transformation methods to introduce genetic material in the form of a genetic construct into a plant cell of interest, comprising biological and physical means. A common biological means is transformation with *Agrobacterium* spp. which has been used for decades for a variety of different plant materials. Viral vector mediated plant transformation represents a further strategy for introducing genetic material into a cell of interest. Physical means finding application in plant biology are particle bombardment, also named biolistic transfection or microparticle-mediated gene transfer, which refers to a physical delivery method for transferring a coated microparticle or nanoparticle comprising a nucleic acid or a genetic construct of interest into a target cell or tissue. Physical introduction means are suitable to introduce nucleic acids, i.e. RNA and/or DNA, and proteins. Likewise, specific transformation or transfection methods exist for specifically introducing a nucleic acid or an amino acid construct of interest into a plant cell, including electroporation, microinjection, nanoparticles, and cell-penetrating peptides (CPPs). Furthermore, chemical-based transfection methods exist to introduce genetic constructs and/or nucleic acids and/or proteins, comprising inter alia transfection with calcium phosphate, transfection using liposomes, e.g. cationic liposomes, or transfection with cationic polymers, including DEAD-dextran or polyethylenimine, or combinations thereof. Said delivery methods and delivery vehicles or cargos thus inherently differ from delivery tools as used for other eukaryotic cells, including animal and mammalian cells and every delivery method has to be specifically fine-tuned and optimized so that a construct of interest for mediating genome editing can be introduced into a specific compartment of a target cell of interest in a fully functional and active way.

Therefore, it was an object of the present invention to overcome the pronounced need in providing new tools and methods suitable for high precision genome editing in eukaryotic cells, including plant cells, particularly in the field of CRISPR mediated genome editing to overcome the ongoing limitation in the field of gene editing regarding the physical availability of the repair template at the site and time the DSB is repaired and thus the competition by DNA repair mechanisms through the non-homologous end-joining pathway (NHEJ) or through recombination with (endogenous) homologous sequence (HR/HDR). It was another object of the present invention to provide a simplified CRISPR toolkit which can be utilized for site-directed genome editing in eukaryotic cells without the need of providing a separate repair template or repair oligonucleotide, yet a molecule or a molecular complex which unifies CRISPR nucleic acid and repair template properties and simultaneously can be easily delivered to the target site, i.e. a prokaryotic cell, a eukaryotic genome, particularly the genome of an animal cell, particularly a mammalian cell, or of a plant cell, as the degree of precision to be achieved during genome editing of animal or plant cells still has to be improved to comply with necessarily high regulatory requirements as set by medical and food administration authorities. The risk for off-target integrations of the repair template that is a hybrid with RNA and physically bound to the protein-RNA nuclease complex as disclosed herein is lower than for a ss- or ds-DNA repair template introduced as free molecules into the cell. In addition, it was an object to provide a delivery tool that is specifically optimized for transferring a plant specific genome editing construct with the help of a plant specific delivery method. In addition, it was an object to provide an approach which can rely on transient editing activity using transiently provided RNA and site-specific nucleases, if desired, because of the sensitivity in certain jurisdictions towards any form of genetic modification that integrates foreign DNA as an intermediate in the production process. Finally it was an object of the present invention to provide a gene editing or genome engineering method, which is superior to recent methods in that it is time saving regarding the testing of new targets as it should not require cumbersome cloning and pre-testing.

SUMMARY OF THE INVENTION

The above identified objects have been achieved according to the present invention by solving the problem of repair template availability by delivering the repair template to the site of the DSB by directly harnessing it as "cargo" to the nuclease complex. Directing the repair template to the double strand break at the time the break is made in situ increases the local availability of the repair template (RT) for exploitation in repair of the break. Thereby, the CRISPR nucleic acid/RT tools according to the present invention do not only assist in providing custom-made repair templates, but furthermore can help to increase the frequency and/or specificity of gene editing events. This idea exploits the presence of a nucleic acid, e.g., a gRNA, in a CRISPR nuclease complex and in vitro nucleic acid manipulations to combine the functionalities of site-specific nuclease and repair templates into a single molecular complex for simultaneous genome cleavage and targeted repair combined with specific delivery tools and methods for delivering the genome editing tool(s) and/or the repair template into a compartment of interest into a target cell. This system thus allows a higher specificity and thus reduced off-target effects of a CRISPR approach, which is needed to minimize off-target cleavage in large animal, particularly mammalian, or sometimes even more complex plant genomes.

Specifically, the above objects have been achieved by providing, in a first aspect, a hybrid nucleic acid sequence comprising or consisting of at least one RNA and at least one DNA nucleic acid sequence, comprising: (a) a CRISPR nucleic acid sequence or a guide nucleic acid sequence, comprising at least one RNA nucleic acid sequence, wherein the CRISPR nucleic acid sequence or the guide nucleic acid sequence comprises (i) a first sequence portion that is complementary to a first DNA target sequence, and (ii) a second sequence portion, wherein the second sequence portion is configured to interact with a CRISPR polypeptide; and comprising associated with the CRISPR nucleic acid sequence or the guide nucleic acid sequence: (b) a repair template nucleic acid sequence, comprising a DNA nucleic acid sequence, wherein the repair template nucleic acid sequence comprises at least one portion being complementary to a second DNA target sequence, and wherein the repair template nucleic acid sequence is configured to mediate targeted homology directed repair; and (c) optionally: a linker region between the CRISPR nucleic acid sequence or the guide nucleic acid sequence and the repair template nucleic acid sequence; wherein the hybrid nucleic acid sequence is capable of interacting with a CRISPR polypeptide so that the CRISPR polypeptide can recognize the first DNA target sequence and optionally induce a DNA break, and wherein the hybrid nucleic acid sequence directs genome engineering through homology directed repair mediated by the repair template nucleic acid sequence at the site of the second DNA target sequence, wherein the second DNA target sequence represents a cell's endogenous DNA sequence.

In one embodiment of the first aspect, there is provided a hybrid nucleic acid sequence, wherein the repair template nucleic acid sequence and/or the CRISPR nucleic acid sequence or the guide nucleic acid sequence comprise a nucleotide sequence selected from a naturally or non-naturally occurring nucleotide sequence, including a synthetic nucleotide sequence, optionally comprising backbone and/or base modifications, wherein the CRISPR nucleic acid sequence or the guide nucleic acid sequence comprises a single-stranded, or partially single-stranded, RNA nucleotide sequence, and wherein the repair template nucleic acid sequence comprises a single-stranded or a double-stranded DNA nucleotide sequence.

In another embodiment of the above aspect, there is provided a hybrid nucleic acid sequence, wherein repair template nucleic acid sequence is associated with the CRISPR nucleic acid sequence or the guide nucleic acid sequence at the 3' end of the CRISPR nucleic acid sequence or the guide nucleic acid sequence, and/or wherein the repair template nucleic acid sequence is associated with the 5' end of the CRISPR nucleic acid sequence or the guide nucleic acid sequence, and/or wherein the repair template nucleic acid sequence is located within the CRISPR nucleic acid sequence or the guide nucleic acid sequence.

In yet another embodiment of the above first aspect according to the present invention, there is provided a hybrid nucleic acid sequence, wherein at least one repair template nucleic acid sequence is covalently attached to at least one CRISPR nucleic acid sequence or at least one guide nucleic acid sequence, and/or wherein at least one repair template nucleic acid sequence is non-covalently attached to at least one CRISPR nucleic acid sequence or at least one guide nucleic acid sequence.

In a second aspect according to the present invention there is provided a molecular complex comprising at least one hybrid nucleic acid sequence according to the first aspect of the present invention and at least one CRISPR polypeptide, wherein the at least one hybrid nucleic acid sequence and at least one CRISPR polypeptide are associated in a functional way.

In one embodiment according to any aspect of the present invention, the at least one CRISPR polypeptide is independently selected from the group consisting of a Cas polypeptide of *Streptococcus* spp., including *Streptococcus pyogenes*, *Streptococcus thermophiles*, *Staphylococcus aureus*, or *Neisseria* spp., including *Neisseria meningitides*, *Corynebacter*, *Sutterella*, *Legionella*, *Treponema*, *Filifactor*, *Eubacterium*, *Lactobacillus*, *Mycoplasma*, *Bacteroides*, *Flaviivola*, *Flavobacterium*, *Sphaerochaeta*, *Azospirillum*, *Gluconacetobacter*, *Roseburia*, *Parvibaculum*, *Nitratifractor*, *Mycoplasma* and *Campylobacter*, or wherein the CRISPR polypeptide is selected from a Cpf1 polypeptide from an archaea or a *bacterium*, including a Cpf1 polypeptide of *Acidaminococcus* spp., including *Acidaminococcus* sp. BV3L6, *Lachnospiraceae* spp., including *Lachnospiraceae bacterium* ND2006, *Francisella* spp., including *Francisella novicida* U112, *Eubacterium eligens*, *Prevotella* spp., or *Porphyromonas* spp., or wherein the CRISPR polypeptide is selected from a CasX polypeptide or a CasY polypeptide, or variants and/or functional fragments and/or combinations thereof, including CRISPR polypeptide nickases, or a CRISPR polypeptide lacking endonucleolytic activity.

In a further aspect according to the present invention there is thus provided a plant, plant cell, a plant material, or a derivative, or a progeny thereof comprising or edited by at least one hybrid nucleic acid sequence according to the first aspect, or comprising the at least one molecular complex according to the second aspect of the present invention.

In yet a further aspect according to the present invention there is provided a method of modifying at least one DNA target sequence in a prokaryotic or eukaryotic cell (i) providing at least one prokaryotic or eukaryotic cell comprising at least one DNA target sequence comprising at least one first and at least one second DNA target sequence in a genomic region of interest; (ii) providing at least one molecular complex as detailed for the second aspect of the present invention comprising at least one hybrid nucleic acid sequence as detailed for the first aspect of the present invention and at least one CRISPR polypeptide; (iii) contacting the at least one molecular complex with the at least one DNA target sequence under suitable conditions to achieve complementary base pairing of the first sequence portion of the CRISPR nucleic acid sequence or of the guide nucleic acid sequence of the at least one hybrid nucleic acid sequence with the at least one first DNA target sequence to achieve recognition of the first DNA target sequence by the at least one CRISPR polypeptide and optionally induction of at least one DNA break by the at least one CRISPR polypeptide, wherein the at least one repair template nucleic acid sequence of the at least one hybrid nucleic acid sequence directs homology directed repair at the site of the at least one second DNA target sequence; and (iv) obtaining at least one prokaryotic or eukaryotic cell comprising a modification in the at least one DNA target sequence.

In one embodiment of this aspect, the at least one hybrid nucleic acid sequence of the molecular complex is provided to the at least one prokaryotic or eukaryotic cell independently of the at least one CRISPR polypeptide of the at least one molecular complex and the at least one molecular complex is assembled within the at least one prokaryotic or eukaryotic cell.

There is provided a further embodiment of the first aspect, wherein the at least one eukaryotic cell is a mammalian, primate, or human cell. In an embodiment, the cell is a human cell. In an embodiment, the cell is a hematopoietic cell, a lymphocyte, including B- and T-lymphcytes, a somatic cell, a germ cell, a prenatal cell, e.g., zygotic, blastocyst or embryonic cell, a stem cell, a mitotically competent cell, or a meiotically competent cell. Preferably, the cell is an immune cell or a cancer cell of an animal. In an embodiment, the DNA target region is a chromosomal nucleic acid.

In one embodiment of the first aspect, the cell is a plant cell, preferably a plant cell from a plant selected from the group consisting of *Hordeum vulgare, Hordeum bulbusom, Sorghum bicolor, Saccharum officinarium, Zea mays, Setaria italica, Oryza minuta, Oriza sativa, Oryza australiensis, Oryza alta, Triticum aestivum, Triticum durum, Secale cereale, Triticale, Malus domestica, Brachypodium distachyon, Hordeum marinum, Aegilops tauschii, Daucus glochidiatus, Beta vulgaris, Daucus pusillus, Daucus muricatus, Daucus carota, Eucalyptus grandis, Nicotiana sylvestris, Nicotiana tomentosiformis, Nicotiana tabacum, Nicotiana benthamiana, Solanum lycopersicum, Solanum tuberosum, Coffea canephora, Vitis vinifera, Erythrante guttata, Genlisea aurea, Cucumis sativus, Morus notabilis, Arabidopsis arenosa, Arabidopsis lyrata, Arabidopsis thaliana, Crucihimalaya himalaica, Crucihimalaya wallichii, Cardamine flexuosa, Lepidium virginicum, Capsella bursa pastoris, Olmarabidopsis pumila, Arabis hirsute, Brassica napus, Brassica oleracea, Brassica rapa, Raphanus sativus, Brassica juncacea, Brassica nigra, Eruca vesicaria subsp. sativa, Citrus sinensis, Jatropha curcas, Populus trichocarpa, Medicago truncatula, Cicer yamashitae, Cicer bijugum, Cicer arietinum, Cicer reticulatum, Cicer judai-* cum, *Cajanus cajanifolius, Cajanus scarabaeoides, Phaseolus vulgaris, Glycine max, Gossypium* sp., *Astragalus sinicus, Lotus japonicas, Torenia foumieri, Allium cepa, Allium fistulosum, Allium sativum, Helianthus annuus, Helianthus tuberosus* and *Allium tuberosum*, or any variety or subspecies belonging to one of the aforementioned plants.

In yet another embodiment of this aspect according to the present invention, the modification of the at least one DNA target sequence is a genome editing approach causing a trait selected from the group consisting of yield improvement, tolerance to abiotic stress, including drought stress, osmotic stress, heat stress, cold stress, oxidative stress, heavy metal stress, salt stress or waterlogging, tolerance to biotic stress including resistance to insects, resistance to bacteria, resistance to viruses, resistance to fungi or resistance to nematodes, tolerance to herbicides, including glyphosate, glufosinate, ALS inhibitors, and Dicamba, improved agronomic characteristics including lodging resistance, flowering time, shattering resistance, seed color, endosperm composition, nutritional content, or metabolic engineering, including genome editing to allow a molecular pharming approach in at least one plant cell.

In a further embodiment of this aspect, the method further comprising the following step: (v) identifying and/or selecting at least one prokaryotic or eukaryotic cell comprising the modification in the at least one DNA target sequence.

In a further aspect of the present invention, there is provided a method for manufacturing a plant or plant cell comprising the following steps: (i) performing a method as detailed for the preceding aspect of the present invention, wherein the at least one eukaryotic cell is a plant cell; (ii) obtaining at least one plant or a progeny thereof from the at least one plant cell from step (i); (iii) optionally: determining the modification in the at least one DNA target sequence in the at least one cell of the at least one plant or a progeny thereof.

In one embodiment of the preceding aspect according to the present invention, the at least one plant or plant cell is selected from a monocotyledonous or a dicotyledonous plant, preferably, the plant is selected from the group consisting of *Zea* spp., including *Zea mays, Nicotiana benthamiana*, or *Beta* spp, including *Beta vulgaris*, or *Secale* ssp., including *Secale* cereal, or *Triticum* ssp., including *Triticum aestivum*.

In yet a further aspect according to the present invention, there is provided the use of at least one hybrid RNA/DNA nucleic acid sequence according to the first aspect of the present invention, or use of a molecular complex according to the second aspect of the present invention for genome editing in a prokaryotic or a eukaryotic cell or organism, preferably in a plant cell or organism.

Further aspects and embodiments of the present invention can be derived from the subsequent detailed description, the drawings, the sequence listing as well as the attached set of claims.

BRIEF DESCRIPTION OF THE DRAWINGS

FIG. 1a shows configurations, wherein the CRISPR nucleic acid sequence is located 5' and the RT is associated with the CRISPR nucleic acid at the 3'end of the CRISPR nucleic acid. (A) Non-covalent association by Watson-Crick base pairing of a single-stranded repair template (RT) (ssDNA) to a CRISPR nucleic acid, wherein the CRISPR nucleic acid comprises an RNA molecule containing the sequence functioning as a tracrRNA, as a crRNA (e.g., for Cpf1, or Cpf1-derived CRISPR effectors), or a combination thereof (e.g., sgRNA). (B) Covalent association of a CRISPR nucleic acid and a single-stranded RT (ssDNA). This form can be manufactured by sequential synthesis of the RNA and RT portions as a single molecule, or by ligation of separate portions to form a single molecule. (C) Non-covalent association of a CRISPR nucleic acid associated with a double-stranded RT (dsDNA). (D) Covalent association of a CRISPR nucleic acid and a double stranded RT (dsDNA).

FIG. 1b shows configurations, wherein the RT is located 5' and the CRISPR nucleic acid is associated with the 3'end of the RT. (A) Non-covalent association by Watson-Crick base pairing of a single-stranded repair template (RT) (ssDNA) with a CRISPR nucleic acid, wherein the CRISPR nucleic acid comprises an RNA molecule containing the sequence functioning as a tracrRNA, or as a crRNA (e.g., for Cpf1, or Cpf1-derived CRISPR effectors), or a combination thereof (e.g., sgRNA). (B) Covalent association of a single-stranded RT (ssDNA) to the CRISPR nucleic acid. This form can be manufactured by sequential synthesis of the RNA and RT portions as a single molecule, or by ligation of separate portions to form a single molecule. (C) Non-covalent association of a double-stranded RT (dsDNA) to the CRISPR nucleic acid. (D) Covalent association of a double stranded RT (dsDNA) to the CRISPR nucleic acid.

SEQUENCE LISTING FREE TEXT

Figure 1A:
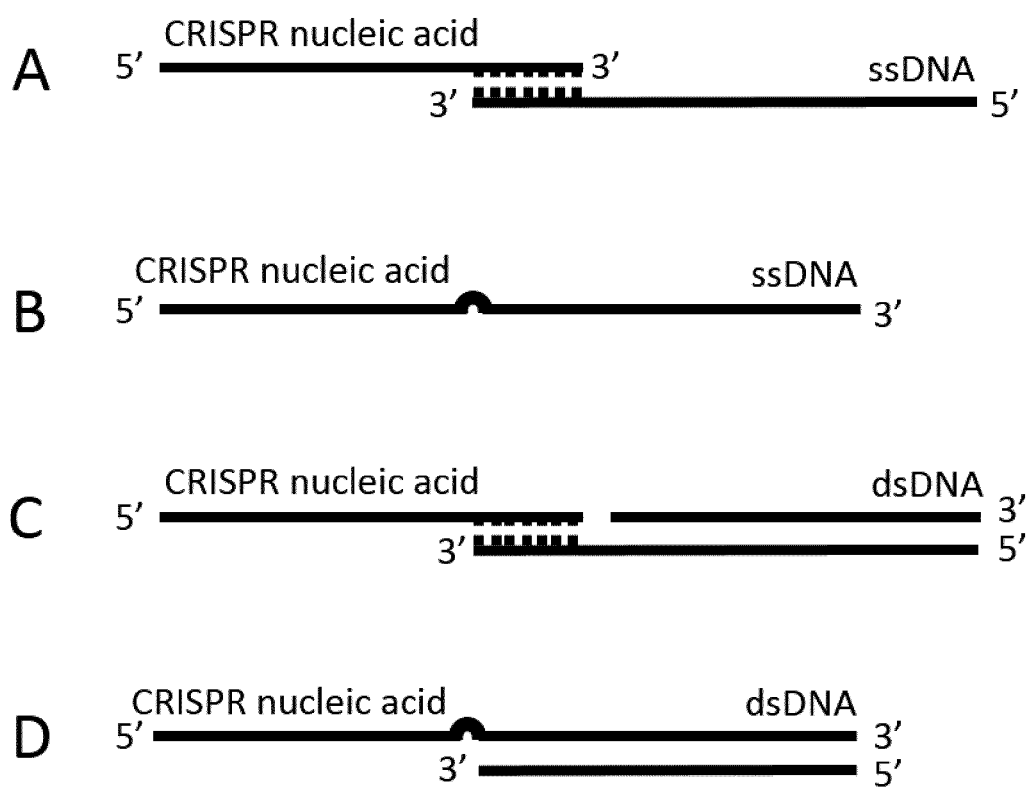
FIG. 1a A to D (FIG. 1a A to D) shows non limiting examples of possible configurations and different ways of association for different RNA-DNA hybrid nucleic acid sequences according to the present invention.

SEQ ID NO:1 discloses a nuclear localization sequence/signal (NLS) of the SV40 large T-antigen
SEQ ID NO:2 discloses a nucleoplasmin bipartite NLS
SEQ ID NO:3 discloses a c-myc NLS.
SEQ ID NO:4 discloses a further c-myc NLS.
SEQ ID NO:5 discloses a hRNPA1 M9 NLS.
SEQ ID NO:6 discloses a IBB domain from importin-alpha.
SEQ ID NO:7 discloses a sequence derived from myoma T protein.
SEQ ID NO:8 discloses a further sequence derived from myoma T protein.
SEQ ID NO:9 discloses a sequence derived from human p53.
SEQ ID NO:10 discloses a sequence derived from mouse c-abl IV.
SEQ ID NO:11 discloses a sequence derived from influenza virus NS1.
SEQ ID NO:12 discloses a further sequence derived from influenza virus NS1.
SEQ ID NO:13 discloses a sequence derived from Hepatitis virus delta antigen.
SEQ ID NO:14 discloses a sequence derived from mouse Mx1 protein.
SEQ ID NO:15 discloses a sequence derived from human poly(ADP-ribose) polymerase.
SEQ ID NO:16 discloses a sequence derived from steroid hormone receptors (human) glucocorticoid.
SEQ ID NO:17 discloses a sequence derived from HIV Tat.
SEQ ID NO:18 discloses a further sequence derived from HIV Tat.

Definitions

The terms "guide RNA", "gRNA" or "single guide RNA" or "sgRNA" are used interchangeably herein and either refer to a synthetic fusion of a CRISPR RNA (crRNA) and a trans-activating crRNA (tracrRNA), or the term refers to a single RNA molecule consisting only of a crRNA and/or a tracrRNA, or the term refers to a gRNA individually comprising a crRNA or a tracrRNA moiety. A tracr and a crRNA moiety, if present as required by the respective CRISPR polypeptide, thus do not necessarily have to be present on one covalently attached RNA molecule, yet they can also be comprised by two individual RNA molecules, which can associate or can be associated by non-covalent or covalent interaction to provide a gRNA according to the present disclosure. In the case of single RNA-guided endonucleases like Cpf1 (see Zetsche et al., 2015, supra), for example, a crRNA as single guide nucleic acid sequence might be sufficient for mediating DNA targeting.

The terms "guide nucleic acid (sequence)" and "CRISPR nucleic acid (sequence)" are used interchangeably herein and describe a nucleic acid sequence, which can specifically interact with a CRISPR polypeptide, and which comprises at least one RNA portion.

The terms "genome editing", "gene editing" and "genome engineering" are used interchangeably herein and refer to strategies and techniques for the targeted, specific modification of any genetic information or genome of a living organism. As such, the terms comprise gene editing, but also the editing of regions other than gene encoding regions of a genome. It further comprises the editing or engineering of the nuclear (if present) as well as other genetic information of a cell. Furthermore, the terms "genome editing" and "genome engineering" also comprise an epigenetic editing or engineering, i.e. the targeted modification of, e.g. methylation, histone modification or of non-coding RNAs possibly causing heritable changes in gene expression.

The terms "CRISPR polypeptide", "CRISPR endonuclease", CRISPR nuclease", "CRISPR protein", "CRISPR effector" or "CRISPR enzyme" are used interchangeably herein and refer to any naturally occurring or artificial amino acid sequence, or the nucleic acid sequence encoding the same, acting as site-specific DNA nuclease or nickase, wherein the "CRISPR polypeptide" is derived from a CRISPR system of any organism, which can be cloned and used for targeted genome engineering. The term "CRISPR polypeptide" also comprises mutants or catalytically active fragments or fusions of a naturally occurring CRISPR effector sequence. A "CRISPR polypeptide" may thus, for example, also refer to a CRISPR nickase or even a nuclease-deficient variant of a CRISPR polypeptide having endonucleolytic function in its natural environment.

The terms "nucleotide" and "nucleic acid" with reference to a sequence or a molecule are used interchangeably herein and refer to a single or double-stranded DNA or RNA of natural or synthetic origin. The term nucleotide sequence is thus used for any DNA or RNA sequence independent of its length, so that the term comprises any nucleotide sequence comprising at least one nucleotide, but also any kind of larger oligonucleotide or polynucleotide. The term(s) thus refer to natural and/or synthetic deoxyribonucleic acids (DNA) and/or ribonucleic acid (RNA) sequences, which can optionally comprise synthetic nucleic acid analoga. A nucleic acid according to the present disclosure can optionally be codon optimized. Codon optimization implies that the codon usage of a DNA or RNA is adapted to that of a cell or organism of interest to improve the transcription rate of said recombinant nucleic acid in the cell or organism of interest. The skilled person is well aware of the fact that a target nucleic acid can be modified at one position due to the codon degeneracy, whereas this modification will still lead to the same amino acid sequence at that position after translation, which is achieved by codon optimization to take into consideration the species-specific codon usage of a target cell or organism. Nucleic acid sequences according to the present application can carry specific codon optimization for the following non limiting list of organisms: *Hordeum vulgare, Sorghum bicolor, Secale cereale, Triticale, Saccharum officinarium, Zea mays, Setaria italic, Oryza sativa, Oryza minuta, Oryza australiensis, Oryza alta, Triticum aestivum, Triticum durum, Triticale, Hordeum bulbosum, Brachypodium distachyon, Hordeum marinum, Aegilops tauschii, Malus domestica, Beta vulgaris, Helianthus annuus, Daucus glochidiatus, Daucus pusillus, Daucus muricatus, Daucus carota, Eucalyptus grandis, Erythranthe guttata, Genlisea aurea, Nicotiana sylvestris, Nicotiana* tabacum, Nicotiana tomentosiformis, Nicotiana benthamiana, Solanum lycopersicum, Solanum tuberosum, Coffea canephora, Vitis vinifera, Cucumis sativus, Morus notabilis, Arabidopsis thaliana, Arabidopsis lyrata, Arabidopsis arenosa, Crucihimalaya himalaica, Crucihimalaya wallichii, Cardamine flexuosa, Lepidium virginicum, Capsella bursa-pastoris, Olmarabidopsis pumila, Arabis hirsuta, Brassica napus, Brassica oleracea, Brassica rapa, Brassica juncacea, Brassica nigra, Raphanus sativus, Eruca vesicaria sativa, Citrus sinensis, Jatropha curcas, Glycine max, Gossypium ssp., Populus trichocarpa, Mus musculus, Rattus norvegicus or Homo sapiens.

The term "delivery construct" or "delivery vector" as used herein refers to any biological or chemical means used as a cargo for transporting a nucleic acid, including a hybrid nucleic acid comprising RNA and DNA, and/or an amino acid sequence of interest into a target cell, preferably a eukaryotic cell. The term delivery construct or vector as used herein thus refers to a means of transport to deliver a genetic or a recombinant construct according to the present disclosure into a target cell, tissue, organ or an organism. A vector can thus comprises nucleic acid sequences, optionally comprising sequences like regulatory sequences or localization sequences for delivery, either directly or indirectly, into a target cell of interest or into a plant target structure in the desired cellular compartment of a plant. A vector can also be used to introduce an amino acid sequence or a ribonucleomolecular complex into a target cell or target structure. Usually, a vector as used herein can be a plasmid vector. Furthermore, according to certain preferred embodiments according to the present invention, a direct introduction of a construct or sequence or complex of interest is conducted. The term direct introduction implies that the desired target cell or target structure containing a DNA target sequence to be modified according to the present disclosure is directly transformed or transduced or transfected into the specific target cell of interest, where the material delivered with the delivery vector will exert its effect. The term indirect introduction implies that the introduction is achieved into a structure, for example, cells of leaves or cells of organs or tissues, which do not themselves represent the actual target cell or structure of interest to be transformed, but those structures serve as basis for the systemic spread and transfer of the vector, preferably comprising a genetic construct according to the present disclosure to the actual target structure, for example, a meristematic cell or tissue, or a stem cell or tissue. In case the term vector is used in the context of transfecting amino acid sequences and/or nucleic sequences, including hybrid nucleic acid sequences, into a target cell the term vector implies suitable agents for peptide or protein transfection, like for example ionic lipid mixtures, cell penetrating peptides (CPPs), or particle bombardment. In the context of the introduction of nucleic acid material, the term vector cannot only imply plasmid vectors but also suitable carrier materials which can serve as basis for the introduction of nucleic acid and/or amino acid sequence delivery into a target cell of interest, for example by means of particle bombardment. Said carrier material comprises, inter alia, gold or tungsten particles. Finally, the term vector also implies the use of viral vectors for the introduction of at least one genetic construct according to the present disclosure like, for example, modified viruses for example derived from the following virus strains: adenoviral or adeno-associated viral (AAV) vectors, lentiviral vectors, herpes simplex virus (HSV-1), vaccinia virus, Sendai virus, Sindbis virus, Semliki forest alphaviruses, Epstein-Barr-Virus (EBV), *Maize* Streak Virus (MSV), Barley Stripe Mosaic Virus (BSMV), Brome Mosaic virus (BMV, accession numbers: RNA1: X58456; RNA2: X58457; RNA3: X58458), *Maize* stripe virus (MSpV), *Maize* rayado fino virus (MYDV), *Maize* yellow dwarf virus (MYDV), *Maize dwarf* mosaic virus (MDMV), positive strand RNA viruses of the family Benyviridae, e.g. Beet necrotic yellow vein virus (accession numbers: RNA1: NC_003514; RNA2: NC_003515; RNA3: NC_003516; RNA4: NC_003517) or of the family Bromoviridae, e.g. viruses of the genus *Alfalfa mosaic* virus (accession numbers: RNA1: NC_001495; RNA2: NC_002024; RNA3: NC_002025) or of the genus *Bromovirus*, e.g. BMV (supra), or of the genus *Cucumovirus*, e.g. *Cucumber mosaic* virus (accession numbers: RNA1: NC_002034; RNA2: NC_002035; RNA3: NC_001440), or of the genus *Oleavirus*, dsDNA viruses of the family Caulimoviridae, particularly of the family Badnavirus or Caulimovirus, e.g. different *Banana streak* viruses (e.g. accession numbers: NC_007002, NC_015507, NC_006955 or NC_003381) or *Cauliflower mosaic* virus (accession number: NC_001497), or viruses of the genus *Cavemovirus, Petuvirus, Rosadnavirus, Solendovirus, Soymovirus* or *Tungrovirus*, positive strand RNA viruses of the family Closteroviridae, e.g. of the genus *Ampelovirus, Crinivirus*, e.g. Lettuce infectious yellows virus (accession numbers: RNA1: NC_003617; RNA2: NC_003618) or Tomato chlorosis virus (accession numbers: RNA1: NC_007340; RNA2: NC_007341), *Closterovirus*, e.g. Beet yellows virus (accession number: NC_001598), or *Velarivirus*, single stranded DNA (+/−) viruses of the family Geminiviridae, e.g. viruses of the family Becurtovirus, Begomovirus, e.g. Bean golden yellow mosaic virus, Tobacco curly shoot virus, Tobacco mottle leaf curl virus, Tomato chlorotic mottle virus, Tomato dwarf leaf virus, Tomato golden mosaic virus, Tomato leaf curl virus, Tomato mottle virus, oder Tomato yellow spot virus, or Geminiviridae of the genus *Curtovirus*, e.g. Beet curly top virus, or Geminiviridae of the genus *Topocuvirus, Turncurtvirus* or *Mastrevirus*, z.B *Maize* streak virus (supra), Tobacco yellow dwarf virus, Wheat dwarf virus, positive strand RNA viruses of the family Luteoviridae, e.g. of the genus *Luteovirus*, e.g. Barley yellow dwarf virus-PAV (accession number: NC_004750), or of the genus *Polerovirus*, e.g. Potato leafroll virus (accession number: NC_001747), single stranded DNA viruses of the family Nanoviridae, comprising the genus *Nanovirus* or *Babuvirus*, double stranded RNA viruses of the family Partiviridae, comprising inter alia the families Alphapartitivirus, Betapartitivirus or Deltapartitivirus, viroids of the family Pospiviroidae, positive strand RNA viruses of the family Potyviridae, e.g. comprising the genus *Brambyvirus, Bymovirus, Ipomovirus, Macluravirus, Poacevirus*, e.g. *Triticum* mosaic virus (accession number: NC_012799), or Potyviridae of the genus *Potyvirus*, e.g. Beet mosaic virus (accession number: NC_005304), *Maize dwarf* mosaic virus (accession number: NC_003377), Potato virus Y (accession number: NC_001616), or *Zea* mosaic virus (accession number: NC_018833), or Potyviridae of the genus *Tritimovirus*, e.g. Brome streak mosaic virus (accession number: NC_003501) or Wheat streak mosaic virus (accession number: NC_001886), single stranded RNA viruses of the family Pseudoviridae, e.g. of the genus *Pseudovirus*, or *Sirevirus*, double stranded RNA viruses of the family Reoviridae, e.g. Rice dwarf virus (accession numbers: RNA1: NC_003773; RNA2: NC_003774; RNA3: NC_003772; RNA4: NC_003761; RNA5: NC_003762; RNA6: NC_003763; RNA7: NC_003760; RNA8: NC_003764; RNA9: NC_003765; RNA10: NC_003766; RNA11: NC_003767; RNA12: NC_003768), positive strand RNA viruses of the family Tombusviridae, e.g. comprising the genus *Alphanecrovirus, Aureusvirus, Betanecrovirus, Carmovirus, Dianthovirus, Gallantivirus, Macanavirus, Machlomovirus, Panicovirus, Tombusvirus, Umbravirus oder Zeavirus*, e.g. Maize necrotic streak virus (accession number: NC_007729), or positive strand RNA viruses of the family Virgaviridae, e.g. viruses of the genus *Furovirus, Hordeivirus*, e.g. Barley stripe mosaic virus (accession numbers: RNA1: NC_003469; RNA2: NC_003481; RNA3: NC_003478), or of the genus *Pecluvirus, Pomovirus, Tobamovirus oder Tobravirus*, e.g. Tobacco rattle virus (accession numbers: RNA1: NC_003805; RNA2: NC_003811), as well as negative strand RNA viruses of the order Mononegavirales, particularly of the family Rhabdoviridae, e.g. Barley yellow striate mosaic virus (accession number: KM213865) or Lettuce necrotic yellows virus (accession number/specimen: NC_007642/AJ867584), positive strand RNA viruses of the order Picornavirales, particularly of the family Secoviridae, e.g. of the genus *Comovirus, Fabavirus, Nepovirus, Cheravirus, Sadwavirus, Sequivirus, Torradovirus*, or *Waikavirus*, positive strand RNA viruses of the order Tymovirales, particularly of the family Alphaflexiviridae, e.g. viruses of the genus *Allexivirus, Lolavirus, Mandarivirus*, or *Potexvirus, Tymovirales*, particularly of the family Betaflexiviridae, e.g. viruses of the genus *Capillovirus, Carlavirus, Citrivirus, Foveavirus, Tepovirus*, or *Vitivirus*, positive strand RNA viruses of the order Tymovirales, particularly of the family Tymoviridae, e.g. viruses of the order Maculavirus, Marafivirus, or Tymovirus, and bacterial vectors, like for example *Agrobacterium* spp., like for example *Agrobacterium tumefaciens*. Finally, the term vector also implies suitable chemical transport agents for introducing linear nucleic acid sequences (single or double-stranded) into a target cell combined with a physical introduction method, including polymeric or lipid-based delivery constructs.

Suitable delivery constructs or vectors thus comprise biological means for delivering nucleotide sequences into a target cell, including viral vectors, *Agrobacterium* spp., or chemical delivery constructs, including nanoparticles, e.g. mesoporous silica nanoparticles (MSNPs), nanocrystals, cationic polymers, including PEI (polyethylenimine) polymer based approaches or polymers like DEAE-dextran, or non-covalent surface attachment of PEI to generate cationic surfaces, lipid or polymeric vesicles, or combinations thereof. Lipid or polymeric vesicles may be selected, for example, from lipids, liposomes, lipid encapsulation systems, nanoparticles, small nucleic acid-lipid particle formulations, polymers, and polymersomes.

The terms "genetic construct" or "recombinant construct" are used herein to refer to a construct comprising, inter alia, plasmids or plasmid vectors, cosmids, artificial yeast- or bacterial artificial chromosomes (YACs and BACs), phagemides, bacterial phage based vectors, an expression cassette, isolated single-stranded or double-stranded nucleic acid sequences, comprising DNA and RNA sequences, or amino acid sequences, viral vectors, including modified viruses, and a combination or a mixture thereof, for introduction or transformation, transfection or transduction into any prokaryotic or eukaryotic target cell, including a plant, plant cell, tissue, organ or material according to the present disclosure. A recombinant construct according to the present disclosure can comprise an effector domain, either in the form of a nucleic acid or an amino acid sequence, wherein an effector domain represents a molecule, which can exert an effect in a target cell and includes a transgene, an single-stranded or double-stranded RNA molecule, including a guide RNA ((s)gRNA), a miRNA or an sRNA, or an amino acid sequences, including, inter alia, an enzyme or a catalytically active fragment thereof, a binding protein, an antibody, a transcription factor, a nuclease, preferably a site specific nuclease, and the like. Furthermore, the recombinant construct can comprise regulatory sequences and/or localization sequences. The recombinant construct can be integrated into a vector, including a plasmid vector, and/or it can be present isolated from a vector structure, for example, in the form of a polypeptide sequence or as a non-vector connected single-stranded or double-stranded nucleic acid. After its introduction, e.g. by transformation, the genetic construct can either persist extrachromosomally, i.e. non integrated into the genome of the target cell, for example in the form of a double-stranded or single-stranded DNA, a double-stranded or single-stranded RNA or as an amino acid sequence. Alternatively, the genetic construct, or parts thereof, according to the present disclosure can be stably integrated into the genome of a target cell, including the nuclear genome or further genetic elements of a target cell, including the genome of plastids like mitochondria or chloroplasts. The term plasmid vector as used in this connection refers to a genetic construct originally obtained from a plasmid. A plasmid usually refers to a circular autonomously replicating extrachromosomal element in the form of a double-stranded nucleic acid sequence. In the field of genetic engineering these plasmids are routinely subjected to targeted modifications by inserting, for example, genes encoding a resistance against an antibiotic or an herbicide, a gene encoding a target nucleic acid sequence, a localization sequence, a regulatory sequence, a tag sequence, a marker gene, including an antibiotic marker or a fluorescent marker, and the like. The structural components of the original plasmid, like the origin of replication, are maintained. According to certain embodiments of the present invention, the localization sequence can comprise a nuclear localization sequence, a plastid localization sequence, preferably a mitochondrion localization sequence or a chloroplast localization sequence. Said localization sequences are available to the skilled person in the field of plant biotechnology. A variety of plasmid vectors for use in different target cells of interest is commercially available and the modification thereof is known to the skilled person in the respective field.

The term "genetically modified" or "genetic manipulation" or "genetic(ally) manipulated" is used in a broad sense herein and means any modification of a nucleic acid sequence or an amino acid sequence, a target cell, tissue, organ or organism, which is accomplished by human intervention, either directly or indirectly, to influence the endogenous genetic material or the transcriptome or the proteome of a target cell, tissue, organ or organism to modify it in a purposive way so that it differs from its state as found without human intervention, whereas the term genome editing specifically refers to a targeted manipulation of the genome of a target cell. The human intervention can either take place in vitro or in vivo, or both. Further modifications can be included, for example, one or more point mutation(s), e.g. for targeted protein engineering or for codon optimization, deletion(s), and one or more insertion(s) or deletion(s) of at least one nucleic acid or amino acid molecule (including also homologous recombination), modification of a nucleic acid or an amino acid sequence, or a combination thereof. The terms shall also comprise a nucleic acid molecule or an amino acid molecule or a host cell or an organism, including a plant or a plant material thereof which is/are similar to a comparable sequence, organism or material as occurring in nature, but which have been constructed by at least one step of purposive manipulation.

A "targeted genetic manipulation" or "targeted" or "site-directed" gene editing or genome editing as used herein is thus the result of a "genetic manipulation", which is effected in a targeted way, i.e. at least one specific position in a target cell and under the specific suitable circumstances to achieve a desired effect in at least one cell, preferably a plant cell, to be manipulated.

The terms "transgene" or "transgenic" as used herein refer to at least one nucleic acid sequence that is taken from the genome of one organism, or produced synthetically, and which is then introduced into a host cell or organism or tissue of interest and which is subsequently integrated into the host's genome by means of "stable" transformation or transfection approaches. In contrast, the term "transient" transformation or transfection or introduction refers to a way of introducing molecular tools including at least one nucleic acid (DNA, RNA, single-stranded or double-stranded or a mixture thereof) and/or at least one amino acid sequence, optionally comprising suitable chemical or biological agents, to achieve a transfer into at least one compartment of interest of a cell, including, but not restricted to, the cytoplasm, an organelle, including the nucleus, a mitochondrion, a vacuole, a chloroplast, or into a membrane, resulting in transcription and/or translation and/or association and/or activity of the at least one molecule introduced without achieving a stable integration or incorporation and thus inheritance of the respective at least one molecule introduced into the genome of a cell.

The term "plant" or "plant cell" as used herein refers to a plant organism, a plant organ, differentiated and undifferentiated plant tissues, plant cells, seeds, and derivatives and progeny thereof. Plant cells include without limitation, for example, cells from seeds, from mature and immature embryos, meristematic tissues, seedlings, callus tissues in different differentiation states, leaves, flowers, roots, shoots, gametophytes, sporophytes, pollen, pollen tubes and microspores, protoplasts, macroalgae and microalgae. The different plant cells can either be haploid, diploid, tetraploid, hexaploid or polyploid.

"Subject", as used herein, may mean either a human or non-human animal. The term includes, but is not limited to, mammals (e.g., humans, other primates, pigs, rodents (e.g., mice and rats or hamsters), rabbits, guinea pigs, cows, horses, cats, dogs, sheep, and goats). In an embodiment, the subject is a human being.

"Treat", "treating" and "treatment", as used herein, generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease or symptom in a mammal, and includes: (a) preventing the disease or symptom from occurring in a subject which may be predisposed to acquiring the disease or symptom but has not yet been diagnosed as having it; (b) inhibiting the disease or symptom, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease.

A "plant material" as used herein refers to any material which can be obtained from a plant during any developmental stage. The plant material can be obtained either in planta or from an in vitro culture of the plant or a plant tissue or organ thereof. The term thus comprises plant cells, tissues and organs as well as developed plant structures as well as sub-cellular components like nucleic acids, polypeptides and all chemical plant substances or metabolites which can be found within a plant cell or compartment and/or which can be produced by the plant, or which can be obtained from an extract of any plant cell, tissue or a plant in any developmental stage. The term also comprises a derivative of the plant material, e.g. a protoplast, derived from at least one plant cell comprised by the plant material. The term therefore also comprises meristematic cells or a meristematic tissue of a plant.

As used herein, the terms "mutation" and "modification" are used interchangeably to refer to a deletion, insertion, addition, substitution, edit, strand break, and/or introduction of an adduct in the context of nucleic acid manipulation in vivo or in vitro. A deletion is defined as a change in a nucleic acid sequence in which one or more nucleotides is absent. An insertion or addition is that change in a nucleic acid sequence which has resulted in the addition of one or more nucleotides. A "substitution" or edit results from the replacement of one or more nucleotides by a molecule which is a different molecule from the replaced one or more nucleotides. For example, a nucleic acid may be replaced by a different nucleic acid as exemplified by replacement of a thymine by a cytosine, adenine, guanine, or uridine. Pyrimidine to pyrimidine (e.g. C to T or T to C nucleotide substitutions) or purine to purine (e.g. G to A or A to G nucleotide substitutions) are termed transitions, whereas pyrimidine to purine or purine to pyrimidine (e.g. G to T or G to C or A to T or A to C) are termed transversions. Alternatively, a nucleic acid may be replaced by a modified nucleic acid as exemplified by replacement of a thymine by thymine glycol. Mutations may result in a mismatch. The term mismatch refers to a non-covalent interaction between two nucleic acids, each nucleic acid residing on a different nucleotide sequence or nucleic acid molecule, which does not follow the base-pairing rules. For example, for the partially complementary sequences 5'-AGT-3' and 5'-AAT-3', a G-A mismatch (a transition) is present.

The term "strand break" when made in reference to a double-stranded nucleic acid sequence, e.g. a genomic sequence as DNA target sequence, includes a single-strand break and/or a double-strand break. A single-strand break (a nick) refers to an interruption in one of the two strands of the double-stranded nucleic acid sequence. This is in contrast to a double-strand break which refers to an interruption in both strands of the double-stranded nucleic acid sequence. Strand breaks according to the present disclosure may be introduced into a double-stranded nucleic acid sequence by enzymatic incision at a nucleic acid base position of interest using a suitable endonuclease, including a CRISPR endonuclease or a variant thereof, where the variant can be a mutated or truncated version of the wild-type protein or endonuclease, which still can exert the enzymatic function of the wild-type protein.

"Complementary" or "complementarity" as used herein describes the relationship between two DNA, two RNA, or, regarding hybrid sequences according to the present invention, between an RNA and a DNA nucleic acid region. Defined by the nucleobases of the DNA or RNA, two nucleic acid regions can hybridize to each other in accordance with the lock-and-key model. To this end the principles of Watson-Crick base pairing have the basis adenine and thymine/uracil as well as guanine and cytosine, respectively, as complementary bases apply. Furthermore, also non-Watson-Crick pairing, like reverse-Watson-Crick, Hoogsteen, reverse-Hoogsteen and Wobble pairing are comprised by the term "complementary" as used herein as long as the respective base pairs can build hydrogen bonding to each other, i.e. two different nucleic acid strands can hybridize to each other based on said complementarity.

The term "transient introduction" as used herein refers to the transient introduction of at least one nucleic acid sequence according to the present disclosure, preferably incorporated into a delivery vector or into a recombinant construct, with or without the help of a delivery vector, into a target structure, for example, a plant cell, wherein the at least one nucleic acid sequence is introduced under suitable reaction conditions so that no integration of the at least one nucleic acid sequence into the endogenous nucleic acid material of a target structure, the genome as a whole, occurs, so that the at least one nucleic acid sequence will not be integrated into the endogenous DNA of the target cell. As a consequence, in the case of transient introduction, the introduced genetic construct will not be inherited to a progeny of the target structure, for example a prokaryotic, an animal or a plant cell. The at least one nucleic acid sequence or the products resulting from transcription or translation thereof are only present temporarily, i.e. in a transient way, in constitutive or inducible form, and thus can only be active in the target cell for exerting their effect for a limited time. Therefore, the at least one nucleic acid sequence introduced via transient introduction will not be heritable to the progeny of a cell. The effect which a nucleic acid sequence introduced in a transient way can, however, potentially be inherited to the progeny of the target cell.

The term "stable integration" or "stably integrated" as used herein, refers to the stable integration of at least one nucleic acid sequence according to the present disclosure, preferably incorporated into a delivery vector or into a recombinant construct. The integration can either take place into the nuclear genome of a target cell or any other genomic extra-nuclear material within a eukaryotic cell compartment of interest, e.g. a mitochondrium or a plant cell plastid. A stably integrated at least one recombinant construct will thus be heritable to the progeny of a thus modified target cell. Depending on the nature of the genetic construct, all or part of the genetic construct will be stably integrated, as the genetic construct may comprise several regions of interest comprising a target region to be stably integrated as well as further regions, inter alia, needed for the transport, delivery, maintenance, and the correct localization of the genetic construct within a plant cell, which regions, however, will not themselves be integrated, but serve as cargo for the region of interest to be stably integrated as it is known to the skilled person.

The stable integration of at least one genetic construct according to the present disclosure into at least one hematopoietic or meristematic cell or tissue will consequently lead to the inheritance of the thus modified genomic region of the target structure, i.e. a DNA target region, to the progeny of the modified cell through all developmental stages of said at least one hematopoietic or meristematic cell, which can be favorable for approaches, where a targeted genetic modification in and the yield of the final cell type resulting from the differentiation and development of the at least one hematopoietic meristematic cell is desired.

Achieving, for example, a stable integration into at least one meristematic cell of the immature inflorescence of a plant can thus lead to the stable inheritance of the introduced genetic feature into the gamete of the pollen or of the ovule developmentally resulting from the at least one meristematic cell of the immature inflorescence. Stable integration into at least one pluripotent hematopoietic cell or any pluripotent or multipotent cell will likewise lead to stable inheritance of the introduced genetic feature.

The term "particle bombardment" as used herein, also named biolistic transfection or microparticle-mediated gene transfer, refers to a physical delivery method for transferring a coated microparticle or nanoparticle comprising a nucleic acid or a genetic construct of interest into a target cell or tissue. The micro- or nanoparticle functions as projectile and is fired on the target structure of interest under high pressure using a suitable device, often called "gene-gun". The transformation via particle bombardment uses a microprojectile of metal covered with the gene of interest, which is then shot onto the target cells using an equipment known as "gene-gun" (Sandford et al. 1987) at high velocity fast enough to penetrate the cell wall of a target tissue, but not harsh enough to cause cell death. For protoplasts, which have their cell wall entirely removed, the conditions are different logically. The precipitated nucleic acid or the genetic construct on the at least one microprojectile is released into the cell after bombardment, and integrated into the genome or expressed transiently according to the definition given above. The acceleration of microprojectiles is accomplished by a high voltage electrical discharge or compressed gas (helium). Concerning the metal particles used it is mandatory that they are non-toxic, non-reactive, and that they have a smaller diameter than the target cell. The most commonly used are gold or tungsten. There is plenty of information publicly available from the manufacturers and providers of gene-guns and associated system concerning their general use.

The term "derivative" or "descendant" or "progeny" as used herein in the context of a prokaryotic or a eukaryotic cell, preferably an animal cell and more preferably a plant or plant cell or plant material according to the present disclosure relates to the descendants of such a cell or material which result from natural reproductive propagation including sexual and asexual propagation. It is well known to the person having skill in the art that said propagation can lead to the introduction of mutations into the genome of an organism resulting from natural phenomena which results in a descendant or progeny, which is genomically different to the parental organism or cell, however, still belongs to the same genus/species and possesses mostly the same characteristics as the parental recombinant host cell. Such derivatives or descendants or progeny resulting from natural phenomena during reproduction or regeneration are thus comprised by the term of the present disclosure. Furthermore, the term "derivative" can imply, in the context of a substance or molecule rather than referring to a cell or organism, directly or by means of modification indirectly obtained from another. This might imply a nucleic acid sequence derived from a cell or a plant metabolite obtained from a cell or material.

The term "target region", "target site", "target structure", "target construct", "target nucleic acid" or "target cell/tissue/organism", or "DNA target region" as used herein refers to a target which can be any genomic region within any compartment of a target cell.

The term "regulatory sequence" as used herein refers to a nucleic acid or an amino acid sequence, which can direct the transcription and/or translation and/or modification of a nucleic acid sequence of interest.

The terms "protein", "amino acid" or "polypeptide" are used interchangeably herein and refer to an amino acid sequence having a catalytic enzymatic function or a structural or a functional effect. The term "amino acid" or "amino acid sequence" or "amino acid molecule" comprises any natural or chemically synthesized protein, peptide, polypeptide and enzyme or a modified protein, peptide, polypeptide and enzyme, wherein the term "modified" comprises any chemical or enzymatic modification of the protein, peptide, polypeptide and enzyme, including truncations of a wild-type sequence to a shorter, yet still active portion.

DETAILED DESCRIPTION

According to the first aspect of the present invention, there is provided a hybrid nucleic acid sequence comprising or consisting of at least one RNA and at least one DNA nucleic acid sequence, comprising: (a) a CRISPR nucleic acid sequence or a guide nucleic acid sequence, comprising at least one RNA nucleic acid sequence, wherein the CRISPR nucleic acid sequence or the guide nucleic acid sequence comprises (i) a first sequence portion that is complementary to a first DNA target sequence, and (ii) a second sequence portion, wherein the second sequence portion is configured to interact with a CRISPR polypeptide; and comprising associated with the CRISPR nucleic acid sequence or the guide nucleic acid sequence: (b) a repair template nucleic acid sequence, comprising a DNA nucleic acid sequence, wherein the repair template nucleic acid sequence comprises at least one portion being complementary to a second DNA target sequence, and wherein the repair template nucleic acid sequence is configured to mediate targeted homology directed repair; and (c) optionally: a linker region between the CRISPR nucleic acid sequence or the guide nucleic acid sequence and the repair template nucleic acid sequence; wherein the hybrid nucleic acid sequence is capable of interacting with a CRISPR polypeptide so that the CRISPR polypeptide can recognize the first DNA target sequence and optionally induce a DNA break, and wherein the hybrid nucleic acid sequence directs genome engineering through homology directed repair mediated by the repair template nucleic acid sequence at the site of the second DNA target sequence.

Figure 1B:
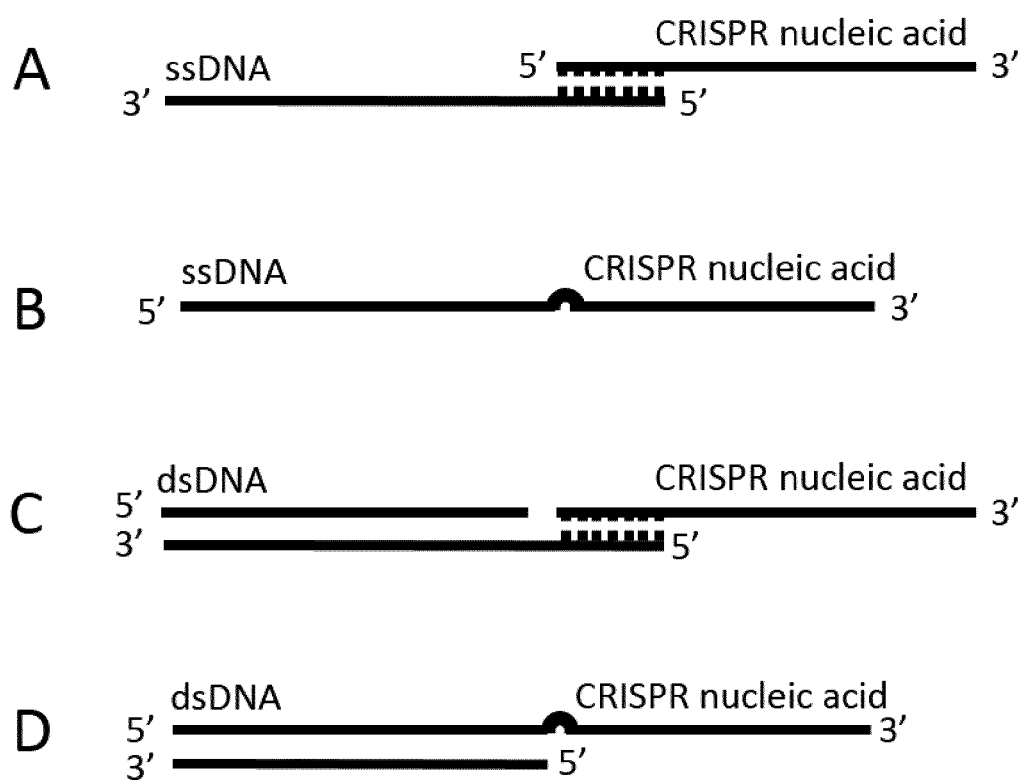
FIG. 1b A to D (FIG. 1b A to D) shows non-limiting examples of further possible configurations and different ways of association for different RNA-DNA hybrid nucleic acid sequences according to the present invention.
Figure 2:
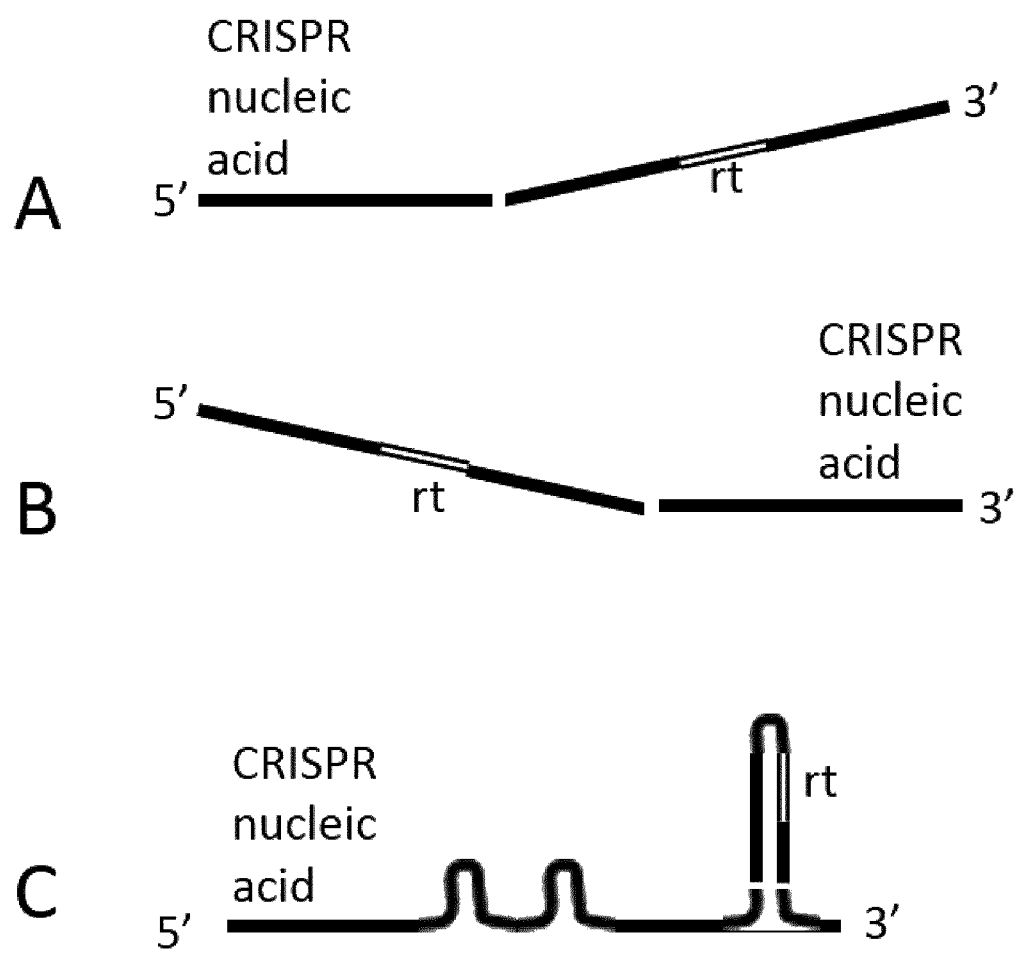
FIG. 2 A to C (FIG. 2 A to C): shows non limiting examples of possible locations at which the RT can be attached to or associated with the CRISPR nucleic acid comprising at least one RNA stretch to form an RNA-DNA hybrid nucleic acid according to the present invention. (A) Covalent or non-covalent association of the single- or double-stranded RT to the 3'-end of the CRISPR nucleic acid, for example, a sgRNA. (B) Covalent or non-covalent association of the single- or double-stranded RT to the 5'-end of the CRISPR nucleic acid, for example, a sgRNA. (D) Covalent or non-covalent association of the single- or double-stranded RT internal to the CRISPR nucleic acid, for example, a sgRNA. The repair template (RT/rt) portion is shown in grey in all Figures.

Suitable configurations for a hybrid nucleic acid sequence according to the present invention are shown in FIG. 1a A to D, FIG. 1b A to D and FIG. 2 A to C, but are not restricted thereto. Depending on the CRISPR nuclease, the repair template (RT) can be in a ssDNA or dsDNA form and can be attached to the at least one CRISPR nucleic acid or guide nucleic acid (sgRNA or gRNA or crRNA or tracrRNA) sequence at the 3'end, the 5'end in a covalent or non-covalent way, or the RT can be positioned within the gRNA, e.g. forming a hairpin secondary structure of a defined size and shape. This design allows that both the RNA and the RT portion can both fulfill their functions without disturbing the interaction of at least one RNA of interest with a CRISPR nuclease of interest and simultaneously positioning the RT in close proximity to the site of a DNA break induced by the at least one CRISPR nuclease/CRISPR RNA pair. Naturally, different CRISPR nucleases suitable for genome engineering will have different sterical requirements concerning the interaction with a CRISPR nucleic acid comprising a RT according to the present invention so that the intrinsic functions of the CRISPR nuclease, i.e., DNA targeting as assisted by the CRISPR nucleic acid and DNA cleavage, can be mediated also in the presence of a hybrid nucleic acid sequence comprising a RT attached to the CRISPR nucleic acid sequence.

A hybrid nucleic acid sequence comprising or consisting of at least one RNA and at least one DNA nucleic acid sequence or simply a hybrid RNA/DNA nucleic acid sequence according to the present invention thus represents a chimeric RNA and DNA comprising molecule, which comprises two functionalities. First, it comprises a CRISPR nucleic acid sequence (gRNA or crRNA or tracrRNA) moiety, comprising a ribonucleic acid. A gRNA usually comprises two nucleotide sequence portions, one nucleotide sequence being necessary for interaction with a CRISPR polypeptide of interest as well as another nucleotide sequence comprising a targeting domain, wherein the targeting domain is able to hybridize via base-pairing to a complementary DNA target sequence of interest adjacent to a PAM sequence in the opposite strand, this complementary DNA target sequence thus representing the first DNA target sequence according to the present invention. Secondly, the hybrid RNA/DNA nucleic acid sequence comprises a repair template nucleic acid sequence moiety which can comprise a desired edit to be introduced into a DNA target sequence of interest. Furthermore, the repair template nucleic acid sequence can comprise additional homologous sequence immediately upstream and downstream of the DNA target sequence, i.e. left and right homology arms. The length and binding position of each homology arm is dependent on the size of the change being introduced, and can be adjusted for optimal efficiency. For example, it is likely that a repair template with complementarity specific for the cleaved DNA strand first released by Cas9 (as described in Richardson, et al., Nature Biotechnology. 2016, doi: 10.1038/nbt.3481) may produce the most efficient repair. The repair template can be a single-stranded or a double-stranded DNA nucleotide sequence depending on the specific application. The repair template may contain polymorphisms relative to the genomic DNA to disrupt binding by the nuclease, otherwise the repair template becomes a suitable target for CRISPR polypeptide cleavage. For example, the PAM could be mutated such that it is no longer present, but the coding region of the gene is not affected, which corresponds to a silent mutation not changing the encoded amino acid sequence. In another embodiment, where a nuclease deficient CRISPR polypeptide is used, the presence of a PAM sequence within the repair template sequence is possible. In one embodiment, the hybrid RNA/DNA nucleic acid sequence comprises at least one CRISPR nucleic acid sequence and at least one repair template nucleic acid sequence, but the hybrid can also comprise further moieties attached thereto suitable for genome editing as further detailed below. In another embodiment the the hybrid RNA/DNA nucleic acid sequence consists of at least one CRISPR nucleic acid sequence and at least one repair template nucleic acid sequence.

It was found that an optimal RT size can exist depending on the CRISPR system used that provides a balance of nuclease efficiency with homology arm size for efficiency of HR-mediated DSB repair.

In one embodiment, the CRISPR nucleic acid sequence may be provided as one RNA nucleic acid sequence unifying a tracrRNA and a crRNA element. In another embodiment, for example when working with a Type V CRISPR system using a Cpf1 polypeptide or a variant or catalytically active fragment thereof, the the gRNA comprises a crRNA element. In yet a further embodiment, the gRNA can be provided as more than one RNA nucleic acid sequence mimicking the natural situation in many CRISPR systems that crRNA and tracrRNA, if both necessary, are provided on two separate RNA molecules. In certain embodiments, this arrangement thus allows for the possibility of having the two elements (tracrRNA and crRNA) in separate RNA strands like in nature. In one embodiment, there is provided a separate RNA nucleic acid molecule providing a crRNA and there is provided a separate RNA nucleic acid molecule. Either the crRNA moiety or the tracrRNA moiety can be associated with a repair template (RT) nucleic acid sequence. For example, providing a tracrRNA:RT hybrid or a crRNA:RT can be preferred when ex vivo chemical synthesis of the tracrRNA:RT or the crRNA:RT is chosen due to the shorter length of the respective molecule in comparison to a gRNA:RT hybrid, wherein the gRNA consists of one single RNA molecule unifying crRNA and tracrRNA function.

In certain embodiments, it may be envisaged that the CRISPR nucleic acid sequence, comprising at least one CRISPR RNA portion, forms the 5' portion of the hybrid nucleic acid sequence. This topology or configuration is illustrated in FIG. 1a.

In another embodiment, it may be envisaged that the RT, comprising at least one single-stranded or double-stranded DNA portion, forms the 5' portion of the hybrid nucleic acid sequence. This topology is illustrated in FIG. 1b.

In yet another embodiment, it might be envisaged that the RT portion is located within the CRISPR nucleic acid as illustrated in FIG. 2. As illustrated in FIG. 2C, the RT may be located on a specific loop region as individual portion within the CRISPR nucleic acid sequence. For providing the CRISPR nucleic acid-RT topologies as shown in FIG. 2, two steps of associating the CRISPR nucleic acid portions to the RT may become necessary to position the RT portion comprising DNA within the CRISPR nucleic acid portion, the CRISPR nucleic acid comprising at least one RNA portion.

Ample chemical and enzymatic methods of linking nucleic acids to each other in addition to exploiting the natural base-pairing capacity are available to the skilled person so that any topology of a hybrid nucleic acid sequence may be provided with presently available technologies. Furthermore, any component of the CRISPR nucleic acid, i.e. the at least one CRISPR nucleic acid and/or the at least one RT, may comprise additional modifications or labels at their free 5' or 3'ends, or attached to any nucleotide within the at least one CRISPR nucleic acid and/or the at least one RT. Said modifications or labels may serve the purpose of providing functional groups to link a CRISPR nucleic acid and/or a RT to each other. In another embodiment, the modification or label may serve the purpose of providing an additional functionality to the RT and/or the CRISPR nucleic acid and thus the associated hybrid nucleic acid according the present invention, for example, a fluorescence functionality, which allows the visualization and/or tracking of the individual component, or the hybrid nucleic acid sequence, or even the molecular complex between the hybrid nucleic sequence and a CRISPR polypeptide of interest within a target cell of interest. This may allow the visualization of specific compartments, or the testing for the availability of the complex in vivo and the like.

The optimum topology of the CRISPR nucleic acid and the RT within the hybrid nucleic acid sequence according to the present invention may depend on the CRISPR polypeptide and the corresponding CRISPR nucleic acid sequence of interest and the target cell to be modified of interest. In one embodiment, for example, when a sgRNA is used, a 5'CRISPR nucleic acid sequence-3'FIT topology may be preferred, as this topology leaves the 3'-RT end unbound and flexible so that the RT portion can assist in homology searching to guarantee best results in a targeted HDR event. This topology may also be suitable, when the use of a CRISPR polypeptide, for example, Cpf1, is envisaged, which may function without the need of a tracrRNA.

For certain bulky and sterically demanding modifications or labels to be introduced at the free 5' and 3'ends of the hybrid nucleic acid sequence, a 5'RT-3'CRISPR nucleic acid sequence topology may be preferred to allow optimum performance of the CRISPR polypeptide in complex with the hybrid nucleic acid sequence of interest. Furthermore, independent of any additional 5' or 3 modifications or labels, a 5'RT-3'CRISPR nucleic acid sequence topology may be preferred for certain CRISPR polypeptides due to their intrinsic interaction properties with the cognate CRISPR nucleic acid.

Furthermore, the topology of the hybrid nucleic acid sequence may depend on the CRISPR nucleic acid sequences used. crRNA/tracrRNA combinations may have different needs than the use of only a crRNA. Likewise, a sgRNA fusion of crRNA and tracrRNA may allow other configurations within a hybrid nucleic acid sequence according to the present invention as it is the case for CRISPR nucleic acid portions, wherein a crRNA and a tracrRNA portion are hybridized and not covalently fused to each other. Based on the different hybrid nucleic acid sequences disclosed herein and based on tests of these constructs having different topologies with respect to the positioning of the CRISPR nucleic acid portion and the RT portion, the skilled person can determine the best topology of a hybrid nucleic acid construct according to the present invention for a CRISPR polypeptide, a CRISPR nucleic acid sequence, a RT and thus a target locus of interest to be modified.

The hybrid nucleic acid sequence according to the present invention is thus suitable for precision genome editing in any cell type of interest, including prokaryotic cells and eukaryotic cells, including fungal, animal and plant cells and represents a suitable physically connected tool to allow simultaneous spatiotemporal availability of a repair template and a CRISPR RNA during genome editing.

According to all aspects and embodiments of the present invention, the CRISPR nucleic acid sequence and the repair template nucleic acid sequence are associated with each other. The term "associated with" or "in association" according to the present disclosure is to be construed broadly and, therefore, according to present invention it implies that a CRISPR compatible RNA is provided in physical association with a DNA repair template, the association being either of covalent or non-covalent nature, inherently increasing the availability of the repair template for homologous recombination. Instead of indiscriminate amplification of the repair template, or provision of the repair template in excess, yet physically unlinked to the RNA, the repair template nucleotide sequence is thus presented at the DSB together with the CRISPR nuclease complex guided by the RNA to a DNA target sequence of interest, which in turn significantly improves the predictability and the specificity of a genome editing approach.

In a further embodiment according to the present invention, at least one repair template nucleic acid sequence is attached to at least one CRISPR nucleic acid sequence by way of both covalent and/or non-covalent bonds or attachments. According to this embodiment, the hybrid RNA/DNA complex can be provided as in vitro synthesized nucleotide molecule which can then be associated with a CRISPR polypeptide of interest, either in vitro, or in vivo in the target cell of interest comprising a first and a second DNA target sequence within its genome. Preferably, the cell is a eukaryotic cell, including a fugal, an animal or a plant cell.

In one embodiment according to the various aspects of the present invention at least one repair template nucleic acid sequence (RT) is covalently attached to at least one CRISPR nucleic acid sequence. A covalent attachment or covalent bond is a chemical bond that involves the sharing of electron pairs between atoms of the molecules or sequences covalently attached to each other.

In another embodiment according to the various aspects of the present invention at least one repair template nucleic acid sequence is non-covalently attached to at least one CRISPR nucleic acid sequence. A non-covalent interaction differs from a covalent bond in that it does not involve the sharing of electrons, but rather involves more dispersed variations of electromagnetic interactions between molecules/sequences or within a molecule/sequence. Non-covalent interactions or attachments thus comprise electrostatic interactions, van der Waals forces, π-effects and hydrophobic effects. Of special importance in the context of nucleic acid molecules are hydrogen bonds as electrostatic interaction. A hydrogen bond (H-bond) is a specific type of dipole-dipole interaction that involves the interaction between a partially positive hydrogen atom and a highly electronegative, partially negative oxygen, nitrogen, sulfur, or fluorine atom not covalently bound to said hydrogen atom. The term "hybridization" as used herein refers to the pairing of complementary nucleic acids, i.e. DNA and/or RNA, using any process by which a strand of nucleic acid joins with a complementary strand through base pairing to form a hybridized complex. Hybridization and the strength of hybridization (i.e., the strength of the association between the nucleic acids) is impacted by such factors as the degree and length of complementarity between the nucleic acids, stringency of the conditions involved, the Tm of the formed hybrid, and the G:C ratio within the nucleic acids. The term hybridized complex refers to a complex formed between two nucleic acid sequences by virtue of the formation of hydrogen bounds between complementary G and C bases and between complementary A and T/U bases. A hybridized complex or a corresponding hybrid construct can be formed between two DNA nucleic acid molecules, between two RNA nucleic acid molecules or between a DNA and an RNA nucleic acid molecule. For all constellations, the nucleic acid molecules can be naturally occurring nucleic acid molecules generated in vitro or in vivo and/or artificial or synthetic nucleic acid molecules. Hybridization as detailed above, e.g. Watson-Crick base pairs, which can form between DNA, RNA and DNA/RNA sequences, are dictated by a specific hydrogen bonding pattern, which thus represents a non-covalent attachment form according to the present invention.

Concerning non-covalent associations according to the present invention, the at least one CRISPR nucleic acid sequence and the at least one repair template sequence can associate with each other by RNA-DNA base pairing.

Another form of non-covalent interaction is the association of the at least one repair template sequence with at least one component, either CRISPR nucleic acid sequence or CRISPR polypeptide, by electrical charges.

Concerning a covalent association or attachment, the at least one CRISPR nucleic acid sequence and the at least one repair template sequence are connected as contiguous molecule, either produced in vivo or in vitro. Covalent and non-covalent attachment can also be combined, e.g. by providing a covalently attached CRISPR nucleic acid sequence/repair template sequence, which can further comprise an additional repair template nucleic acid sequence non-covalently attached to covalently attached CRISPR nucleic acid sequence/repair template sequence. This approach is especially suitable, in case the covalently attached CRISPR nucleic acid sequence/repair template sequence is at least partially produced in vivo and a further repair template, either produced in vivo or in vitro, is to be added to the pre-existing CRISPR nucleic acid sequence/repair template complex.

According to the various embodiments of the present invention, the above disclosure with respect to covalent and non-covalent association or attachment also applies for CRISPR nucleic acids sequences, which may comprise more than one portion, for example, a crRNA and a tracrRNA portion, which may be associated with each other as detailed above. In another embodiment, a RT may be placed within a CRISPR nucleic acid sequence of interest to form a hybrid nucleic acid sequence according to the present invention, which hybrid may be formed by covalent and non-covalent associations as detailed above.

As also evident from Nishimasu et al., supra, a gRNA may be configured to interact with a CRISPR polypeptide in accordance with the disclosure of the present invention, if the gRNA comprises at least one portion usually comprising a heteroduplex configuration, which is recognized by a CRISPR polypeptide either in a sequence dependent way, i.e. via interaction with the bases of an RNA, comprising A, U, G and C, or in a sequence-independent manner, i.e. via interaction of the backbone phosphate of a gRNA nucleotide sequence with a CRISPR polypeptide.

According to certain embodiments of the first aspect as well as the further aspects of the present invention, the first DNA target sequence may be located within the genome of a cell, preferably a eukaryotic cell, more preferably a fungal, an animal or a plant cell, wherein the genome comprises the nuclear genome as well as other genome parts, including the genome of plastids.

A "DNA target sequence" defines the genomic region, where a targeted genome editing is to be made. Due to the fact that the CRISPR nucleic acid sequence and the repair template nucleic acid sequence intrinsically have different functionalities, there can be a first and a second DNA target region. The first DNA target sequence thus defines the region of a DNA target region of interest the first sequence portion of the CRISPR nucleic acid sequence is complementary to, whilst the second DNA target sequence defines the region of a DNA target region of interest at least one portion of the repair template nucleic acid sequence is complementary to. The first and the second DNA target region can be the same, or preferably different, yet possibly overlapping regions, within the DNA target sequence of interest.

The spatial relation between the target site for the CRISPR nucleic acid sequence and the site of homology for the repair template nucleic acid sequence (RT) can be variable. The two sites can be identical, can be completely or partially overlapping, or can be separated by any number of nucleotides within the genome of interest. The RT can have homology to both strands of genomic DNA, or either strand individually, independent of which strand is targeted by the CRISPR nucleic acid sequence spacer sequence. An efficient repair template may be configured to have complementarity specific to the cleaved DNA strand first released by Cas9 (as described in Richardson, et al., Nature Biotechnology. 2016, doi: 10.1038/nbt.3481).

The hybrid RNA/DNA nucleic acid sequence according to the present invention is predicted to overcome the generally low efficiency of homology-directed repair (HDR)/homologous recombination (HR) as it guarantees the physical availability of the repair template nucleotide sequence present in a stochiometric way in relation to the CRISPR nucleic acid sequence moiety and the CRISPR polypeptide in situ at the place a targeted genomic strand break is introduced by the CRISPR polypeptide in a DNA target sequence.

The term DNA modification repair template as part of the hybrid RNA/DNA nucleotide sequence according to the present invention thus implies a nucleotide sequence, which can be a single-stranded or double-stranded DNA sequence, which is capable of providing a template for modification and/or repair of a DNA break.

In one preferred embodiment according to the first aspect of the present invention, the hybrid RNA/DNA nucleotide sequence may be an in vitro pre-assembled complex, wherein the RNA and the DNA portion are either covalently attached to each other or non-covalently associated. In one embodiment, the RNA/DNA nucleotide sequence is pre-assembled and the CRISPR polypeptide is separately delivered into a target cell, either as transcribable DNA or translatable RNA construct or directly as amino acid sequence and the RNA/DNA nucleotide sequence and the CRISPR polypeptide form a complex within the target cell. In another embodiment, the RNA/DNA nucleotide sequence as well as the CRISPR polypeptide may be assembled in vitro and the ribonucleoprotein complex is then introduced into a target cell of interest comprising at least one DNA target nucleotide sequence of interest to be modified.

Introduction of a functional pre-assembled complex into a target cell, in case a CRISPR endonuclease is used, results in a targeted double-strand break and simultaneous repair and site-specific modification due to the fact that the activity of the RNA guided CRISPR polypeptide is immediately accompanied by the subsequent homologous recombination at the site of the second DNA target sequence according to the present invention with the DNA repair template nucleotide sequence linked to the CRISPR nucleic acid sequence. Therefore, the drawbacks of poor availability of a RT or of unspecific NHEJ events (see Background of the Invention above) hampering a highly-specific and controllable genome editing event can be simultaneously reduced, as the molecular complex comprising a hybrid RNA/DNA nucleotide sequence and a corresponding CRISPR polypeptide can reach a target site in a coordinated way in an adequate stochiometric composition of CRISPR nucleic acid sequence:CRISPR polypeptide and CRISPR nucleic acid sequence/CRISPR polypeptide:repair template. A further benefit is that the potential for off-target integration of the repair template is reduced due to its physical association with the protein and RNA components of the complex, which cannot be integrated into the genome per se.

The term "targeted homology directed repair" according to the present disclosure comprises any type of alterations that can be introduced by the repair template sequence according to the present application, which can independently comprise sequence insertions, edits of at least one sequence position, deletions or rearrangements, the preferable strategy for genome editing approaches in higher eukaryotes presently being insertions, deletions or edits, as these strategies allow the targeted knock-in or knock-out of a sequence of interest within a DNA target sequence, or a site-specific modification of at least one sequence.

Figure 3:
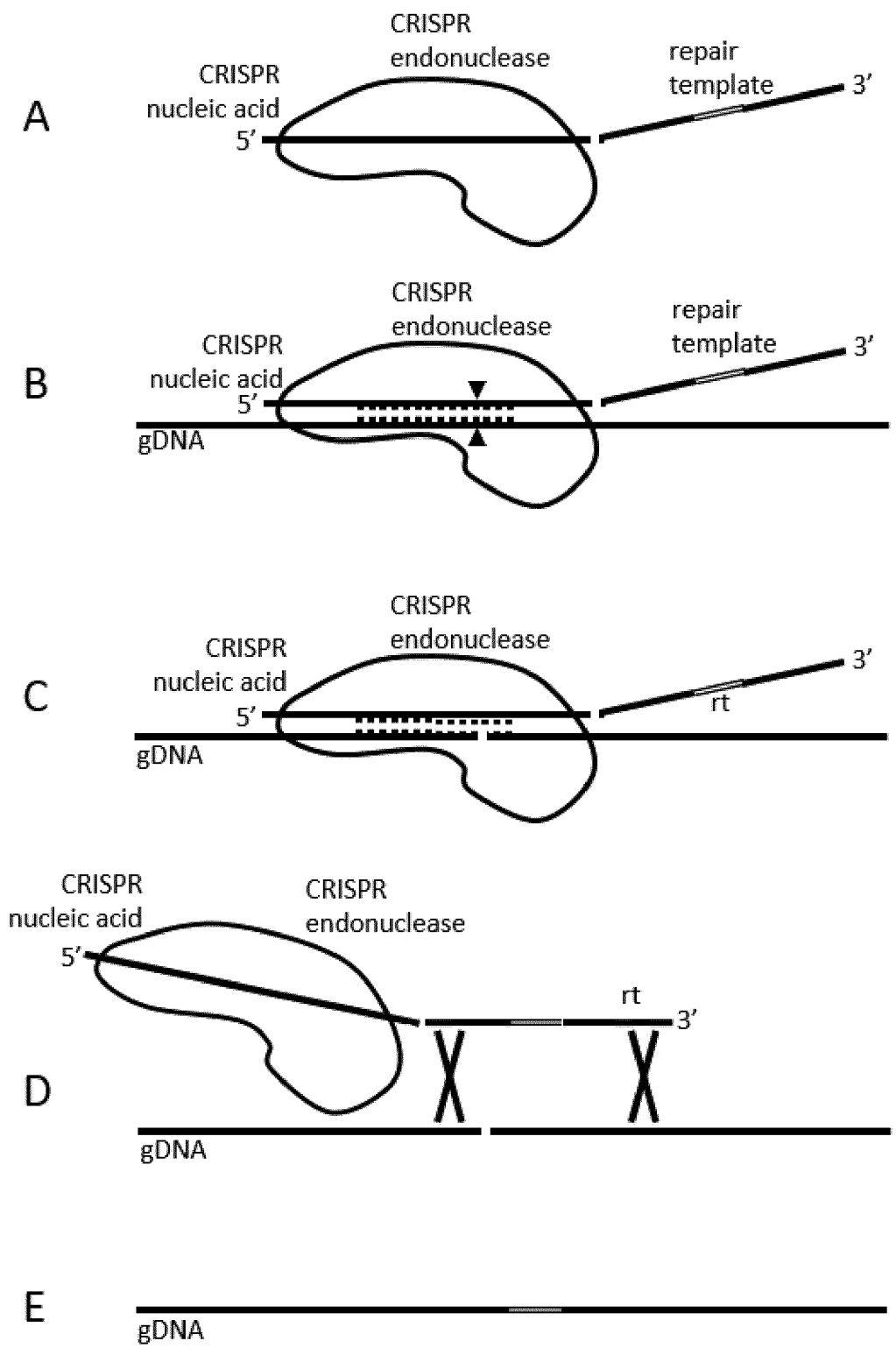
FIG. 3 A to E (FIG. 3 A to E): shows a non limiting example for the stepwise introduction of an edit into a genomic sequence of interest with the nuclease complex disclosed herein, using one embodiment of the covalent association of the RT with or within the 3'-region of the CRISPR nucleic acid, for example, a sgRNA or tracrRNA as an example. (A) Schematic of the hybrid RNA-DNA nucleic acid (CRISPR nucleic acid, e.g., sgRNA, and repair template (rt)) in complex with a CRISPR endonuclease, for example Cas9, Cpf, CasX or CasY or any variant thereof. (B) Schematic of the complex bound to the target DNA (genomic DNA (gDNA)) and indication of the cutting sites (black triangles). (C) Schematic of the cleaved target DNA. (D) Schematic of the cleaved target DNA released by the CRISPR nuclease and interacting with the repair template (rt) by complementary Watson-Crick base pairing. (E) Schematic of the repaired target site (gDNA) including the edits (shown in grey) copied from the RT during homologous recombination. The repair template (RT/rt) portion is shown in grey in all Figures.

An example for targeted homology directed repair as mediated by the molecular complex formed ex vivo or in vivo in cooperating with the hybrid nucleic acid sequence according to the present invention can be found in FIG. 3 A to E illustrating the chronological sequence of DNA recognition, binding, cleavage and subsequent repair for an exemplary CRISPR endonuclease/CRISPR nucleic acid sequence/repair template complex and for a given endogenous DNA target sequence.

In one embodiment according to the various aspects of the present invention, the repair template nucleic acid sequence and/or the CRISPR nucleic acid sequence may comprise a nucleotide sequence selected from a naturally or non-naturally occurring nucleotide sequence, including a synthetic nucleotide sequence, optionally comprising backbone and/or base modifications, wherein the CRISPR nucleic acid sequence comprises a single-stranded, or partially single-stranded RNA nucleotide sequence, and wherein the repair template nucleic acid sequence comprises a single-stranded or a double-stranded DNA nucleotide sequence.

A challenge for any CRISPR genome editing approach is the fact that the RNA portion of the hybrid nucleic acid sequence of the present invention and the functional CRISPR polypeptide have to be transported to the nucleus or any other compartment comprising genomic DNA, i.e. the DNA target sequence, in a functional (not degraded) way. As RNA is less stable than a polypeptide or double-stranded DNA and has a higher turnover, especially as it can be easily degraded by nucleases, in some embodiments according to the first aspect of the present invention, the CRISPR RNA sequence and/or the DNA repair template nucleic acid sequence comprises at least one non-naturally occurring nucleotide. Preferred backbone modifications according to the present invention increasing the stability of the CRISPR RNA and/or the DNA repair template nucleic acid sequence are selected from the group consisting of a phosphorothioate modification, a methyl phosphonate modification, a locked nucleic acid modification, an O-(2-methoxyethyl) modification, a di-phosphorothioate modification, and a peptide nucleic acid modification. Notably, all said backbone modifications still allow the formation of complementary base pairing between two nucleic acid strands, yet are more resistant to cleavage by endogenous nucleases. Depending on the CRISPR nuclease utilized in combination with a hybrid RNA/DNA nucleic acid sequence according to the present invention, it might be necessary not to modify those nucleotide positions of a CRISPR nucleic acid sequence, which are involved in sequence-independent interaction with the CRISPR polypeptide. Said information can be derived from the available structural information as available for CRISPR nuclease/CRISPR nucleic acid sequence complexes.

In certain embodiments according to the first aspect of the present invention, it is envisaged that the CRISPR nucleic acid sequence and/or the DNA repair template nucleic acid sequence may comprise a nucleotide and/or base modification, preferably at selected, not all, nucleotide sequence positions. These modifications are selected from the group consisting of addition of acridine, amine, biotin, cascade blue, cholesterol, Cy3, Cy5, Cy5.5, Daboyl, digoxigenin, dinitrophenyl, Edans, 6-FAM, fluorescein, 3'-glyceryl, HEX, IRD-700, IRD-800, JOE, phosphate psoralen, rhodamine, ROX, thiol (SH), spacers, TAMRA, TET, AMCA-S", SE, BODIPY®, Marina Blue®, Pacific Blue®, Oregon Green®, Rhodamine Green®, Rhodamine Red®, Rhodol Green® and Texas Red®. Preferably, said additions are incorporated at the 3' or the 5' end of the CRISPR nucleic acid sequence and/or the DNA repair template nucleic acid sequence. This modification has the advantageous effects, that the cellular localization of the CRISPR nucleic acid sequence and/or the DNA repair template nucleic acid sequence within a cell can be visualized to study the distribution, concentration and/or availability of the respective sequence. Furthermore, the interaction of the CRISPR polypeptide of interest with the hybrid RNA/DNA construct according to the present invention can be studied. Methods of studying such interactions or for visualization of a nucleotide sequence modified or tagged as detailed above are available to the skilled person in the respective field.

In one embodiment, any nucleotide of the CRISPR nucleic acid sequence and/or the DNA repair template nucleic acid sequence can comprise one of the above modifications as a label or linker comprised by at least one nucleotide of the CRISPR nucleic acid sequence and/or the DNA repair template nucleic acid sequence. As used herein, "nucleotide" can thus generally refer to a base-sugar-phosphate combination. A nucleotide can comprise a synthetic nucleotide. A nucleotide can comprise a synthetic nucleotide analog. Nucleotides can be monomeric units of a nucleic acid sequence (e.g., deoxyribonucleic acid (DNA) and ribonucleic acid (RNA)). The term nucleotide can include ribonucleoside triphosphates adenosine triphosphate (ATP), uridine triphosphate (UTP), cytosine triphosphate (CTP), guanosine triphosphate (GTP) and deoxyribonucleoside triphosphates such as dATP, dCTP, dTTP, dUTP, dGTP, dTTP, or derivatives thereof. Such derivatives can include, for example and not limitation, [αS]dATP, 7-deaza-dGTP and 7-deaza-dATP, and nucleotide derivatives that confer nuclease resistance on the nucleic acid molecule containing them. The term nucleotide as used herein can refer to dideoxyribonucleoside triphosphates (ddNTPs) and their derivatives. Illustrative examples of dideoxyribonucleoside triphosphates can include, but are not limited to, ddATP, ddCTP, ddGTP, ddITP, and ddTTP. A nucleotide may be unlabeled or detectably labeled by well-known techniques. Labeling can also be carried out with quantum dots. Detectable labels can include, for example, radioactive isotopes, fluorescent labels, chemiluminescent labels, bioluminescent labels and enzyme labels. Fluorescent labels of nucleotides may include but are not limited to fluorescein, 5-carboxyfluorescein (FAM), 2'7'-5 dimethoxy-4'5-dichloro-6-carboxyfluorescein (JOE), rhodamine, 6-carboxyrhodamine (R6G), N,N,N',N'-tetramethyl-6-carboxyrhodamine (TAMRA), 6-carboxy-X-rhodamine (ROX), 4-(4'dimethylaminophenylazo) benzoic acid (DABCYL), Cascade Blue, Oregon Green, Texas Red, Cyanine and 5-(2'-aminoethyl)aminonaphthalene-I-sulfonic acid (EDANS).

Labels or linkers can also comprise moieties suitable for click chemistry to link the CRISPR nucleic acid sequence or a portion thereof and the DNA repair template nucleic acid sequence to each other, or to link the hybrid nucleic acid sequence to a CRISPR polypeptide of interest.

Of the reactions comprising the click chemistry field suitable to modify any nucleic acid or amino acid according to the present invention to build a molecular complex, in vitro or in vivo, one example is the Huisgen 1,3-dipolar cycloaddition of alkynes to azides to form 1,4-disubstituted-1,2,3-triazoles. The copper (I)-catalyzed reaction is mild and very efficient, requiring no protecting groups, and requiring no purification in many cases. The azide and alkyne functional groups are generally inert to biological molecules and aqueous environments. The triazole has similarities to the ubiquitous amide moiety found in nature, but unlike amides, is not susceptible to cleavage. Additionally, they are nearly impossible to oxidize or reduce.

As it is known to the skilled person, certain click chemistry reactions suitable for in vivo reactions rely on reactive groups, such as azides, terminal alkynes or strained alkynes (e.g., dibenzocyclooctyl (DBCO)), which reactive groups can be introduced into any form of RNA or DNA via accordingly modified nucleotides that are incorporated instead of their natural counterparts. Labels can be introduced enzymatically or chemically. The resulting CLICK-functionalized DNA can subsequently be processed via Cu(I)-catalyzed alkyne-azide (CuAAC) or Cu(I)-free strained alkyne-azide (SPAAC) click chemistry reactions, wherein copper-free reactions are preferable for applications within a cell or living system. These reactions can be used according to the present invention to introduce a biotin group for subsequent purification tasks (via azides, alkynes of biotin or DBCO-containing biotinylation reagents), to introduce a fluorescent group for subsequent microscopic imaging (via fluorescent azides, fluorescent alkynes or DBCO-containing fluorescent dyes), or to crosslink to biomolecules, e.g., the CRISPR nucleic acid sequence and a DNA repair template according to the present invention to covalently link and/or provide functionalized biomolecules.

In one embodiment, an optionally purified and functionally associated 5' or 3'end click-chemistry-labeled hybrid nucleic acid sequence according to the present invention may be delivered by any transformation or transfection method to a cell or cell system stably or transiently expressing a corresponding CRISPR polypeptide. Thereby, as the CRISPR nucleic acid sequence of the hybrid nucleic acid sequence interacts with and thereby activates the CRISPR polypeptide while already being attached to a repair template. During the cut in the genomic target site of interest, the close proximity of the repair template to the cut site thereby enhances the HDR frequency. In certain embodiments, the CRISPR polypeptide may comprise a click-chemistry-label compatible with and thus able to react with the click chemistry label present at the 5' and/or 3' end of the hybrid nucleic acid sequence.

A variety of further chemical reactions and the corresponding modifications are available to the skilled person to link to nucleic acids according to the present disclosure, i.e., any CRISPR nucleic acid and a single or double stranded repair template, to each other in a covalent way. These modifications include a variety of crosslinkers, such as thiol modifications, like a thioctic acid N-hydroxysuccinimide (NHS) ester, chemical groups that react with primary amines (—NH2). These primary amines are positively charged at physiologic pH; therefore, they occur predominantly on the outside surfaces of native protein tertiary structures where they are readily accessible to conjugation reagents introduced into the aqueous medium. Furthermore, among the available functional groups in typical biological or protein samples, primary amines are especially nucleophilic; this makes them easy to target for conjugation with several reactive groups. There are numerous synthetic chemical groups that will form chemical bonds with primary amines. These include isothiocyanates, isocyanates, acyl azides, NHS esters, sulfo-NHS esters containing a sulfonate (—SO3) group, for example, bis(sulfosuccinimidyl)suberate (BS3), sulfonyl chlorides, aldehydes, glyoxals, epoxides, oxiranes, carbonates, aryl halides, imidoesters, carbodiimides, such as, for example 1-Ethyl-3-(3-dimethylaminopropyl)carbodiimide (EDC) or dicyclohexylcarbodiimide (DCC), anhydrides, and fluorophenyl esters.

For the purpose of coupling a CRISPR nucleic acid sequence and a DNA repair template nucleic acid sequence, it will be favourable to insert a modification or a label at the 5' or 3'end of the respective nucleic acid sequence so that a subsequent covalent linkage can be created between CRISPR nucleic acid sequence and a DNA repair template nucleic acid sequence in the desired direction. The positioning of the modification or a label will depend on the topology of the hybrid nucleic acid construct to be produced as evident from the different topologies or configurations as illustrated in FIG. 1a and FIG. 1b, respectively.

For any embodiment according to the various aspects of the present invention it is necessary, that the hybrid nucleic acid sequence as well as the CRISPR polypeptide reach the DNA target sequence of interest in the relevant compartment within a target cell of interest. According to certain embodiments of the present invention, the localization sequence can comprise a nuclear localization sequence, a plastid localization sequence, preferably a mitochondrion localization sequence or a chloroplast localization sequence. Therefore, the CRISPR polypeptide and/or the hybrid nucleic acid construct have to comprise a corresponding localization sequence, preferably a nuclear localization sequence (NLS) for directing the complex to the nuclear genome of cell. In some embodiments, the CRISPR enzyme or the hybrid nucleic acid may comprise about or more than about 1, 2, 3, 4, 5, 6, 7, 8, 9, 10, or more NLSs at or near the amino-terminus, or at or near the 5' end of the hybrid nucleic acid sequence, respectively, about or more than about 1, 2, 3, 4, 5, 6, 7, 8, 9, 10, or more NLSs at or near the carboxyterminus, or at or near the 3' end of the hybrid nucleic acid sequence, respectively, or a combination of these (e.g. one or more NLS at the amino-terminus/5'end and one or more NLS at the carboxy-terminus/3'end). When more than one NLS is present, each may be selected independently of the others, such that a single NLS may be present in more than one copy and/or in combination with one or more other NLSs present in one or more copies. In a preferred embodiment of the invention, the CRISPR enzyme and/or hybrid nucleic acid sequence may comprise at most 6 NLSs. For attaching a NLS to a hybrid nucleic acid sequence according to the present invention, the NLS may be provided as peptide or in vitro transcribed sequence, which can then be chemically attached to a CRISPR nucleic acid sequence, a RT, or at the free 5' and/or 3' end of an hybrid nucleic acid sequence.

In some embodiments, wherein a NLS is attached to a CRISPR polypeptide, or to the sequence encoding the same, a NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. Non-limiting examples of NLSs include an NLS sequence derived from: the NLS of the SV40 virus large T-antigen, having the amino acid sequence PKKKRKV (SEQ ID NO:1); the NLS from nucleoplasmin (e.g. the nucleoplasmin bipartite NLS with the sequence KRPAATKKAGQAKKKK (SEQ ID NO:2)); the c-myc NLS having the amino acid sequence PAAKRVKLD (SEQ ID NO:3) or RQRRNELKRSP (SEQ ID NO:4); the hRNPA1 M9 NLS having the sequence NQSSNFGPMKGGNFGGRSSGPYGGGGQYFAK-PRNQGGY (SEQ ID NO:5); the sequence RMRIZFKNKGKDTAELRRRRVEVSVELRKAKKD-EQILKRRNV (SEQ ID NO:6) of the IBB domain from importin-alpha; the sequences VSRKRPRP (SEQ ID NO:7) and PPKKARED (SEQ ID NO:8) of the myoma T protein; the sequence PXPKKKPL (SEQ ID NO:9) of human p53, wherein the "L" at position 8 of SEQ ID NO:9 is optional; the sequence SALIKKKKKMAP (SEQ ID NO:10) of mouse c-abl IV; the sequences DRLRR (SEQ ID NO:11) and PKQKKRK (SEQ ID NO:12) of the influenza virus NS1; the sequence RKLKKKIKKL of the Hepatitis virus delta antigen (SEQ ID NO:13); the sequence REKKKFLKRR (SEQ ID NO:14) of the mouse Mx1 protein; the sequence KRKGDEVDGVDEVAKKKSKK (SEQ ID NO:15) of the human poly(ADP-ribose) polymerase; and the sequence RKCLQAGMNLEARKTKK (SEQ ID NO:16) of the steroid hormone receptors (human) glucocorticoid. In some embodiments, the localization signal can be a plastid localization signal, for example a plastid or a mitochondria localization signal. Suitable plastid localization signals are selected from the group consisting of chloroplast transit peptides or mitochondrial targeting peptides. Furthermore, peptides derived from the HIV Tat protein, or sequences encoding the same, can be suitable for targeting a construct or molecule of interest into a cell and/or sub-cellular compartment of interest. Suitable Tat peptides are derived from YGRKKRRQRRR (SEQ ID NO:17) or comprise the motif GRKKR (SEQ ID NO:18).

In embodiments, wherein the CRISPR polypeptide is delivered to a cell with the help of at least one delivery vector in the form of a nucleic acid sequence, the localization signal can be covalently attached to the at least one CRISPR polypeptide encoding sequence in a covalent way as nucleic acid sequence encoding a localization signal at any suitable position within the CRISPR polypeptide not disturbing the recognition and/or cleavage function of the CRISPR polypeptide.

In one embodiment, the at least one CRISPR polypeptide can be covalently or non-covalently associated with a fluorescent reporter gene or protein. This reporter can be delivered as DNA, as mRNA, as an independent protein, or as a fusion protein linked to the at least one CRISPR polypeptide.

The hybrid nucleic acid sequence molecule according to the present invention comprising a CRISPR nucleic acid sequence moiety and a repair template (RT) moiety can be produced by several ways. It can be made by chemical synthesis, adding RNA bases where appropriate in the synthesis process and DNA bases where appropriate in the synthesis process. Alternatively, the CRISPR nucleic acid sequence and the RT can be synthesized independently of each other and the molecules can then be associated with each other as described above. Another option is to use T4 RNA ligase or another enzyme capable of ligating nucleic acids to RNA, preferably single-stranded RNA. Here, the RNA and DNA components are generated independently by any method, mixed, exposed to the enzyme according to the manufacturer's protocol, and they will be covalently linked by ligation, i.e. to generate a covalent attachment. Modifications and labels as disclosed herein may be used to covalently link CRISPR nucleic acid sequence moieties and RT moieties to each other. Other strategies for covalent bonding of the CRISPR nucleic acid sequence to the RT include linking each of them to other linking chemical groups or complexes, such as to a peptide. This type of approach is especially suitable, when the hybrid nucleic acid sequence has to be detected later on within the cell, or when a further function should be attributed to the hybrid nucleic acid sequence. Chemical modification of either the CRISPR nucleic acid sequence and/or the hybrid nucleic acid sequence can be of great importance to stabilize the hybrid nucleic acid sequence and to avoid degradation by cellular enzymes to achieve a high simultaneous availability of the hybrid nucleic acid sequence and the CRISPR polypeptide at the DNA target site of interest.

According to certain embodiments of the various aspects of the present invention, the at least one hybrid nucleic acid sequence can comprise a linker region between the CRISPR nucleic acid sequence and the repair template nucleic acid sequence. This sequence can serve to achieve optimum geometry of the CRISPR nucleic acid sequence and the repair template nucleic acid sequence so that both individual portions of the hybrid nucleic acid sequence can fully exert their function. The length and composition of the linker or tether regions may be an important design aspect for certain CRISPR nucleic acid sequence and RT pairs. In one embodiment, especially the 5' end of the left homology arm of the RT can comprise a linker region. The tether or linker can take a variety of forms. Starting from the left or right homology arm of the RT, allowing this portion of the RT to act as a tether or flexible linker to allow movement of the RT toward the chromosomal target, and as homology to mediate the HR reaction can be performed by the skilled person based on the present disclosure and having knowledge of usual design parameters for repair templates as presently widely used for genome editing.

Design parameters to be considered include geometry of the repair template homology relative to the cut site of a CRISPR polypeptide, the strand within a DNA target site of interest to which the repair template is homologous, size of the repair template, which can influence, whether a linker and in which length a linker will be introduced. A linker sequence can be used for both covalent and non-covalent associations of the CRISPR nucleic acid sequence and the repair template. Based on the present disclosure and based on the information provided in Nishimasu (supra), Tsai et. al (Nature Biotechnology, 32, 569-576, (2014)), or Shechner et al. (Nature Methods, 12(7), 664-670 (2015), doi: 10.1038/nmeth.3433), the skilled person can thus define a suitable linker region for a hybrid nucleic acid sequence to define a specific sequence between the CRISPR nucleic acid sequence and the RT or between different CRISPR nucleic acid sequences and or RTs, in case several hybrid nucleic acids are used so that both the CRISPR nucleic acid sequence(s) and the RT moiety can fully exert their function without any sterical constraints. The at least one linker region can comprise up to 10, 15, 20, 25, 30, 35, 40, 45, 50, 55, 60, 65, 70, 75, 80, 85, 90, 95 or 100 additional nucleotides to properly separate the at least one CRISPR nucleic acid sequence from the RT, or to optimize the positioning of the CRISPR nucleic acid sequence and/or the RT. In certain embodiments, the linker sequence can comprise up to 150, 200, 250, 500, 1,000, 1,500, 2,000, 2,500, 3,000, 3,500, 4,000, 4,500 or at least 4,700 or 5,000 nucleotides to achieve a better positioning of the CRISPR nucleic acid sequence and/or the RT.

For non-covalent association of the CRISPR nucleic acid sequence with the RT, one approach is to provide partially complementary sequences in the CRISPR nucleic acid sequence and RT so that the two molecules will naturally associate by RNA-DNA base pairing.

Other methods of non-covalent association are conceivable, such as the use of electrical charges of molecules to cause a sufficient association of the RT with some component of the editing complex. In another embodiment, at least one CRISPR polypeptide or at least one hybrid nucleic acid sequence, or the CRISPR nucleic acid sequence and/or the RT portion thereof, can comprise a tag and the binding partner, i.e. the hybrid nucleic acid sequence, or the CRISPR nucleic acid sequence and/or the RT portion thereof, and the at least one CRISPR polypeptide, respectively, comprise the corresponding binding partner of the tag so that a non-covalent interaction in addition to the base pairing between CRISPR nucleic acid sequence and RT and the association between CRISPR nucleic acid sequence and CRISPR polypeptide is achieved to increase the interaction and thus stability of the molecular ribonucleoprotein complex.

In human cells, Cas9 loaded with a gRNA possessing 28 bp of additional sequence on the 3' end plus an associated 187 amino acid (21.4 kD) Csy4 protein maintained at least 90% activity in DSB induction compared to standard gRNA controls (Tsai et al., Nature Biotech., 32, 2014). This suggests a fairly substantial tolerance by Cas9 for cargo tethered to the 3' end of the sgRNA and of proper structure-function potential for the extended sgRNA molecule. Cas9 tolerance is enabled in part by the flexibility of the free 3' end of the nucleic acid sequence, which in a standard gRNA terminates in a hairpin that is held outside the architecture of the Cas9 protein and on a surface roughly perpendicular to the surface holding the active site (Nishimasu et al., 2014; Anders et al., 2014). Furthermore, Shechner et al. ("Multiplexable, locus-specific targeting of long RNAs with CRISPR-Display", Nature Methods, 12(7), 664-670 (2015), doi: 10.1038/nmeth.3433) show that long noncoding ssRNA molecules can be transcriptionally attached to the 5'- or 3'-ends of the sgRNA, or in an internal loop of the sgRNA without loss of sequence-specific targeting activity by a dCas9 protein in the human cell genome. ssRNAs of up to 4.8 kb were accommodated by the ribonucleoprotein complex with maintenance of sequence-specific targeting activity.

In one embodiment according to the various aspects of the present invention, the repair template nucleic acid sequence is associated with the CRISPR nucleic acid sequence at the 3' end of the CRISPR nucleic acid sequence, and/or wherein the repair template nucleic acid sequence is associated with the 5' end of the CRISPR nucleic acid sequence, and/or wherein the repair template nucleic acid sequence is located within the CRISPR nucleic acid sequence.

Surprisingly, it was found by the inventors of the present invention that a CRISPR nucleic acid sequence carrying a 3' located DNA repair template sequence (RT), either a single-stranded or a double-stranded RT, was free to interact with homologous sequence as it is delivered to the target by a CRISPR polypeptide, e.g. Cas9 from a CRISPR type II system, or Cpf1 from a CRISPR type V system or another CRISPR polypeptide effector. Similar observations were made when a CRISPR nucleic acid sequence carrying a 5' located DNA repair template sequence), either a single-stranded or a double-stranded RT, or both, a 3' and 5' located RT, were used. 3' or 5' located thus implies that the RT is either covalently attached to the 3' or 5' end of a CRISPR nucleic acid sequence, or it can mean that the RT is hybridized to, i.e. non-covalently associated with, a region corresponding to sequence attached to the 3' and/or the 5' region of the CRISPR nucleic acid sequence. In addition, the RT could be covalently incorporated in the stem loops of a CRISPR nucleic acid sequence, or it could be non-covalently be associated with said CRISPR nucleic acid sequence stem loops to achieve a functional hybrid nucleic acid construct. Thus, it was found that DNA associated with a CRISPR nucleic acid sequence at various positions of the CRISPR nucleic acid sequence as described above was well tolerated and this new form of hybrid complex, therefore, is suitable to bring together two key aspects of the gene editing principle: (1) precision of targeting mediated by the CRISPR nucleic acid sequence and (2) efficient and site-directed repair as mediated by the RT. Furthermore, there is the synergistic effect that CRISPR nucleic acid sequence and RT are brought into close proximity to increase the stability and the availability of the hybrid construct together with a CRISPR polypeptide of interest at a DNA target site of interest.

There are nearly no limitations on the length of this extended repair template nucleotide sequence delivered together with the CRISPR nucleic acid sequence, in case the RT is attached to the 3' or the 5' end of a CRISPR nucleic acid sequence. The length of the RT is then rather dictated by the targeted modification to be introduced. Typical RT sequences can have a length from about 20 to 8,000 bp or even more, e.g. of 20 to 5,000 bp, of 30 to 8,000 bp, of 30 to 5,000 bp, of 40 to 8,000 bp, of 40 to 5,000 bp, of 50 to 8,000 bp, of 50 to 5,000 bp, of 60 to 8,000 bp, of 60 to 5,000 bp, of 70 to 8,000 bp, of 70 to 5,000 bp, of 80 to 8,000 bp, of 80 to 5,000 bp, of 90 to 8,000 bp, of 90 to 5,000 bp, of 100 to 8,000 bp, of 100 to 5,000 bp of single-stranded and or double-stranded DNA without a significant loss in cutting frequency of the CRISPR polypeptide is observed. As it is known to the skilled person, the length of a RT template is strongly dictated by the kind of modification/insertion to be effected/introduced. In case a knock-in of a larger nucleic acid sequence encoding a protein of interest is intended, the length of the RT sequence will have the length: length of the nucleic acid construct encoding the protein of interest plus two sufficiently long homology arms located left and right of the sequence. Thus, there is in principle no upper limit of 1,500 bp, but the RT can have up to 5,000 or even more base pairs (bp). For example, larger inserts presently introduced using a plasmid DNA as repair template and producing the repair template within a target site use left and right homology arms of 800 bp and more so that the total length of a repair template can have several 1,000 bp. The length of the nucleic acid inserts should be designed not to inhibit the CRISPR nuclease of interest, e.g. a Cas nuclease or a Cpf1 nuclease, which can be determined in preexperiments.

In a second aspect according to the present invention there is provided a molecular complex comprising at least one hybrid nucleic acid sequence according to the first aspect of the present invention and at least one CRISPR polypeptide, wherein the at least one hybrid nucleic acid sequence and at least one CRISPR polypeptide are associated in a functional way.

The term "associated in a functional way" implies that the molecular ribonucleoprotein complex is brought into contact so that the CRISPR polypeptide and the second sequence portion of the CRISPR nucleic acid sequence can interact with each other, preferably by a form of non-covalent association as detailed above. The at least one hybrid nucleic acid sequence comprising at least one CRISPR nucleic acid sequence and at least one repair template nucleic acid sequence are independently assembled, either before, after, or simultaneously with contacting the at least one CRISPR nucleic acid sequence with the at least one corresponding CRISPR polypeptide of interest. In one embodiment, the whole complex is associated in vitro before it is introduced into a target cell comprising at least one DNA target region of interest to be edited. In another embodiment, the at least one CRISPR polypeptide is introduced into the at least one target cell before or after the at least one hybrid nucleic acid sequence. The CRISPR polypeptide can be introduced into a target cell by means of transfecting the polypeptide sequence or by transfecting or transforming at least one target cell with RNA encoding the at least one polypeptide or by introducing a delivery construct encoding at least one CRISPR polypeptide which can be transcribed and translated in a target cell. In certain embodiments, the CRISPR polypeptide may also be stably integrated into the genome of a cell or organism of interest to be expressed constitutively or in an inducible way. Likewise, in certain embodiments, the CRISPR nucleic acid sequence(s) and the repair template nucleic acid sequence(s) can be provided simultaneously as in vitro provided and assembled construct. Alternatively, either the CRISPR nucleic acid sequence and/or the repair template nucleic acid sequence can be transfected or transformed into a target cell with the help of a suitable delivery vector as detailed above. In a preferred embodiment, the whole molecular complex is assembled in vitro and then introduced into a target cell of interest to allow best spatial and stochiometric control of the genome editing construct. In another preferred embodiment, the at least one CRISPR polypeptide is introduced into a target cell before the hybrid nucleic acid sequence and the at least one hybrid nucleic acid sequence is then introduced into a target cell of interest afterwards. The sequential order might be preferable for certain approaches due to the intrinsically low stability of RNA in comparison to a polypeptide, so that the introduced CRISPR nucleic acid sequence will be immediately bound and stabilized by the CRISPR polypeptide already present in the cell. Without wishing to be bound by theory, the ex vivo assembly of a CRISPR nucleic acid sequence and a repair template nucleic acid sequence can also enhance the stability of the construct in comparison to, for example, a guide RNA alone.

In yet a further embodiment, the individual components of the molecular complex can comprise at least one modification in the form of a label or linker as described above. Said modifications can help to associate the molecular complex in vivo or in vitro to achieve a stable covalent or non-covalent association. For example, click chemistry groups or NHS-ester chemistry can be used to covalently link the molecules. Alternatively, non-covalent associations may be achieved via biotin as one modification and a biotin-binding protein moiety, or between a single-chain Fv antibody fragment and its cognate target, said modifications being present within the component of the molecular complex to be joined. By these methods, functional associations between a nucleic acid and another nucleic acid, or between a nucleic acid and an amino acid component can be achieved.

For certain applications, it might be suitable to associate the components in vitro before introduction into a cell of interest. For other applications, e.g., for visualizing processes in a cell, it might be suitable to use a molecular complex comprising at least one fluorescent portion or dye. To monitor the (sub)cellular localization and/or dynamics within a cell, it might thus be suitable to link the individual components only in vivo after introduction of the individual components, and optionally transcription/expression thereof.

The size of the at least one repair template nucleic acid sequence according to the present invention as part of the hybrid nucleic acid sequence and/or the molecular complex according to the present invention can vary. It can be in the range from about 20 bp to about 5,000 bp or even 8,000 bp depending on the DNA target sequence to be modified.

HDR templates used to create specific mutations or insertions into a DNA target region of interest require a certain amount of homology surrounding the target sequence that will be modified. It is best if the insertion sites of the modification are no more than 100 bp away from the DSB as effected by a CRISPR polypeptide or a fusion partner in the case of a nuclease deficient CRISPR polypeptide, ideally less than 10 bp away if possible, and the overall length of the homology arm is an important factor to consider when designing these. Longer distances will work, but the efficiency will likely be lower and the introduction of a selection marker might become necessary to ensure that the desired modification to be introduced into the DNA target sequence of interest is present.

According to the various aspects of the present invention, the at least one repair template nucleic acid sequence can be a single-stranded or double-stranded DNA nucleic acid molecule. The at least one repair template nucleic acid sequence can be provided in the form of one or more linear, ss- or ds-DNA molecules. However, it might be suitable to use at least one single-stranded or double-stranded repair template nucleic acid sequence, which is produced ex vivo, when a molecular complex is to be assembled ex vivo, which is especially suitable to increase the availability of the functional CRISPR nuclease-CRISPR nucleic acid-RT complex, as all components can be introduced simultaneously in the correct stochiometry to increase the specificity of the genome editing approach.

The synthesis of larger nucleic acid sequences, either single or double-stranded, can be accomplished using common prior art methods. It is noted that for certain embodiments, also partial single-stranded and/or partial double-stranded repair template nucleic acid sequences might be suitable. Any combination of a single-stranded and/or double-stranded nucleic acid sequence and any kind of introduction, either simultaneous with or before or after the introduction of the CRISPR polypeptide of the molecular complex is possible. In one embodiment, it is envisaged to introduce a molecular complex according to the second aspect into a target cell, wherein the target cell comprises an additional plasmid vector encoding a repair template or an additional repair template sequence, as the use of more than one repair template nucleic acid sequence is beneficial for certain genome editing approaches, wherein the molecular complex can then assemble in vivo after the different components are provided. In general, high physical availability of the repair template nucleic acid sequence at that site within a target cell, where the DNA target region is located is of outstanding importance to allow for a highly precise genome editing event. In certain embodiments, especially single-stranded (ss) DNA repair templates are suitable to strike the right balance keeping the molecular weight as low as possible while providing sufficient length for homology interactions to achieve optimum homology directed repair.

In one embodiment according to any aspect of the present invention, the at least one CRISPR polypeptide is independently selected from the group consisting of a Cas polypeptide of *Streptococcus* spp., including *Streptococcus pyogenes, Streptococcus thermophiles, Staphylococcus aureus*, or *Neisseria* spp., including *Neisseria meningitides, Corynebacter, Sutterella, Legionella, Treponema, Filifactor, Eubacterium, Lactobacillus, Mycoplasma, Bacteroides, Flaviivola, Flavobacterium, Sphaerochaeta, Azospirillum, Gluconacetobacter, Roseburia, Parvibaculum, Nitratifractor, Mycoplasma* and *Campylobacter*, or wherein the CRISPR polypeptide is selected from a Cpf1 polypeptide from an archaea or a *bacterium*, including a Cpf1 polypeptide of *Acidaminococcus* spp., including *Acidaminococcus* sp. BV3L6, *Lachnospiraceae* spp., including *Lachnospiraceae bacterium* ND2006, *Francisella* spp., including *Francisella novicida* U112, *Eubacterium eligens, Prevotella* spp., or *Porphyromonas* spp., or wherein the CRISPR polypeptide is selected from a CasX polypeptide or a CasY polypeptide, or variants and/or functional fragments and/or combinations thereof, including CRISPR polypeptide nickases, or a CRISPR polypeptide lacking endonucleolytic activity.

In one embodiment according to the present invention, the hybrid RNA/DNA nucleic acid sequences according to the present invention can be used with a CRISPR nickase, e.g. a Cas9 nickase, mutant to minimize off-target mutations, wherein paired guide RNAs are used, each of which is specific for a Cas9 derived nickase mutant.

In some embodiments, the CRISPR polypeptide is provided as in vitro expressed, translated or synthesized polypeptide. In some embodiments, a delivery vector is used encoding at least one CRISPR polypeptide, wherein the delivery vector can additionally comprise regulatory sequences or localization signals. A CRISPR polypeptide that is mutated with respect to a corresponding wild-type enzyme such that the mutated CRISPR enzyme lacks the ability to cleave one or both strands of a target polynucleotide containing a target sequence also comprised by various embodiments according to the present disclosure. For example, an aspartate-to-alanine substitution (D10A) in the RuvC I catalytic domain of Cas9 from *S. pyogenes* can be used which converts Cas9 from an endonuclease that cleaves both strands of a DNA target region of interest to a nickase cleaving a single-strand. Other examples of mutations that render a Cas9 polypeptide a nickase include, without limitation, H840A, N854A, and N863A. As a further example, two or more catalytic domains of Cas9 (RuvC I, RuvC II, and RuvC III or the HNH domain) may be mutated to produce a mutated Cas9 substantially lacking all DNA cleavage activity. In some embodiments, a D10A mutation is combined with one or more of H840A, N854A, or N863A mutations to produce a Cas9 enzyme substantially lacking all DNA cleavage activity. In some embodiments, a CRISPR enzyme is considered to substantially lack all DNA cleavage activity when the DNA cleavage activity of the mutated enzyme is about no more than 25%, 10%, 5%, 1%, 0.1%, 0.01%, or less of the DNA cleavage activity of the non-mutated form of the enzyme; an example can be when the DNA cleavage activity of the mutated form is null or negligible as compared with the non-mutated wild-type form. Where the enzyme is not Cas9 from *S. pyogenes*, mutations may be made at any or all residues corresponding to positions 10, 762, 840, 854, 863 and/or 986 of SpCas9 (which may be ascertained for instance by standard sequence comparison tools). In particular, any or all of the following mutations are preferred in Cas9 from *S. pyogenes*: D10A, E762A, H840A, N854A, N863A and/or D986A; as well as conservative substitution for any of the replacement amino acids is also envisaged according to the present disclosure. The same or conservative substitutions of these mutations at corresponding positions in other Cas9s are also possible for certain embodiments, particularly D10 and H840 in Cas9 from *S. pyogenes*. However, in other Cas9s, residues corresponding to D10 and H840 Cas9 from *S. pyogenes* are also possible. "Orthologs" or "orthologous" of given CRISPR proteins can also be used in the practice of the invention. Orthologs are genes in different species that evolved from a common ancestral gene by speciation. Normally, orthologs retain the same function in the course of evolution. A CRISPR enzyme may be identified Cas9 as this can refer to the general class of enzymes that share homology to the biggest nuclease with multiple nuclease domains from a type II CRISPR system. Most preferably, the Cas9 enzyme is from, or is derived from, *S. pyogenes* Cas9, or *S. aureus* Cas9, or wild type Cas9 from *S. thermophilus*, the protein sequence of which is give in the SwissProt database under accession number G3ECR1. Similarly, *S. pyogenes* Cas9 or *S. aureus* Cas9 is included in SwissProt under accession number Q99ZW2.

In one embodiment, the CRISPR nucleic acid sequence comprising at least one RNA of the hybrid RNA/DNA nucleic acid sequence according to the present invention may be designed for having optimal activity, i.e. recognition properties, towards a selected CRISPR enzyme or polypeptide of a specific length, the CRISPR enzyme can be truncated making it smaller in length than the corresponding wild-type CRISPR enzyme by truncating the nucleic acid molecules coding for the CRISPR enzyme which can be transcribed or translated in vitro or in vivo, or by providing a synthesized CRISPR polypeptide. Generating chimeric Cas9 enzymes, wherein different parts of the enzyme are swapped or exchanged between different orthologs to arrive at chimeric enzymes having tailored specificity is also possible.

A "variant" or "functional fragment" according to the present disclosure thus comprises any CRISPR protein or a truncated version thereof derived from the wild-type CRISPR protein, i.e. having a degree of sequence homology with, a wild-type enzyme, but that it has been mutated (modified) in some way as described herein. Enzymatic activity by Cas9 derived nuclease generates double-stranded breaks at target site sequences which hybridize to 20 nucleotides of the guide sequence and that have a protospacer-adjacent motif (PAM) sequence examples including NGG/NRG or a PAM that can be determined as described herein following the 20 nucleotides of the target sequence. This enzymatic function can be varied by generating CRISPR variants having nickase activity or nuclease dead variant. Furthermore, a CRISPR polypeptide variant according to the present disclosure can be codon-optimized to adapt the CRISPR polypeptide to the codon usage of a target cell, preferably a eukaryotic cell, preferably an animal or a plant cell.

In one embodiment according to the above aspect, the CRISPR polypeptide can be a catalytically active fragment of a wild-type CRISPR polypeptide provided that the CRISPR polypeptide still exerts the catalytic function of the wild-type CRISPR polypeptide, and/or the CRISPR polypeptide can be codon optimized, and/or the CRISPR polypeptide can be linked to a tag sequence, wherein the tag can be selected from the group consisting of a polyhistidin(His)-Tag, a glutathione-S-transferase (GST)-tag, a thioredoxin-tag, a FLAG-tag, a Tag having fluoresecent properties, for example, selected from (E)GFP ((enhanced) green fluorescent protein) tag, a DsRed-tag, a mCherry-tag, a (t)dtomato-tag, an mNeonGreen-tag and the like or, a streptavidin or strep-tag, a maltose-binding protein (MBP) tag, a transit peptide allowing the targeting to a subcellular compartment, including mitochondria or the nucleus, a snap-tag and/or a secretion tag allowing the secretion of an amino acid sequence attached thereto, a non-natural amino acid not normally occurring in nature, or a combination of the aforementioned tags, and/or the CRISPR polypeptide can be a modified CRISPR peptide functioning as DNA nickase, and/or the CRISPR polypeptide, or the catalytically active fragment thereof, can be present in the form of a fusion molecule with another functional moiety, preferably a functional polypeptide moiety having enzymatic function, preferably a functional moiety having chromatin modeling function, and/or stimulating homologous recombination, and/or modifying transcription. When analyzing at least one modified cell within a tissue of a multicellular organism, such tags and marker proteins, especially fluorescent protein tags, are preferred which have a bright fluorescence so that they can be even be determined in deeper layers of complex tissues. Suitable fluorescent proteins are commercially available and can be easily selected for the specific purpose by the skilled person.

According to the various embodiments of the present invention, either the CRISPR polypeptide(s) and/or the hybrid CRISPR nucleic acid sequence/DNA nucleic acid sequence(s) may comprise at least one nuclear localization sequence, and/or a plastid localization sequence, for example a mitochondria localization sequence or a chloroplast localization sequence, for efficient targeting of the CRISPR polypeptide to a cellular compartment comprising a genomic DNA sequence of interest to be modified. Sequence requirements for such localization sequences are known to the skilled person in the field of molecular biology. Not to hamper the function of the CRISPR polypeptide or of the hybrid RNA/DNA nucleotide sequence, the localization sequence is fused, i.e. covalently linked, to the N-terminal or C-terminal part, or correspondingly the 5' or 3' end of the respective molecule.

In one embodiment, the CRISPR polypeptide may be provided as polypeptide sequence produced ex vivo, either using recombinant technologies for protein production or via synthesis of the corresponding amino acid sequence. In another embodiment, the CRISPR polypeptide is presented as RNA sequence, which can be translated to the corresponding amino acid sequence upon introduction of a target cell of interest. In yet a further embodiment, the CRISPR polypeptide may be inserted as DNA construct, either configured for stable expression or for transient expression in a cell of interest, so that the CRISPR polypeptide is then transcribed and translated in a target cell of interest in a constitutive or inducible way. Suitable DNA constructs and associated methods for introducing a CRISPR polypeptide according to the present invention into a target cell are known to the skilled person, whereas specific ways of introducing a CRISPR polypeptide according to certain embodiments of the present invention specifically adapted for the application in plant cells are further detailed below.

The molecular complex, or the parts thereof, i.e. the at least one CRISPR polypeptide, the at least one CRISPR nucleic acid sequence and the at least one RT, or the constructs encoding the same, have to be introduced into a target cell of interest using a suitable delivery construct. Naturally, the type of delivery construct can vary, depending on the fact whether the molecular complex is fully assembled in vitro and later on introduced into a target cell, or whether the different components of the molecular complex are separately introduced into a cell and the complex is then assembled by non-covalent interactions within a target cell of interest. Introduction usually takes place by using a suitable delivery construct.

The term "delivery construct" or "(delivery) vector" as used herein according to various embodiments of the different aspects of the present invention refers to any biological or chemical, or non-chemical or particle-based means and/or methods used as a cargo for transporting a nucleotide and/or an amino acid sequence of interest into a target eukaryotic cell. Suitable delivery constructs comprise biological means for delivering nucleotide sequences into a target cell, including viral vectors, *Agrobacterium* spp., cell-penetrating peptides (CPPs) or chemical delivery constructs, including nanoparticles, nanocrystals, lipid or polymeric vesicles, calcium phosphate, or combinations thereof. Lipid or polymeric vesicles may be selected, for example, from lipids, liposomes, lipid encapsulation systems, nanoparticles, e.g. mesoporous silica nanoparticles, small nucleic acid-lipid particle formulations, polymers, e.g. cationic polymers like DEAE-dextran or polyethylenimine and polymersomes. In one embodiment, the polymer is selected from the group consisting of linear polymers, branched polymers, dendrimers (highly branched organic compounds), and polysaccharides. In another embodiment, the lipid encapsulation system comprises one or more of a phospholipid, cholesterol, polyethylene glycol (PEG)-lipid, and a lipophilic compound that delivers the particle to the target tissue. In a further embodiment, the delivery construct can be a mesoporous silica nanoparticle. Nanoparticles and nanocrystals generally have a small particle size of less than about 100 nm, less than about 50 nm, optionally less than about 20 nm, and in some aspects, less than 10 nm. Useful non-limiting examples for nanoparticles include magnesium oxide, and metal based nanoparticles, comprising gold, silver, and the like. Suitable active agent nanocrystals include magnetite ($Fe_3O_4$).

For example, cationic complexes from poly(aspartamide) derivatives bearing 1,3-diaminopropane side chains or 1,2-diaminoethane side chains can be used as cationic polymers, wherein 1,2-diaminoethane side chains might be preferred for certain applications due to their minimal cytotoxicity (Miyata et al., J. Am. Chem. Soc., 2008, 130(48):16287-94). To improve the delivery of the DNA and/or RNA into the cell, the respective nucleic acid must be protected from damage and its entry into the cell must be facilitated. To this end so-called lipoplexes and polyplexes have been created that have the ability to protect the nucleic acid from undesirable degradation during the transfection process (Tros de Illarduya et al., Eur. J. Pharm. Sci., 2010, 40(3):159-70.). These complexes form from cationic liposomes or polymers and represent an alternative for viral vector delivery, particularly in the area of gene therapy, where the disadvantage of inflammatory and immune response associated with viral vectors like lentivirus or AAV is sometimes to severe to use the high nucleic acid transfer efficiency of said viral vectors. Due to their characteristics of protecting nucleic acids from degradation and allowing high transfection efficiencies, lipoplexes and polyplexes are suitable for delivering any hybrid nucleic acid or molecular complex according to the present disclosure into a cell of interest.

According to the present invention, any delivery particle, e.g., micro- or nanoparticle, may have multiple functionalized surface domains. The particles include a core structure having a surface; a plurality of first linkers, e.g., heterofunctional linkers, each including a first end that binds to the surface of the core structure, and a second end that includes a first functional group; and a plurality of second linkers, e.g., heterofunctional linkers, each including a first end that binds to the surface of the core structure, and a second end that includes a second functional group, different than the first; wherein the linkers are bound to the surface of the core structure via their respective first ends (and can extend outwards from the core surface), and wherein the first and second functional groups form an external mosaic of surface domains, each domain including a majority of one type of functional group. The new particles can include pluralities of three, four, or more of the linkers. In some embodiments, the first and second linkers can be the same except for the different functional groups. In certain embodiments, the particles can include three or more different linkers. In various embodiments, the linkers can be or include a lipid, a surfactant, a polymer, a hydrocarbon chain, or an amphiphilic polymer. For example, the linkers can be or include polyethylene glycol or polyalkylene glycol. In certain embodiments, the first ends of the linkers include a lipid bound to polyethylene glycol (PEG) and the second ends comprise functional groups bound to the PEG.

In certain embodiments, transfection or transduction methodologies may be used which use combined or multi-domain delivery techniques as detailed above. In one embodiment, at least one CPP may be associated with a further domain in a functional way to provide a delivery vehicle suitable to transfect a hybrid nucleic acid sequence, a CRISPR polypeptide, or a molecular complex according to the present invention into a target cell of interest. A delivery vehicle may thus comprise an endosome leakage domain (ELD) linked to CPP domain to increase the transfection/transduction efficiency of a construct or complex into the cytosol or another compartment of a target cell of interest. In some embodiments, the delivery vehicle may comprise an endosome leakage domain (ELD) for facilitating endosome escape and access to the cytoplasmic compartment. As used herein, the expression "endosome leakage domain" refers to a sequence of amino acids which confers the ability of endosomally-trapped macromolecules to gain access to the cytoplasmic compartment. Without being bound by theory, endosome leakage domains are short sequences (often derived from viral or bacterial peptides), which are believed to induce destabilization of the endosomal membrane and liberation of the endosome contents into the cytoplasm. As used herein, the expression "endosomolytic peptide" is intended to refer to this general class of peptides having endosomal membrane-destabilizing properties. Accordingly, in some embodiments, synthetic peptide or polypeptide-based shuttle agents of the present description may comprise an ELD which is an endosomolytic peptide. Suitable ELDs for use as part of a delivery vehicle according to the present disclosure are disclosed in US 2016/0298078 A1 and comprise peptides that disrupt membranes at acidic pH, such as pH-dependent membrane active peptide (PMAP) or a pH-dependent lytic peptide. For example, the peptides GALA and INF-7 are amphiphilic peptides that form alpha helixes when a drop in pH modifies the charge of the amino acids which they contain. More particularly, without being bound by theory, it is suggested that ELDs such as GALA induce endosomal leakage by forming pores and flip-flop of membrane lipids following conformational change due to a decrease in pH (Kakudo, Chaki et al., 2004, Li, Nicol et al., 2004). In contrast, it is suggested that ELDs such as INF-7 induce endosomal leakage by accumulating in and destabilizing the endosomal membrane (El-Sayed, Futaki et al., 2009). Accordingly in the course of endosome maturation, the concomitant decline in pH causes a change in the conformation of the peptide and this destabilizes the endosome membrane leading to the liberation of the endosome contents. The same principle is thought to apply to the toxin A of *Pseudomonas* (Varkouhi, Scholte et al., 2011). Following a decline in pH, the conformation of the domain of translocation of the toxin changes, allowing its insertion into the endosome membrane where it forms pores (London 1992, O'Keefe 1992). This eventually favours endosome destabilization and translocation of the complex outside of the endosome. Furthermore, an ELD may be an antimicrobial peptide (AMP) such as a linear cationic alpha-helical antimicrobial peptide (AMP) or a peptide derived from such a sequence, or an ELD may be an antimicrobial peptide (AMP) such as Cecropin-A/Melittin hybrid (CM series) peptide, or a peptide derived from such a sequence. Such peptides are thought to be among the smallest and most effective AMP-derived peptides with membrane-disrupting ability. Cecropins are a family of antimicrobial peptides with membrane-perturbing abilities against both Gram-positive and Gram-negative bacteria. Cecropin A (CA), the first identified antibacterial peptide, is composed of 37 amino acids with a linear structure. Melittin (M), a peptide of 26 amino acids, is a cell membrane lytic factor found in bee venom. Cecropin-melittin hybrid peptides have been shown to produce short efficient antibiotic peptides without cytotoxicity for eukaryotic cells (i.e., non-hemolytic), a desirable property in any antibacterial agent. These chimeric peptides were constructed from various combinations of the hydrophilic N-terminal domain of Cecropin A with the hydrophobic N-terminal domain of Melittin, and have been tested on bacterial model systems. Two 26-mers, CA(1-13)M(1-13) and CA(1-8) M(1-18) (Boman et al., 1989), have been shown to demonstrate a wider spectrum and improved potency of natural Cecropin A without the cytotoxic effects of melittin. In some embodiments, the ELD may be a peptide derived from the N terminus of the HA2 subunit of influenza hemagglutinin (HA), which may also cause endosomal membrane destabilization when accumulated in the endosome.

Physical introduction methods as used herein and as suitable for providing at least one molecular complex or at least one hybrid RNA/DNA nucleic acid sequence according to the present invention refer to electroporation, microinjection, particle bombardment, sonoporation, magnetofection or impalefection using elongated nanostructures and arrays of such nanostructures such as carbon nanofibers or silicon nanowires which have been functionalized with plasmid DNA, and chemical methods and can rely on the use of micro- or nanoparticles or chemicals, including polyethylenglycol (PEG).

For example, for an embodiment, where the components of the molecular complex are associated ex vivo, the delivery vector can be a lipid-based or a polymeric vector. Lipid-based or polymeric vectors may be selected, for example, from lipids, liposomes, lipid encapsulation systems, microparticles, whiskers, nanoparticles, small nucleic acid-lipid particles, polymers, and polymersomes. In some embodiments, the polymer can be selected from the group consisting of linear polymers, branched polymers, dendrimers, and polysaccharides. In another embodiment, the lipid encapsulation system comprises one or more of a phospholipid, cholesterol, polyethylene glycol (PEG)-lipid, and a lipophilic compound that delivers the particle into a target cell.

For mammalian cells, ex vivo modification of immune cells for various therapeutic purposes has gained a lot of interest during the last decade to combat several tumor diseases by adoptively transferring specifically modified lymphocytes, preferably T-cells. Especially $CD8^+$ T-cell lymphocytes are interesting targets in this regard. It was described that immune responses derived from single naïve T cells, single primary, and single secondary central memory T cells reached similar size and phenotypic diversity, were subjected to comparable stochastic variation, and could ultimately reconstitute immunocompetence against an otherwise lethal infection with a bacterial pathogen as measured by in vivo fate mapping of $CD8^+$ T cells and their descendants across three generations of serial single-cell adoptive transfer and infection-driven re-expansion (Gräf et al., Immunity, 41, 116-126, 2014). After de novo thymic T-cell development from hematopoietic cells fully mature antigen-specific T-cells can be maintained over extensive periods of time in an individual, wherein the antigen can be a foreign antigen, e.g. an antigen expressed on a virus or a cancer cell. Targeted modification of such effector T-cells, or the precursors thereof, thus represents an important strategy to provide suitable T-cells for immunotherapy. Naïve T cells differentiate through a stage called stem cell memory T-cells, which give rise to central memory T-cells and effector memory T-cells and finally effector T-cells, wherein the effector T-cells represent terminally differentiated cells which can ultimately recognize and destroy a target cell. Effector memory and effector T-cells are the subsets of T cells that have the capacity to traffic to peripheral tissues. Another subset, tissue-resident memory T-cells are presently suggested, which do not circulate any more (cf., e.g., Farber et al., Nature Reviews Immunology, 14, 24-35, 2014).

Furthermore, immunotherapy of cancers has provided some of the first spectacular clinical cases showing that adoptive transfer of T cells expressing recombinant tumor-reactive receptors can cure otherwise treatment-resistant malignancies (Brentjens et al., 2013; Grupp et al., 2013; Porter et al., 2011) and that the use of engineered T cells in adoptive transfer therapies has shown significant promise in treating cancers, particularly haematological cancers. More and more, genetically modified T-cells of defined subset and phenotypic composition are used to increase cancer immunotherapy success (see Riddell et al., Cancer J., 20(2), 141-144, 2014). The use of chimeric antigen receptor-modified T cells as a therapy for hematologic malignancies and also for solid tumors is becoming more widespread. To this end, T cells are modified to express tumor-directed chimeric antigen receptors (CARs) (see e.g. Anurathapan et al., Molecular Therapy, 22, 623-633, 2014). Also so-called second generation CARs, e.g. CD19-targeted CARs that incorporate CD28 or 4-1BB signalling domains, for retargeting and reprogramming T cells to augment their antitumor efficacy are becoming more and more important (see e.g. Sjoukje et al., Nature Reviews Drug Discovery, 14, 499-509, 2015).

To test the capacity of a hybrid nucleic acid sequence, or a molecular complex according to the present invention for its suitability in mediating a gene edit with high precision, a variety of mammalian cell lines (adherent or suspension culture) are available to the skilled person and can be obtained from the American Type Culture Collection (ATCC), or from the Leibniz Institute German Collection of Microorganisms and Cell Cultures (DSMZ). Cell lines include HeLa, HEK293 cells, including HEK293T and HEK293A cells, THP-1, CHO, NIH3T3, CA46, Balb3T3 and HT2 cells. Additionally, primary cell cultures can be obtained from a mammal to test a hybrid nucleic acid sequence, or a molecular complex according to the present invention for its genome engineering capacity in a cell type of interest. Culture media, culture conditions and additives to cultivate and maintain a cell culture of interest are available to the skilled person by following the manufacturer's instructions.

Therefore, the hybrid RNA/DNA nucleic acid sequences according to the present invention represents an important tool to modify one or more mammalian cells in vivo or ex vivo, preferably for the treatment of a disease. For example, a lymphocyte cell, more preferably a T-cell or natural killer (NK) cell of any developmental stage to alter a T-cell or NK-cell expressed gene to influence T cell or NK-cell proliferation, survival and/or function with high precision to avoid off-target effects, which could be detrimental for a therapeutic application of the modified cell or cell population.

Similarly, the hybrid RNA/DNA nucleic acid sequences according to the present invention can represent a useful tool for modification of genetic material in livestock or other animal cells. For example, the correction of genetic diseases or editing for favorable characteristics such as meat, milk, e.g. milk with a reduced lactose content, or egg production in livestock or poultry.

In one embodiment there is thus provided a method for generating a population of immune cells of an animal comprising introducing a hybrid nucleic acid construct according to the present invention into at least one immune cell of interest, in vivo or ex vivo, to treat a disease, preferably an autoimmune disease, e.g. Type I diabetes or rheumatoid arthritis, or a proliferative disease, such as a cancer.

The preferred tissues of most plant species forming targets for genome editing are immature embryos, embryogenic callus, meristems of intact plants, pollen, pollen tube or egg cells, suspension cells, or other cell types with regenerative potential. For some plants the preferred tissues can be protoplasts or leaves. Any cell that can be treated and then regenerated into a whole plant can be considered a preferred tissue or cell. The protocols for tissue preparation, regeneration, and DNA delivery are different depending on species, tissue type, delivery method and other factors. A common delivery method is particle bombardment of cells with DNA- or protein-coated gold or tungsten particles. Other delivery methods are polyethylene glycol (PEG)-mediated transformation, electroporation, viral infection, direct injection into cells, and *Agrobacterium*-mediated transformation. In some plants delivery can be made into fertilized egg cells by slicing through the style shortly after fertilization and applying a liquid with the editing reagents into the cut pollen tube. For animal cells, preferably mammalian cells, electroporation, i.e. a transfection technology based on the momentary creation of small pores in cell membranes by applying an electrical pulse, might represent a suitable approach for introducing the at least one molecular complex according to the present invention. Several cell-type specific protocols for direct transfection success with a multitude of different cell types, including mammalian primary cells, stem cells and hard to transfect cell lines, are available to the skilled person, which are suitable as delivery tools for the at least one molecular complex according to the present invention. It is important to note that the combination of two or more methods or agents suitable for delivery may provide superior results depending on the cell type the genome of which has to be edited and is thus included within the scope of the present invention.

The preferred delivery method is to assemble in vitro the CRISPR nucleic acid sequence-RT hybrid nucleic acid and then load this hybrid into an in vitro produced and optionally purified CRISPR polypeptide before applying it to the target cells of interest. However, other useful delivery methods could be delivery of the CRISPR polypeptide as mRNA or as a genetic DNA construct, optionally comprising further regulatory elements, into the at least one target cell for transcription and/or expression in vivo, together with application of the hybrid nucleic acid simultaneously, before or especially after the CRISPR polypeptide delivery. In the case of non-covalent association of the CRISPR nucleic acid sequence with the RT component, these molecules can also be delivered separately; the CRISPR nucleic acid sequence can be delivered as RNA or as a DNA expression cassette that can be transcribed in vivo. In cases where the at least one CRISPR polypeptide or the at least one CRISPR nucleic acid sequence is delivered as an expression cassette, it may be preferable to express them from an RNA or DNA viral replicon or viral vector, particularly, when the target cell is a plant cell.

In a preferred embodiment according to the second aspect of the present invention, wherein the at least one molecular complex is associated ex vivo, the different components of the complex, i.e. the at least one hybrid nucleic acid, comprising at least one CRISPR nucleic acid sequence and at least one repair template nucleic acid, as well as at least one CRISPR polypeptide are synthesized, either chemically, or recombinantly, ex vivo/in vitro and the different components are then purified, preferably before assembly. An additional purification step can be performed after assembly of the at least one molecular complex according to the present invention. Methods for purifying nucleic acids, including DNA and RNA, or polypeptides, or ribonucleo- and ribonucleoprotein-complexes are readily available to the skilled person. The provision of a highly pure and stochiometric molecular complex, which can optionally be analyzed in vitro, allows the provision of precise genome editing tools with high efficiency.

In a further embodiment according to the various aspects according to the present invention, a conventional repair template nucleic acid sequence, either in the form of a plasmid or in the form of a nucleic acid oligonucleotide can be used in addition to the hybrid RNA/DNA nucleic acid to further increase the efficiency of the targeted genome editing event. Usually, the decisive factor whether a plasmid or another double-stranded DNA repair template is applied or whether a single-stranded oligonucleotide is used as repair template depends on the size of the intended modification to be introduced. The skilled person can easily define a further conventional repair template which can be used in addition to the hybrid nucleic acid construct according to the present invention. Those conventional repair templates can be introduced into at least one target cell of interest by a delivery vector, for example a geminiviral vector, in case the target cell is a plant cell, or by direct transfection or introduction as also detailed herein for the introduction of the hybrid RNA/DNA nucleic acid sequence according to the present invention.

In a further aspect according to the present invention there is provided a kit comprising the at least one component, wherein the component comprises molecular complex according to the second aspect of the present invention and further including suitable buffers and reagents, wherein the at least one molecular complex can be provided as preassembled complex, or preferably wherein the at least one molecular complex can be provided in the form of its separate constituents, comprising at least one CRISPR polypeptide, at least one CRISPR nucleic acid sequence and at least one repair template nucleic acid sequence. The separate provision of the different constituents of the molecular complex, preferably in the form of a dried or lyophilized powder for nucleic acid sequences, guarantees a higher stability of the nucleic acid sequences of the hybrid RNA/DNA construct, as especially RNA sequences are much less stable than polypeptides. The CRISPR protein can be delivered within a suitable storage buffer, e.g. comprising 300 mM NaCl, 10 mM Tris-HCl, 0.1 mM EDTA, 1 mM DTT, 50% Glycerol, pH 7.4 at 25° C. for a Cas9 polypeptide. The kit can further comprise a suitable reaction buffer including suitable ions, e.g. $Mg^{2+}$ for a Cas9 enzyme, required for the activity of a respective CRISPR polypeptide. Furthermore, for embodiments, where the kit comprises labeled or otherwise modified components, the kit can comprise additional buffers and chemicals to assist and/or induce the association (covalent linkage or non-covalent association) of the components after transfection of the components into a cell of interest. In another embodiment, the kit can comprise a container comprising a delivery construct or vehicle as disclosed herein to transfect, transduce or transform the at least one component of the molecular complex of the present invention, simultaneously or subsequently, into a target cell of interest. Alternatively, the kit can comprise the CRISPR components as lyophilized mRNA or as lyophilized protein, respectively. In a further embodiment according to this aspect, the kit can comprise a further component providing a suitable delivery vehicle or delivery system in addition to a component comprising the CRISPR component(s) as molecular complex. In a further embodiment according to this aspect, a CRISPR polypeptide and a hybrid nucleic acid sequence are presented as at least two components. The CRISPR polypeptide can be presented as vector to be transformed or transfected into a cell of interest, whereas the hybrid nucleic acid sequence, comprising at least one CRISPR nucleic acid sequence and at least one repair template, can be presented as separate component. A kit according to the present disclosure can thus be suitable for the simultaneous or subsequent use of the different components in case more than one component is present. Optionally a kit according to this aspect can comprise instructions for use, particularly instructions for use specific for a target cell to be edited. In a further preferred embodiment according to this aspect of the present invention, the kit is specifically developed to provide a trait development kit for a specific plant of interest including specific tools to achieve the desired trait modification. According to this embodiment, the kit comprises a specific repair template, which is configured to transfer the trait of interest into a DNA target locus of interest in a plant cell. In addition, the kit comprises a suitable CRISPR enzyme, or two CRISPR nickases, associated as molecular complex with at least one CRISPR nucleic acid sequence, wherein the CRISPR nucleic acid sequence comprises at least one first sequence portion that is complementary to a first DNA target sequence and a second sequence portion configured to interact with the at least one CRISPR polypeptide, and wherein the at least one CRISPR nucleic acid sequence is configured to be associated with or to be able to associate with a repair template carrying the specific trait of interest. As the kit according to this embodiment is both plant cell as well as trait specific, the use of said kit allows the rapid targeting and modification of a genomic DNA locus of interest to achieve trait development, as the CRISPR nucleic acid sequence components are already designed to interact with PAM motifs and a CRISPR enzyme of interest and the provided repair template presents the sequence to be inserted or modified in a convenient way.

In one aspect according to the present invention there is thus provided a plant, plant cell, a plant material, or a derivative, or a progeny thereof comprising or edited by at least one hybrid nucleic acid sequence according to the first aspect, or comprising the at least one molecular complex according to the second aspect of the present invention. In a further aspect according to the present invention there is provided a plant, plant cell, a plant material, or a derivative, or a progeny thereof that has been modified with a hybrid nucleic acid complex.

In yet a further aspect according to the present invention there is provided a method of modifying at least one DNA target sequence in a prokaryotic or eukaryotic cell (i) providing at least one prokaryotic or eukaryotic cell comprising at least one DNA target sequence comprising at least one first and at least one second DNA target sequence in a genomic region of interest; (ii) providing at least one molecular complex as detailed for the second aspect of the present invention comprising at least one hybrid nucleic acid sequence as detailed for the first aspect of the present invention and at least one CRISPR polypeptide; (iii) contacting the at least one molecular complex with the at least one DNA target sequence under suitable conditions to achieve complementary base pairing of the first sequence portion of the CRISPR nucleic acid sequence of the at least one hybrid nucleic acid sequence with the at least one first DNA target sequence to achieve recognition of the first DNA target sequence by the at least one CRISPR polypeptide and optionally induction of at least one DNA break by the at least one CRISPR polypeptide, wherein the at least one repair template nucleic acid sequence of the at least one hybrid nucleic acid sequence directs homology directed repair at the site of the at least one second DNA target sequence; and (iv) obtaining at least one prokaryotic or eukaryotic cell comprising a modification in the at least one DNA target sequence.

In one embodiment, the at least one hybrid nucleic acid sequence of the molecular complex may be provided to the at least one prokaryotic or eukaryotic cell independently of the at least one CRISPR polypeptide of the at least one molecular complex and the at least one molecular complex is assembled within the at least one prokaryotic or eukaryotic cell.

The at least one molecular complex, as detailed above, can be provided as in vitro assembled complex which is then introduced into at least one target cell of interest. Alternatively, some or all of the at least one CRISPR polypeptide and/or the at least one CRISPR nucleic acid sequence and/or the at least one repair template nucleic acid sequence can be inserted as genetic RNA or DNA construct and can be produced in vivo so that the final assembly of the at least one molecular complex takes place in vivo. In a preferred embodiment, the at least one molecular complex is associated ex vivo and the at least one molecular complex comprising at least one CRISPR polypeptide, at least one CRISPR nucleic acid sequence and at least one repair template nucleic acid sequence is then simultaneously provided to the at least one cell by a suitable delivery vector allowing the functional introduction of the at least one molecular complex into the at least one target cell comprising at least one DNA target sequence of interest.

"Suitable conditions" or "suitable reaction conditions" as referred to herein in the context of the methods according to the present disclosure refer to conditions, which allow both, the growth and development of a cell or organism, including prokaryotic or eukaryotic cells, being transformed or manufactured and the conditions necessary for achieving either stable integration or transient introduction of a genetic construct of interest in the at least one cell or organism of interest. Conditions to promote prokaryotic or bacterial growth and/or transformation are known to the skilled person (see also: Green and Sambrook, Molecular Cloning, A Laboratory Manual, 2012, Cold Spring Harbor Laboratory Press). Conditions to promote animal cell growth and/or for introducing genetic material into animal, particularly mammalian cells, are available to the skilled person for a variety of different cell lines (see Green and Sambrook supra). Conditions to promote plant or plant cell growth and development, including inter alia temperature, light, water, oxygen, mineral nutrients and soil support, which can vary for different plant species and can be readily determined by the skilled person in knowledge of the disclosure provided herein. The further suitable conditions to achieve stable integration or transient introduction of at least one molecular complex of interest depend on the transformation method selected for introduction of at least one molecular complex of interest, the developmental stage of the plant material or plant cell to be transformed and at least one molecular complex of interest to be introduced. Said suitable conditions can be defined by the skilled person in light of the present disclosure defining the suitable conditions for the methods in combination with exemplary molecular complexes and suitable delivery vectors and delivery techniques as disclosed and claimed herein.

In one embodiment according to the above method of the present invention, the at least one eukaryotic cell is a plant cell, preferably a plant cell from a plant selected from the group consisting of *Hordeum vulgare, Hordeum bulbusom, Sorghum bicolor, Saccharum officinarium, Zea mays, Setaria italica, Oryza minuta, Oriza sativa, Oryza australiensis, Oryza alta, Triticum aestivum, Triticum durum, Secale cereale, Triticale, Malus domestica, Brachypodium distachyon, Hordeum marinum, Aegilops tauschii, Daucus glochidiatus, Beta vulgaris, Daucus pusillus, Daucus muricatus, Daucus carota, Eucalyptus grandis, Nicotiana sylvestris, Nicotiana tomentosiformis, Nicotiana tabacum, Nicotiana benthamiana, Solanum lycopersicum, Solanum tuberosum, Coffea canephora, Vitis vinifera, Erythrante guttata, Genlisea aurea, Cucumis sativus, Morus notabilis, Arabidopsis arenosa, Arabidopsis lyrata, Arabidopsis thaliana, Crucihimalaya himalaica, Crucihimalaya wallichii, Cardamine flexuosa, Lepidium virginicum, Capsella bursa pastoris, Olmarabidopsis pumila, Arabis hirsute, Brassica napus, Brassica oleracea, Brassica rapa, Raphanus sativus, Brassica juncacea, Brassica nigra, Eruca vesicaria* subsp. *sativa, Citrus sinensis, Jatropha curcas, Populus trichocarpa, Medicago truncatula, Cicer yamashitae, Cicer bijugum, Cicer arietinum, Cicer reticulatum, Cicer judaicum, Cajanus cajanifolius, Cajanus scarabaeoides, Phaseolus vulgaris, Glycine max, Gossypium* sp., *Astragalus sinicus, Lotus japonicas, Torenia foumieri, Allium cepa, Allium fistulosum, Allium sativum, Helianthus annuus, Helianthus tuberosus* and *Allium tuberosum*, or any variety or subspecies belonging to one of the aforementioned plants.

Concerning plant cells as targets, for example, a variety of transformation and/or transfection methods is available to the skilled person in the field. For maize protoplasts, for example, a suitable method is disclosed in Sheen, J. 2002. A transient expression assay using maize mesophyll protoplasts. For *Arabidopsis* protoplasts, a suitable protocol is available (Retrieved from the Internet <URL: http://dx-.doi.org/10.1038/nprot.2007.1991 For tobacco and other dicot protoplasts, a suitable protocol is available (ronlinel. Retrieved from the Internet <URL: www.plantphysiol.org/cgi/doi/10.1104/pp. 112.2051791. The skilled person having knowledge of the present disclosure and being aware of the cited protocols can thus define a suitable method for introducing a molecular complex according to the present invention into a plant protoplast derived from a monocot or a dicot plant.

Protoplasts are very useful for testing gene editing technologies and reagents, but for regeneration of gene edited plants they are not always the preferred cell type, as very few plant species regenerate efficiently from protoplast. In these cases the preferred tissues for most plant species are immature embryos, embryogenic callus, fertilized embryos, meristems of intact plants, pollen, pollen tube or egg cells, embryogenic suspension cells, or other cell types with regenerative potential. A common physical delivery method is particle bombardment of cells with DNA- or protein-coated gold or tungsten particles, whereas a common biologically assisted method uses *Agrobacterium* or a (modified) viral vector as disclosed herein.

"Meristematic cell(s)" as referred to according to the present disclosure belong to a tissue type within a plant which is also referred to as meristem or cambium or formative tissue. Like stem cells in animal organisms, meristematic cells of plants representing undifferentiated cells have the intrinsic capability to develop and differentiate into specialized cell types, depending on genetic predisposition and further environmental and developmental factors. In plant organisms, meristems are not only present during the embryo development, but they can be found during the whole life cycle of a plant so that a targeted genetic modification of meristematic cells or tissues according to the present disclosure is not restricted to plant embryos or seedlings, but it can rather also be conducted in larger seedlings and more mature plants, for example when targeting meristems which build the basis for the reproductive plant organs, for example the tassel or ear in maize.

According to one embodiment according to the various aspects according to the present disclosure a meristematic cell can be a mature or immature plant cell of a plant embryo or seedling of a plant comprising at least one meristematic cell or meristematic tissue.

For certain genome editing approaches, a stable integration of the molecular complex encoding expression cassette (s) might be desirable, where a transgenic organism carrying a desired construct of interest, or a part thereof, can inherit a stably inserted construct to the progeny of a plant cell of interest initially transformed or transfected. Said stable integration can take place into any genomic region of an organism, preferably a eukaryotic organism, including the nuclear genome as well as the extranuclear genome, including the genome of plastids.

A transient introduction might be desirable, in case a certain effect is desired by the introduction of a molecular complex of interest, or a part thereof, but the construct per se should not be inherited to a progeny of the cell initially. Due to regulatory reasons, such an approach might be especially suitable for certain applications, particularly with plant cells, tissues, organs or material as structure comprising the DNA target sequence to be modified.

The term "targeted integration" or "functional integration" as used herein refers to the integration of a genetic construct of interest into at least one cell, which allows the transcription and/or translation and/or the catalytic activity and/or binding activity, including the binding of a nucleic acid molecule to another nucleic acid molecule, including DNA or RNA, or the binding of a protein to a target structure within the at least one cell. Where pertinent, the functional integration takes place in a certain cellular compartment of the at least one cell, including the nucleus, the cytosol, the mitochondrium, the chloroplast, the vacuole, the membrane, the cell wall and the like. Consequently, the term "functional integration"—in contrast to the term "stable integration" detailed above—implies that the molecular complex of interest is introduced into the at least one cell by any means of transformation, transfection or transduction by biological means, including *Agrobacterium* transformation, or physical means, including particle bombardment, as well as the subsequent step, wherein the molecular complex exerts its effect within or onto the at least one cell in which it was introduced. Depending on the nature of the genetic construct to be introduced, said effect naturally can vary and including, alone or in combination, inter alia, the transcription of a DNA encoded by the genetic construct to a ribonucleic acid, the translation of an RNA to an amino acid sequence, the activity of an RNA molecule within a cell, comprising the activity of a guide RNA, a crRNA, a tracrRNA, or an miRNA or an siRNA for use in RNA interference, and/or a binding activity, including the binding of a nucleic acid molecule to another nucleic acid molecule, including DNA or RNA, or the binding of a protein to a target structure within the at least one cell, or including the integration of a sequence delivered via a vector or a genetic construct, either transiently or in a stable way. Said effect can also comprise the catalytic activity of an amino acid sequence representing an enzyme or a catalytically active portion thereof within the at least one cell and the like. Said effect achieved after functional integration of the molecular complex according to the present disclosure can depend on the presence of regulatory sequences or localization sequences which are comprised by the genetic construct of interest as it is known to the person skilled in the art.

As detailed above, the methods according to the present invention targeting pluripotent or multipotent cells provide the advantage that both the transformation and the further development of a transformed at least one cell, particularly a meristematic cell, can take place in planta obviating the need for cumbersome in vitro cultivation steps for the regeneration of a plant or plant material therefrom. In certain embodiments, it might, however, be suitable to explant or dissect a plant cell, tissue, organ or material for further cultivation, screening or testing depending on the specific needs. Several methods for the in vitro cultivation of a plant cell, tissue, organ or material are available to the skilled person.

A stable integration might thus be desirable, where a transgenic plant carrying a desired construct of interest, or a part thereof, is stably inserted and the inserted construct or part thereof is inherited to the progeny of a plant cell of interest initially transformed. Said stable integration can take place into any genomic region of the plant, including the nuclear genome as well as the extranuclear genome, including the genome of plastids of a plant cell.

A transient introduction might be desirable, in case a certain effect, e.g. a silencing effect, a targeted manipulation, comprising a knock-in or a knock-out, is desired by the introduction of a genetic construct of interest, or a part thereof, but the construct per se should not be inherited to a progeny of the cell initially transformed, transfected or transduced.

In yet another embodiment of the above aspect according to the present invention, the introduction of the at least one molecular complex of interest, or parts thereof including the CRISPR nucleic acid sequence and/or the RT, may be conducted using a means selected from the group consisting of a device suitable for particle bombardment, including a gene gun, including a hand-held gene gun (e.g. Helios® Gene Gun System, BIO-RAD) or a stationary gene gun, transformation, including transformation using *Agrobacterium* spp. or using a viral vector, microinjection, electroporation, whisker technology, including silicon carbide whisker technology, and chemical, e.g. using calcium phosphate, dendrimers, liposomes or cationic polymers, and non-chemical, e.g. using electroporation, sonoporation, optical transfection using a laser, protoplast fusion, impalefection, hydrodynamic gene delivery of DNA by injecting a delivery construct into a an organ, preferably the liver, of an animal, preferably a rodent animal, transfection, or a combination thereof.

In certain embodiments, the at least one eukaryotic cell may be a meristematic plant cell, and the plant cell, after introduction of the molecular complex according to the present invention is further cultivated under suitable conditions until the developmental stage of maturity of the inflorescence is achieved to obtain a plant or plant material comprising a modification of interest mediated by the at least one molecular complex according to the present invention. Several protocols are, for example, available to the skilled person for producing germinable and viable pollen from in vitro cultured maize tassels, for example in Pareddy D R et al. (1992) Maturation of maize pollen in vitro. Plant Cell Rep 11 (10):535-539. doi:10.1007/BF00236273, Stapleton A E et al. (1992) Immature maize spikelets develop and produce pollen in culture. Plant Cell Rep 11 (5-6):248-252 or Pareddy D R et al. (1989) Production of normal, germinable and viable pollen from in vitro-cultured maize tassels. Theor Appl Genet 77 (4):521-526. Those protocols are inter alia based on excision of the tassel, surface sterilization and culture in a media with kinetin to promote tassel growth and maturation. After the spikelets are formed, a continuous harvest of anthers can be performed. After extrusion, anthers will be desiccated until the pollen comes out. Alternatively, anthers can be dissected and the pollen is shed in liquid medium that is subsequently used to pollinate ears.

"Maturity of the inflorescence" as used herein refers to the state, when the immature inflorescence of a plant comprising at least one meristematic cell has reached a developmental stage, when a mature inflorescence, i.e. a staminate inflorescence (male) or a pistillate inflorescence (female), is achieved and thus a gamete of the pollen (male) or of the ovule (female) or both is present. Said stage of the reproductive phase of a plant is especially important, as obtained plant material can directly be used for pollination of a further plant or for fertilization with the pollen of another plant.

In a further embodiment according to the above method of the present invention, the modification of the at least one DNA target sequence may be a genome editing approach selected from the group consisting of yield improvement, tolerance to abiotic stress, including drought stress, osmotic stress, heat stress, cold stress, oxidative stress, heavy metal stress, salt stress or waterlogging, tolerance to biotic stress including tolerance to insects, tolerance to bacteria, tolerance to viruses, tolerance to fungi or tolerance to nematodes, resistance to herbicides, including glyphosate, glufosinate, acetolactate synthase (ALS) inhibitors, and Dicamba, lodging resistance, flowering time, shattering resistance, seed color, endosperm composition, nutritional content, or metabolic engineering, including genome editing to allow a molecular pharming approach in at least one plant cell.

In another embodiment according to the above method of the present invention, the modification of the at least one DNA target sequence may be a genome editing approach for ex vivo modifying an immune cell in at least one eukaryotic cell, preferably a mammalian cell, preferably a mammalian leukocyte, for obtaining a modified cell suitable for treating a viral disease or for immunotherapy, especially cancer immunotherapy.

In one preferred embodiment the above method according to the present invention is a method for modifying a eukaryotic cell, preferably at least one plant cell, in a targeted way to provide a genetically modified, preferably non-transgenic plant, wherein the method may inter alia be a method for trait development. For example, a highly site-specific substitution of 1, 2, 3 or more nucleotides in the coding sequence of a plant gene can be introduced so as to produce substitutions of one or more amino acids that will confer tolerance to at least one herbicide such as glyphosate, glufosinate, Dicamba or an acetolactate synthase (ALS) inhibiting herbicide. Furthermore, in another embodiment, substitutions of one or more amino acids in the coding sequence of a nucleotide binding site-leucine-rich repeat (NBS-LRR) plant gene that will alter the pathogen recognition spectrum of the protein to optimize the plant's disease resistance. In yet a further embodiment, a small enhancer sequence or transcription factor binding site can be modified in an endogenous promoter of a plant gene or can be introduced into the promoter of a plant gene so as to alter the expression profile or strength of the plant gene regulated by the promoter. The expression profile can be altered through various modifications, introductions or deletions in other regions, such as introns, 3' untranslated regions, cis- or trans-enhancer sequences. In yet a further embodiment, the genome of a plant cell, preferably a meristematic plant cell, can be modified in a way so that the plant resulting from the modified meristematic cell, can produce a chemical substance or compound of agronomic or pharmaceutical interest, for example insulin or insulin analoga, antibodies, a protein with an enzymatic function of interest, or any other pharmaceutically relevant compound suitable as medicament, as dietary supplement, or as health care product.

Non limiting examples of traits that can be introduced by this method are resistance or tolerance to insect pests, such as to rootworms, stem borers, cutworms, beetles, aphids, leafhoppers, weevils, mites and stinkbugs. These could be made by modification of plant genes, for example, to increase the inherent resistance of a plant to insect pests or to reduce its attractiveness to said pests. Other traits can be resistance or tolerance to nematodes, bacterial, fungal or viral pathogens or their vectors. Still other traits could be more efficient nutrient use, such as enhanced nitrogen use, improvements or introductions of efficiency in nitrogen fixation, enhanced photosynthetic efficiency, such as conversion of C3 plants to C4. Yet other traits could be enhanced tolerance to abiotic stressors such as temperature, water supply, salinity, pH, tolerance for extremes in sunlight exposure. Additional traits can be characteristics related to taste, appearance, nutrient or vitamin profiles of edible or feedable portions of the plant, or can be related to the storage longevity or quality of these portions. Finally, traits can be related to agronomic qualities such resistance to lodging, shattering, flowering time, ripening, emergence, harvesting, plant structure, vigor, size, yield, and other characteristics.

In one embodiment according to the above method according to the present invention, the target cell may be a prokaryotic cell and the modification comprises at least one modification of a genomic target region of interest of at least one prokaryotic cell, wherein the modification is suitable to modulate or increase resistance of the *bacterium* against biotic or abiotic stress, including resistance against antibiotics, or wherein the modification is suitable to improve phage resistance of the at least one prokaryotic cell. In another embodiment, the modification may comprise inserting a gene of interest into a DNA target site of at least one prokaryotic cell of interest, e.g. to insert sequence encoding a fluorescent marker protein or another selectable marker into at least one DNA target site of interest. In another embodiment, the modification comprises knocking-out, i.e. deleting at least one DNA target site of interest in at least one prokaryotic cell. As prokaryotic cells will not further differentiate, but can directly inherit at least one introduce modification of interest to their progeny and as prokaryotic cells usually have a very short generation time in comparison to eukaryotic cells, a modification as introduced by at least one hybrid RNA/DNA in the form of at least one molecular complex according to the present invention can be accomplished quickly and the resulting population of modified cells can be obtained and analyzed in a very short time period.

On certain embodiments, the above method according to the present invention can further comprise the following step: (v) identifying and/or selecting at least one prokaryotic or eukaryotic cell comprising the modification in the at least one DNA target sequence.

Methods for analyzing or identifying a modification according to the present disclosure as effected in the genome of at least one prokaryotic or eukaryotic cell are known to the person skilled in the art and comprise, but are not limited to polymerase chain reaction (PCR), including inter alia real time quantitative PCR, multiplex PCR, RT-PCR, nested PCR, analytical PCR and the like, microscopy, including bright and dark field microscopy, dispersion staining, phase contrast, fluorescence, confocal, differential interference contrast, deconvolution, electron microscopy, UV microscopy, IR microscopy, scanning probe microscopy, the analysis of the metabolite of a cell, the analysis of an altered resistance spectrum of a modified cell, RNA analysis, proteome analysis, functional assays for determining a functional integration, e.g. of a marker gene or a transgene of interest, or of a knock-out, Southern-Blot analysis, sequencing, including deep sequencing and combinations thereof. Cells comprising the desired modification can then be selected for further cultivation or any other downstream manufacturing step.

In a further aspect according to the present invention there is provided a method for manufacturing a plant or plant cell a plant or plant cell comprising the following steps: (i) performing a method of modifying at least one DNA target sequence in a eukaryotic cell as detailed above, wherein the at least one eukaryotic cell is a plant cell; (ii) obtaining at least one plant or a progeny thereof from the at least one plant cell from step (i); (iii) optionally: determining the modification in the at least one DNA target sequence in the at least one cell of the at least one plant or a progeny thereof.

Suitable plant cells, tissues, organs and materials for performing this aspect are detailed above. The term "manufacturing" according to the present disclosure is to be construed broadly and comprises any form of genetic manipulation performed on the genetic material of a plant or plant cell. The provision of the at least one molecular complex comprising at least one hybrid nucleic acid sequence comprising at least one CRISPR nucleic acid sequence and at least one repair template nucleic acid and at least one CRISPR polypeptide can take place in a way to allow transient action or stable integration, or a combination thereof, of the different components as detailed above. Preferably, the at least one molecular complex, or the different components thereof, are provided in a transient way so that no integration of any of those effector components as such, including a sequence encoding a CRISPR RNA, a sequence encoding a repair template nucleic acid DNA, and a sequence encoding a CRISPR polypeptide, into the genome of target cell of interest takes place.

In one embodiment according to the above manufacturing method according to the present invention, the at least one plant or plant cell may be selected from a monocotyledonous or a dicotyledonous plant, preferably, wherein the plant is selected from the group consisting of *Zea* spp., including *Zea mays, Nicotiana benthamiana*, or *Beta* spp, including *Beta vulgaris*, or *Secale* ssp., including *Secale* cereal, or *Triticum* ssp., including *Triticum aestivum.*

As detailed throughout the present disclosure, the methods according to the present invention are suitable and can be adapted to target cells belonging to all kingdoms of life, as the gist of using a hybrid RNA/DNA construct which is associated in a functional way is species and cell independent, provided there is a homologous recombination mechanism for DNA repair in the cell, yet dictated by the covalent or non-covalent interaction of the at least on CRISPR nucleic acid sequence and the at least one RT. What has to be determined individually for each target cell and each target are (i) the CRISPR nucleic acid sequence and the CRISPR polypeptide, which have to be compatible as detailed above; (ii) a matching of the CRISPR nucleic acid sequence of interest with a PAM site within the DNA target region of interest; and (iii) the DNA target sequence and the target modification to be introduced. For any sequenced genome publicly available, the design of suitable nucleic acid sequences can thus be made in silico based in the disclosure of the present invention.

In yet a further aspect according to the present invention, there is provided the use of at least one hybrid RNA/DNA nucleic acid sequence according to the first aspect of the present invention, or use of a molecular complex according to the second aspect of the present invention for genome editing in a prokaryotic or a eukaryotic cell. In one embodiment of this aspect, the use is for a eukaryotic cell, preferably a fungal, an animal or a plant cell or organism.

According to the various aspects and embodiments according to the present invention, a eukaryotic cell or a method or use for modifying a eukaryotic cell does explicitly not include any process of cloning human beings, a process for modifying the germ line genetic identity of human beings or the use of human embryos, or a method needing the destruction of human embryos to gain cells therefrom.

The present invention is further described with reference to the following non-limiting examples.

EXAMPLES

The present invention is further illustrated by the following non limiting examples.

Example 1

Hybrid nucleic acid sequence suitable to be combined with a CRISPR polypeptide In one experiment, the tailed sgRNA or another suitable CRISPR nucleic acid are hybridized via both complementary base pairing and RNA-DNA ligation with a single stranded repair template. For covalent association, synthesized DNA oligonucleotides are covalently ligated to the 3' end of RNA oligonucleotides using the ssRNA ligase manufacturer's protocol. For non-covalent association, RNA and DNA oligonucleotides with partially complementary sequence are mixed and allowed to complex via Watson-Crick base pairing. Successful hybridization can be ascertained in gel shift assays. Treatment of aliquots of the hybrid nucleic acid with RNase and DNase enzymes prior to the gel shift assays indicates that some of the hybrid nucleic acid is composed of RNA and some of DNA. The nucleic acid hybrid is then complexed with a recombinant CRISPR polypeptide, e.g. Cpf1, Cas9, CasX or CasY protein. Successful complexing can be verified by treating with proteinase K, RNase, DNase and a mock treatment, and observing the relative gel shift patterns. Recombinant CRISPR polypeptides were produced and subsequently purified either through an external commercial entity or by in-house capability. Different architectures of hybrid nucleic acid sequences tested are shown in FIGS. 1a and 1b and FIG. 2.

Example 2: In Vitro Cutting of a DNA Target by a Complex of CRISPR Protein with a Hybrid RNA-DNA Nucleic Acid In one experiment, the functionality of the CRISPR protein, e.g. Cpf1, Cas9, CasX or CasY protein, as a site-specific endonuclease was tested when used with the nucleic acid hybrid technology described. A linearized plasmid containing at least one target site for the sgRNA or another suitable CRISPR nucleic acid was mixed with a CRISPR protein-CRISPR nucleic acid-RT complex (e.g. Cas9-sgRNA-RT complex) as described in the present invention. After incubation under conditions suitable for nuclease activity, including the right pH, temperature and cofactors and the like which are known to the skilled person for various CRISPR nucleases and variants thereof, the DNA target plasmid was run on an agarose gel and observed for band sizes indicating cutting a the expected target site. In vitro cleavage of the target DNA indicated that the RT associated with the sgRNA as "cargo" did not interfere with the normal function of the complex as a site-specific endonuclease.

Example 3: In Vivo Editing by CRISPR Protein Complexed with a Hybrid RNA-DNA Nucleic Acid To demonstrate that a target gene can be edited in vivo by a delivered complex comprising CRISPR protein, e.g. Cpf1, Cas9, CasX or CasY protein, and a hybrid RNA-DNA nucleic acid, a nonfunctional tdTomato gene contained within a transformed plasmid was repaired by exchanging a single nucleotide to restore the fluorescent signal from the tdTomato gene. To determine the optimal use for editing by provision of a ssDNA repair template with complementarity to the target strand or non-target strand, complexes carrying repair templates of either strand were compared.

The hybrid nucleic acid RNA/DNA-CRISPR polypeptide complex obtained in example 1 was used to repair an episomal plasmid target, encoding a tdTomato gene with a single point mutation from A to T that creates an early stop signal at codon position 51. This plasmid was introduced into a corn protoplast system together with the editing complex comprising CRISPR protein and a hybrid RNA-DNA nucleic acid through PEG- or electroporation-mediated delivery. A single-stranded repair template is then linked to the CRISPR nucleic acid like to the sgRNA through complementary base pairing. The repair template is complementary to the region ~80 base pairs downstream and ~40 base pairs upstream of the cut site. Successful editing then results in some cells displaying a tdTomato fluorescence phenotype due to repair of the tdTomato gene in at least one plasmid contained within them. The relative efficiency of editing with the different repair templates can thus easily be assessed by measuring the abundance of fluorescent cells resulting from each treatment.

Example 4: In Vivo Editing by CRISPR Protein Complexed with a RT Attached to the RNA Component by Covalent Attachment or Associated by Complementary Base Pairing To demonstrate editing with hybrid nucleic acid molecules manufactured in various ways, the optimal conditions identified in Example 3 were used to assess repair of the same episomal plasmid target with hybrid nucleic acids covalent linkage or non-covalent base pairing of the repair template to the sgRNA.

In case a marker, particularly a fluorescent marker is used, successful editing will result in some cells displaying a fluorescence phenotype due to repair of the fluorescence encoding gene, such as a tdTomato gene, in at least one plasmid contained within them. The relative efficiency of editing with the different repair templates can then be assessed by measuring the abundance of fluorescent cells resulting from each treatment.

Example 5: In Vivo Editing by CRISPR Protein Complexed with a Nucleic Acid Hybrid Formed by Linking the RT to the 5' or 3' End of the CRISPR Nucleic Acid (gRNA)

In one example, the method described in example 3 can be used to identify a preference for the repair template hybridized or linked to the 5' or 3' end of the sgRNA or another suitable CRISPR nucleic acid. The preferable linkage covalency determined in example 4 can be employed here. Based on results presented in Tsai et al. ("Dimeric CRISPR RNA-guided FokI nucleases for highly specific genome editing", Nature Biotechnology, 32, 569-576 (2014), doi:10.1038/nbt.2908) and further, Shechner et al. ("Multiplexable, locus-specific targeting of long RNAs with CRISPR-Display", Nature Methods, 12(7), 664-670 (2015), doi: 10.1038/nmeth.3433), a 3' fusion is expected to be preferable.

Successful editing results in some cells displaying a fluorescence phenotype, such as a tdTomato phenotype, due to repair of the tdTomato gene in at least one plasmid contained within them. The relative efficiency of editing with the different repair templates can then be assessed by measuring the abundance of fluorescent cells resulting from each treatment.

Example 6: Determining the Optimal Linker Length Between CRISPR Nucleic Acid and Repair Template for In Vivo Editing by CRISPR Protein Complexed with a Hybrid Nucleic Acid In one example, an increasing linker length in 50 base pair increments up to a length of 500 base pairs between gRNA and repair template was used to identify optimal conditions for homologous recombination to repair the target described in example 3. Employing a set of linker lengths will help determine the necessary flexibility needed within the hybrid to overcome the protein target strand geometry. This is particularly necessary, when working with different CRISPR nucleases and thus specific gRNAs and individual repair templates (RTs) to coordinate the interplay of the molecular complex and to guarantee that the CRISPR complex also in the presence of the RT can exert its effect. The conditions of example 3 were used together with the optimized parameters determined within the examples 3 through 5. The linker was DNA with complementarity to sequence near the target gene.

Successful editing will result in some cells displaying a tdTomato fluorescence phenotype, in case a tdTomato marker is used, due to repair of the tdTomato gene in at least one plasmid contained within them. The relative efficiency of editing with the different linker lengths can then be assessed by measuring the abundance of fluorescent cells resulting from each treatment. Likewise, any other selectable marker of interest can be used including any fluorescent marker suitable for a cell type of interest, antibiotic markers, tag sequences, regulatory sequences and the like.

Example 7: Determining the Optimal Configuration of the Repair Template for In Vivo Editing by CRISPR Protein Complexed with a Hybrid Nucleic Acid To demonstrate editing with single- and double-stranded repair templates, the in vivo assay described in example 3 was used for a relative comparison of the two configurations. Single stranded repair templates are expected to be better based on the lower molecular weight and published higher rates of editing with short ssDNA oligos than with short dsDNA oligos. However, using a double stranded repair template may be necessary in cases where large sequences need to be edited or inserted. The optimal conditions of examples 4 and 6 can be used in this example.

A successful editing event results in some cells displaying a fluorescence phenotype, such as a tdTomato phenotype, due to repair of the tdTomato gene in at least one plasmid contained within them. The relative efficiency of editing with the different repair templates can then be assessed by measuring the abundance of fluorescent cells resulting from each treatment.

Example 8: In Vivo Editing of a Chromosomal Target by CRISPR Protein Complexed with a Hybrid RNA-DNA Nucleic Acid In one example, the method optimized by examples 3 through 7 can be used to make edits to a chromosomal target gene. Here, a transgenic corn plant with a stable insertion of the early stop codon tdTomato cassette was used to demonstrate the utility of the invention for a chromosomal target. Successful editing resulted in some cells displaying a tdTomato fluorescence phenotype due to repair of the tdTomato gene integrated in the genomic DNA. The efficiency of editing was assessed by measuring the abundance of fluorescent cells resulting from each treatment.

Example 9: In Vivo Insertion of a Gene Cassette into a Chromosomal Target by CRISPR Protein Complexed with a Hybrid RNA-DNA Nucleic Acid To demonstrate the utility of the invention for insertion of a full length gene into a chromosomal target, a tdTomato fluorescent reporter gene and terminator were integrated into the hmg13 gene of corn, resulting in a tdTomato fluorescent signal due to expression driven by the endogenous promoter for hmg13. The results could demonstrate that long inserts can be made using the invented method and will help optimize the conditions for said insertion.

Successful editing results in some cells displaying a tdTomato fluorescence phenotype. This phenotype is caused by the insertion of the tdTomato gene into the hmg13 target and subsequent tdTomato protein expression. The corresponding efficiency of editing for each cell type tested can then be assessed by measuring the abundance of fluorescent cells resulting from each treatment.

Example 10: Use of a Cell Penetrating Peptide to Deliver into Plant Cells the Cas9 Protein Complexed with a Hybrid RNA-DNA Nucleic Acid The optimal system identified in examples 8 or 9 were used in this example to test the effectiveness of PEG based transformation versus transformation with a cell penetrating peptide (CPP). Previous publications and applications suggest that use of CPPs for delivery will enable introduction into cells with a cell wall the CRISPR protein, e.g. Cas9 or Cpf1 protein, complexed with a hybrid RNA-DNA nucleic acid. CPPs were thus used within a CRISPR fusion protein or linked to CRISPR protein though a disulfide bond formed between an N-terminal cysteine on the CRISPR protein and an N-terminal cysteine on the CPP. Free CPPs can also be used to aid the import of the CRISPR nucleic acid complex through transient binding on the nucleic acid strand. Initial CPPs can include the HIV TAT peptide (see e.g. SEQ ID NOs: 17 and 18), or a sequence derived therefrom and/or an $(Arg)_9$ sequence. The effectiveness can be tested using the optimized method of examples 3-9 through successful tdTomato expression in a protoplast system.

Example 12: Further CRISPR Nucleases

As detailed above, the hybrid nucleic acid sequences according to the present invention are suitable for a variety of CRISPR nucleases of different CRISPR systems. For any effector nuclease, e.g. Cas9, Cpf1, CasX or CasY, the optimal conditions and lengths of the gRNA and the RT will have to be evaluated as detailed in Examples 1 to 11 above to achieve optimum results for a genome editing event of interest for each cell type of interest. Furthermore, first experiments with CRISPR nickases were conducted the same way as detailed above using more than one gRNA and either one or two individual RTs associated with at least one of the gRNAs. First results demonstrate that this seems to be a promising approach for precison genome editing in eukaryotic cells as well.

Example 13: Animal-Cell Constructs

The invented method can be used in eukaryotic cells provided they are capable of homologous recombination. Murine T cells or T cell precursors can be modified in vitro to modulate them to be suitable for cancer immunotherapy. It could be demonstrated that the hybrid nucleic acid constructs according to the present invention, when specifically optimized (codon optimization) and designed (PAMs, target sites) for an animal system can be used for high precision genome editing in a eukaryotic animal cell type of interest. The modification of an expressed gene regulating the proliferation or function of the T cell using the method described in this invention can thus be used for therapy, particularly in a mammal, and more particularly to treat a disease or disorder in a subject by modification of a cell type of interest with the constructs according to the present invention Example 14: Transformation/Transfection of Exposed Immature Tassel Tissue As detailed above, a variety of physical/mechanical as well as biological means for transforming plant cells, tissues, organs or whole plants or parts thereof have been described for introducing genetic material into a plant or plant target structure. These methods are likewise suitable to introduce the at least one hybrid RNA/DNA nucleic acid sequence and/or at least one gRNA, and/or at least one repair template, and/or at least one CRISPR polypeptide according to the present invention. After having exposed and thus obtained a meristematic cell, for example a tassel tissue from a male maize plant, the following methods can be applied to transform this tissue:

Concerning biological means, plant tissues or cells thereof can be transformed with *Agrobacterium*, including *Agrobacterium tumefaciens* or *Agrobacterium rhizogenes* mediated transformation. This kind of transformation is well known to the person having skill in the art (see e.g. Jones, H. D. et al., "Review of methodologies and a protocol for the *Agrobacterium*-mediated transformation of wheat", plant methods, 2005; or Frame, B. R. et al., "*Agrobacterium tumefaciens*-mediated transformation of maize embryos using a standard binary vector system", Plant, 2002). To this end, an *Agrobacterium* culture comprising a construct of interest is, for example, cultivated over night at 28° C. in fluid Luria Broth medium containing a suitable antibiotic, 10 mM MES and 200 mM ACE. The next day, the over night cultured is centrifuged at 4,400 rpm for 15 min and the supernatant is discarded. The pellet is then again centrifuged for 15 min at 4,400 rpm for 2 min and the remaining supernatant is discarded. The pellet is resuspended (5 ml H2O, 10 mM MES, 10 mM $MgCl_2$+20 µM ACE). The optical density at 600 nm is adjusted to 1.5. The possibly diluted suspension can then be further used.

Another possibility for transforming meristematic cells or tissues of a plant via biological means is the use of viral vectors. Viral vectors have the advantage that they can be introduced either as DNA or as RNA and to a plant target structure of interest. Furthermore, viral vectors or plant viruses have the capability of spreading into different cells and tissues.

For the purpose of the present invention, virus particles, in vitro transcripts of viruses or Agrobacteria carrying a virus encoding T-DNA can be introduced into a plant target structure of interest via filtration (vacuum and non-vacuum). Alternative experiments can be carried out using plant sap. To this end, either tobacco or spinach can be infected with the virus of interest to subsequently isolate said virus of interest from the plant sap for infecting another plant target structure, especially meristematic cells or tissues from different plants with the plant sap containing the virus.

Despite the biological means of transforming tassel structures of interest, further physical/mechanical means for transformation in addition to particle bombardment can be used.

One suitable method is microinjection. Microinjection can be used for any kind of meristematic structure tested, preferentially using a microscope with a micromanipulator. Due to the size of certain meristematic structure like tassel or ear meristems microinjection can be conducted under microscope control or, in case where the target structures are large enough, without microscope assistance. The injection can be conducted, using a variety of methods for a variety of different target molecules to be introduced into a plant target structure of interest including double-stranded plasma DNA, linear double-stranded DNA, RNA and proteins as well as virus particles in liquid solution. These different molecules can be applied with the help of a micro- or nano-needles which assists in injecting the target molecules into the meristematic cell or structure of interest. The target molecules are first coated onto the needle which is then inserted into the meristematic cell or structure of interest.

Another suitable means is particle bombardment, e.g. using a particle delivery system, this method being further disclosed above.

A further development of this technology is the use of a combination of silicon carbide (SiC) whiskers (e.g. Silar®

Silicon Carbide Whisker) and microinjection. To this end, double-stranded (optionally plasmid) DNA, linear double-stranded DNA, RNA, protein, or a molecular ribonucleo-complex according to the present invention, or virus particles are precipitated onto the silicon carbide whisker to be injected via a microinjection needle into the meristematic structure or cell of interest. This technique has the advantage that it is not only possible to transfect a single cell, but there is the possibility to penetrate different cells in parallel due to the spread of the whiskers. Furthermore, the cells get less destructed, as the needle does not have to penetrate into the cell and the whiskers are quite small in size.

Example 15: Means for Detecting a Modification

Any transient or stable modification as introduced into at least one DNA target sequence according to the present invention can be detected using a fluorescence detection means, in case a fluorescent reporter is used. As tassel tissues like anthers and dry pollen have a strong autofluorescence, other means should be used for these cells and tissues. Detection can thus be accomplished and confirmed by further molecular methods, like PCR, including enrichment PCR, PCR-digest, a combination of enrichment PCR with PCR-digest, quantitative PCR, or sequencing, or RT-PCR, including deep or next generation sequencing or Southern or Northern blot analysis. Levels of protein can be analyzed by Western-Blotting and the like. In case, a phenotypically detectable trait was introduced into at least one cell of interest, it is also possible to perform an assay to detect whether said trait, for example, a resistance, a fluorescence, a morphological mutant phenotype, or any further trait, is present or absent in the at least one modified cell or a progeny or derivative thereof. The above detection methods are known to the skilled person.

As usual set up for analyzing a stable integration event in different target plants and cells thereof can be conducted as follows: First, DNA and/or RNA are extracted of different material, including, for example, tassel, anther or pollen tissue/cells transformed with different constructs encoding a fluorescent protein, e.g. a red fluorescent protein. In sum, samples can be analyzed via quantitative PCR (qPCR). From the above samples, several samples will show a clear, i.e. a very intense, (red) fluorescent signal, which is indicative of a positive event and which can then be selected. From those samples cDNA will be generated including controls without reverse transcriptase to exclude that the later results are not associated with undigested DNA. Out of the samples with positive DNA signal used for the transcription measurement, several samples could show a clear transcription and others a potential transcription (at the border of what could be clearly measured).

Example 16: Preparation of Suitable Hybrid RT/CRISPR Nucleic Acids

Figure 4:
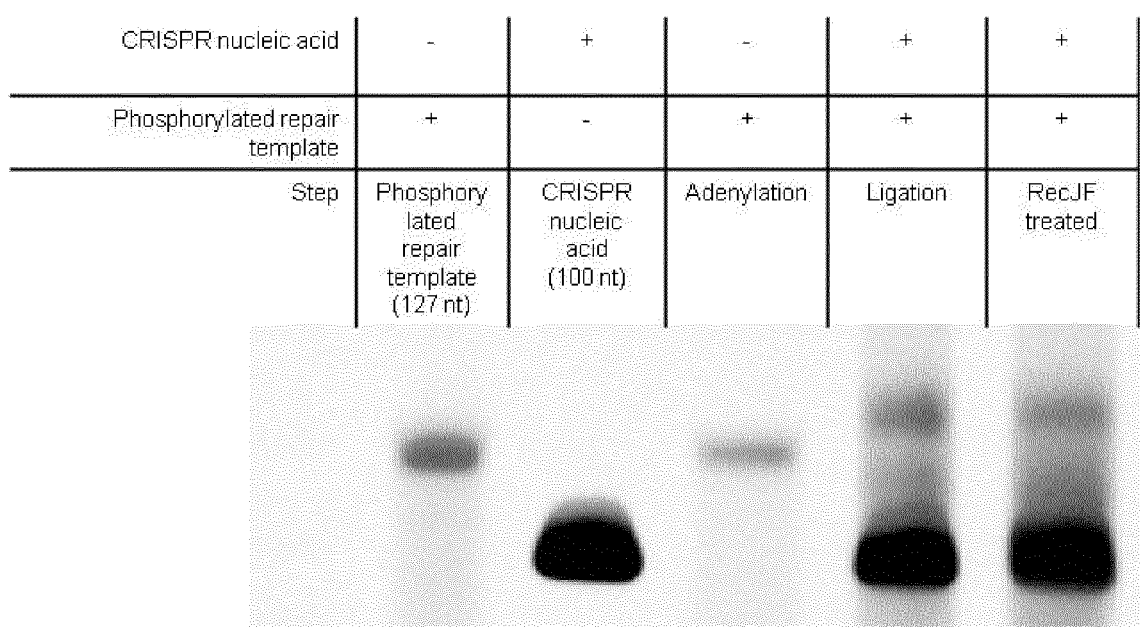
FIG. 4 (FIG. 4): shows the set-up (tabular survey on top) and the result (Tris-borate-EDTA (TBE) urea gel, 6% acrylamide, on the bottom) of an RNA-DNA ligation assay. To this end, 5' phosphorylated ssDNA as RT was purchased. This ssDNA was subsequently 5' adenylated and the resulting adenylated RT was subsequently ligated to the 3'end of a CRISPR nucleic acid of interest. RecJF, a single-stranded DNA specific 5'exonuclease, was used to test successful ligation of the adenylated RT ligated to the CRISPR nucleic acid. The educts and a mixture of each method step was applied to a TBE urea gel to monitor the educts and the respective products of each method step.

A variety of different hybrid nucleic acids was prepared in vitro and tested as illustrated in FIG. 4. First, a CRISPR RNA nucleic acid suitable for a Cas or Cpf nuclease of interest and a genomic target nucleic acid of interest was designed (100 nt in the Example shown in FIG. 4). A ssDNA as repair template was designed as RT to introduce a targeted HDR repair (127 nt in the Example shown in FIG. 4). For RNA-DNA ligation of different CRISPR nucleic acids and a RT of interest, respectively, a 5'adenylated RT was used. To this end, 5'phosphorylated ssDNA (or partially ssDNA, or dsDNA having a 5' phosphorylation) can be purchased or synthesized and, if not already phosphorylated, the ssDNA can be phosphorylated to provide a 5'phosphorylated RT. In one setting, a RT DNA stock (delivered as 4 nmol phosphorylated ultramer) was prepared to provide a 100 µM stock. Next, said RT was adenylated using 2 µl of a 3,000 ng/µl phosphorylated RT stock, 10× 5'DNA adenylation reaction buffer (2 µl), 1 mM ATP (4 µl), Mth RNA ligase (4 µl, 100 pmol), and 8 µl nuclease free water. The mixture was incubated for 1 h at 65° C. followed by inactivation of the enzyme (5 min, 85° C.). RNA-DNA ligation was then performed by using 2,250 ng (~7.5 µl of the adenylation reaction) of adenylated repair template, 1 µl RNase inhibitor, 750 ng of the RNA CRISPR nucleic acid, 50% PEG solution (5 µl, 10% final), 2.5 µl T4 RNA ligase reaction buffer, and 0.5 µl ligase. The mixture was incubated for 1 h at 25° C. followed by inactivation of the enzyme (20 min, 65° C.). Finally, a RecJF treatment was performed. RecJF is a single-stranded DNA specific 5' exonuclease, i.e., RecJF would degrade any not-ligated RT DNA. 15 µl of the RNA-DNA ligation product, 2 µl NEB buffer 2, 1.5 µl RecJF and 1.5 µl nuclease free water were incubated for 30 min at 37° followed by inactivation of the enzyme (20 min, 65° C.). The results of the reaction and the preceding steps was analyzed on a 6% acrylamide TBE urea gel using gel-red stain for visualization.

As evident from FIG. 4, aside from the obvious shift in size obtained from the ligation, the protection from RecJF treatment further shows that the 5'end of the RT is no longer accessible as the resulting ligated product was not degraded by RecJF. Therefore, any CRISPR nucleic acid of interest and a custom-made repair template of choice can be attached to each other covalently by the above method to provide a stable construct suitable for transfection for genome engineering. The linkage between CRISPR nucleic acid and RT will guarantee the physical availability of the construct after transfection into a cell of interest to provide maximum efficiency due to the high stability of the construct in comparison to those approaches providing CRISPR nucleic acid and RT separately.

The hybrid CRISPR nucleic acid/RT construct can then be associated with a CRISPR polypeptide of interest either in vitro or in vivo to build a stably associated nucleo-protein complex effecting a gene edit of interest, which can immediately be repaired by the presentation of the RT fused to the CRISPR nucleic acid at the site of a genomic DNA break induced by the CRISPR nuclease of choice.

To compare the efficiency of different topologies of CRISPR nucleic acids and RT in relation to each other within a hybrid nucleic acid, RTs of interest were designed and synthesized and various CRISPR nucleic acid sequences for different CRISPR nucleases of interest were designed in silico and then synthesized. The resulting RTs were optionally labeled with fluorescent dye at the 5'end. RTs and CRISPR nucleic acids were then chemically fused to each other, or hybridized to each other based on complementary stretches within RT and CRISPR nucleic acid sequences to provide 5'RT-CRISPR nucleic acid 3' constructs for further tests.

Example 17: Comparison of Gene Editing Efficiencies of Hybrid Nucleic Acids and Conventional RT/CRISPR Nucleic Acid Pairs In Vivo To compare the efficiency of introducing a targeted DNA break and repair using the hybrid nucleic acid sequences as detailed above and differences over conventional setting, where RT and CRISPR nucleic acids are provided separately and not associated with each other, the following example was set up.

In one example, the HDR efficiency of the hybrid repair template (RT)-CRISPR nucleic acid complex in different configurations (5'-CRISPR RNA-RT-3' or 3'-RT-CRISPR RNA-3', respectively) is compared to the HDR efficiency of the two components delivered individually. The complex is formed by ligation of the adenylated repair template and the CRISPR nucleic acid as detailed above in Example 16, or by chemically linking a CRISPR nucleic acid and a RT of choice to each other. Depending on the CRISPR nuclease of interest, the target genome of interest and the genomic target site of interest to be modified, any configuration for a hybrid nucleic acid sequence as detailed in FIG. 1a and FIG. 1b can be chosen. The complex between CRISPR nucleic acid and RT is then purified. Next, the purified complex is assembled with a CRISPR nuclease of interest and the resulting molecular complex is then transfected into a protoplast cell population by the PEG or an electroporation method. Alternatively, a cell population expressing a CRISPR nuclease of interest, either in a stable (constitutive or an inducible), or transient way, is chosen and the hybrid nucleic acid sequence complex formed ex vivo and is then transformed into a protoplast cell population, e.g., by the PEG method. In parallel, the same quantities of CRISPR nucleic acid and adenylated repair template are delivered without a ligation step into a protoplast cell population by the PEG or an electroporation method. Again, depending on the target protoplast, the CRISPR nucleic acid and the adenylated RT are either assembled ex vivo with a CRISPR nuclease of interest, or the individual CRISPR nucleic acid and the adenylated RT are transfected into a protoplast stably or transiently expressing a CRISPR nuclease of interest.

After 48 h, the two cell populations are harvested, their genomic DNA is extracted, and the target locus analyzed by molecular techniques such as (enrichment) PCR or amplicon deep sequencing. HDR efficiencies are compared as relative values. In case that the target gene of interest is a defective fluorescence encoding gene, e.g., the tdTomato gene (cf. Example 3 above), contained within the genome of the cell of interest, and the hybrid nucleic acid sequence and the CRISPR nuclease are configured to restore fluorescence of the respective fluorescence gene, the resulting cell populations can be analyzed by measuring fluorescence within the obtained cell populations as detailed above in Example 3.

The invention claimed is:

1. A method of modifying at least one DNA target sequence in a plant cell, the method comprising:
providing at least one plant cell comprising at least one DNA target sequence comprising at least one first and at least one second DNA target sequence in a genomic region of interest;
(ii) providing at least one synthetic molecular complex comprising at least one isolated hybrid nucleic acid sequence and at least one Cpf1 polypeptide, wherein the at least one isolated hybrid nucleic acid sequence and the at least one Cpf1 polypeptide are associated in a functional way after expression or synthesis;
(iii) contacting the at least one synthetic molecular complex with the at least one DNA target sequence under suitable conditions to achieve complementary base pairing of the first sequence portion of the Cpf1 nucleic acid sequence of the at least one isolated hybrid nucleic acid sequence with the at least one first DNA target sequence to achieve recognition of the first DNA target sequence by the at least one Cpf1 polypeptide and optionally induction of at least one DNA break by the at least one Cpf1 polypeptide, wherein at least one repair template nucleic acid sequence of the at least one isolated hybrid nucleic acid sequence directs homology directed repair at the site of the at least one second DNA target sequence; and
(iv) obtaining at least one plant cell comprising a modification in the at least one DNA target sequence,
wherein the Cpf1 nucleic acid sequence is an RNA sequence,
wherein the isolated hybrid nucleic acid comprises the at least one Cpf1 nucleic acid sequence and the at least one DNA nucleic acid sequence, wherein the DNA nucleic acid sequence is a repair template nucleic acid sequence,
(a) wherein the Cpf1 nucleic acid sequence comprises:
(i) a first sequence portion that is complementary to the first DNA target sequence, and
(ii) a second sequence portion, wherein the second sequence portion is configured to interact with the at least one Cpf1 polypeptide; and (b) wherein the repair template nucleic acid sequence comprises at least one portion complementary to the second DNA target sequence, and wherein the repair template nucleic acid sequence is configured to mediate targeted homology directed repair; and (c) optionally: a linker region between the Cpf1 nucleic acid sequence and the repair template nucleic acid sequence;

wherein the isolated hybrid nucleic acid sequence is capable of interacting with the at least one Cpf1 polypeptide so that the at least one Cpf1 polypeptide can recognize the first DNA target sequence and optionally induce a DNA break, and wherein the isolated hybrid nucleic acid sequence is configured to direct genome engineering through homology directed repair mediated by the repair template nucleic acid sequence at the site of the second DNA target sequence, wherein at least one repair template nucleic acid sequence is associated with the 5' end of the at least one Cpf1 nucleic acid sequence, and/or wherein the repair template nucleic acid sequence is located within the at least one Cpf1 nucleic acid sequence, and wherein the isolated hybrid nucleic acid sequence is in the form of a non-vector connected single-stranded or double-stranded nucleic acid.

2. The method according to claim 1, wherein the at least one isolated hybrid nucleic acid sequence of the synthetic molecular complex is provided to the at least one plant cell independently of the at least one Cpf1 polypeptide of the at least one molecular complex and wherein the at least one molecular complex is assembled within the at least one plant cell.

3. The method according to claim 1, wherein the modification of the at least one DNA target sequence is a genome editing approach causing a trait selected from the group consisting of yield improvement, tolerance to abiotic stress, including drought stress, osmotic stress, heat stress, cold stress, oxidative stress, heavy metal stress, salt stress or waterlogging, tolerance to biotic stress including tolerance to insects, tolerance to bacteria, tolerance to viruses, tolerance to fungi or tolerance to nematodes, resistance to herbicides, including glyphosate, glufosinate, ALS inhibitors, and Dicamba, lodging resistance, flowering time, shattering resistance, seed color, endosperm composition, nutritional content, or metabolic engineering, including genome editing to allow a molecular pharming approach in the at least one plant cell.

4. The method according to claim 1, further comprising the following step:

(v) identifying and/or selecting at least one plant cell comprising the modification in the at least one DNA target sequence.

5. A method for manufacturing a plant or plant cell comprising the following steps:

(i) performing a method according to claim 1;

(ii) obtaining at least one plant or a progeny thereof from the at least one plant cell from step (i);

(iii) optionally: determining the modification in the at least one DNA target sequence in the at least one cell of the at least one plant or a progeny thereof.

6. The method according to claim 5, wherein the at least one plant or plant cell is selected from a monocotyledonous or a dicotyledonous plant.

7. A method comprising use of at least one isolated hybrid nucleic acid sequence for genome editing in a plant cell, the at least one isolated hybrid nucleic acid sequence comprising at least one Cpf1 nucleic acid sequence and at least one DNA nucleic acid sequence, wherein the DNA nucleic acid sequence is a repair template nucleic acid sequence, (a) wherein the at least one Cpf1 nucleic acid sequence is an RNA sequence and comprises:

(iii) a first sequence portion that is complementary to a first DNA target sequence, and (iv) a second sequence portion, wherein the second sequence portion is configured to interact with a Cpf1 polypeptide; and (b) wherein the repair template nucleic acid sequence comprises at least one portion complementary to a second DNA target sequence, and wherein the repair template nucleic acid sequence is configured to mediate targeted homology directed repair; and (c) optionally: a linker region between the at least one Cpf1 nucleic acid sequence and the repair template nucleic acid sequence;

wherein the isolated hybrid nucleic acid sequence is capable of interacting with a Cpf1 polypeptide so that the Cpf1 polypeptide can recognize the first DNA target sequence and optionally induce a DNA break, and wherein the isolated hybrid nucleic acid sequence is configured to direct genome engineering through homology directed repair mediated by the repair template nucleic acid sequence at the site of the second DNA target sequence, wherein at least one repair template nucleic acid sequence is associated with the 5' end of the at least one Cpf1 nucleic acid sequence, and/or wherein the repair template nucleic acid sequence is located within the at least one Cpf1 nucleic acid sequence, and wherein the isolated hybrid nucleic acid sequence is in the form of a non-vector connected single-stranded or double-stranded nucleic acid.

8. A method comprising use of a synthetic molecular complex for genome editing in a plant cell, the synthetic molecular complex comprising at least one isolated hybrid nucleic acid sequence and at least one Cpf1 polypeptide, wherein the at least one isolated hybrid nucleic acid sequence and the at least one Cpf1 polypeptide are associated in a functional way, the at least one isolated hybrid nucleic acid sequence comprising at least one Cpf1 nucleic acid sequence and at least one DNA nucleic acid sequence, wherein the DNA nucleic acid sequence is a repair template nucleic acid sequence, (a) wherein the at least one Cpf1 nucleic acid sequence is an RNA sequence and comprises:

(iii) a first sequence portion that is complementary to a first DNA target sequence, and (iv) a second sequence portion, wherein the second sequence portion is configured to interact with the at least one Cpf1 polypeptide; and (b) wherein the repair template nucleic acid sequence comprises at least one portion complementary to a second DNA target sequence, and wherein the repair template nucleic acid sequence is configured to mediate targeted homology directed repair; and (c) optionally: a linker region between the at least one Cpf1 nucleic acid sequence and the repair template nucleic acid sequence;

wherein the isolated hybrid nucleic acid sequence is capable of interacting with the at least one Cpf1 polypeptide so that the at least one Cpf1 polypeptide can recognize the first DNA target sequence and optionally induce a DNA break, and wherein the isolated hybrid nucleic acid sequence is configured to direct genome engineering through homology directed repair mediated by the repair template nucleic acid sequence at the site of the second DNA target sequence, wherein at least one repair template nucleic acid sequence is associated with the 5' end of the at least one Cpf1 nucleic acid sequence, and/or wherein the repair template nucleic acid sequence is located within the at least one Cpf1 nucleic acid sequence, and wherein the isolated hybrid nucleic acid sequence is in the form of a non-vector connected single-stranded or double-stranded nucleic acid.

9. The method according to claim 1, wherein the at least one plant cell is selected from the group consisting of *Hordeum vulgare, Hordeum bulbusom, Sorghum bicolor, Saccharum officinarium, Zea mays, Setaria italica, Oryza minuta, Oryza sativa, Oryza australiensis, Oryza alta, Triticum aestivum, Triticum durum, Secale cereale*, Triticale, *Malus domestica, Brachypodium distachyon, Hordeum marinum, Aegilops tauschii, Daucus glochidiatus, Beta vulgaris, Daucus pusillus, Daucus muricatus, Daucus carota, Eucalyptus grandis, Nicotiana sylvestris, Nicotiana tomentosiformis, Nicotiana tabacum, Nicotiana benthamiana, Solanum lycopersicum, Solanum tuberosum, Coffea canephora, Vitis vinifera, Erythrante guttata*, Genlisea *aurea, Cucumis sativus, Morus notabilis, Arabidopsis arenosa, Arabidopsis lyrata, Arabidopsis thaliana, Crucihimalaya himalaica, Crucihimalaya wallichii, Cardamine flexuosa, Lepidium virginicum, Capsella* bursa *pastoris, Olmarabidopsis pumila, Arabis hirsute, Brassica napus, Brassica oleracea, Brassica rapa, Raphanus sativus, Brassica juncacea, Brassica nigra, Eruca vesicaria* subsp. *sativa, Citrus sinensis, Jatropha curcas, Populus trichocarpa, Medicago truncatula, Cicer yamashitae, Cicer bijugum, Cicer arietinum, Cicer reticulatum, Cicer* judaicum, *Cajanus cajanifolius, Cajanus scarabaeoides, Phaseolus vulgaris, Glycine max, Gossypium* sp., *Astragalus* sinicus, *Lotus japonicas, Torenia foumieri, Allium cepa, Allium fistulosum, Allium sativum, Helianthus annuus, Helianthus tuberosus* and *Allium tuberosum*, or any variety or subspecies belonging to one of the aforementioned plants.

10. The method of claim 5, wherein the at least one plant or plant cell is selected from the group consisting of *Zea* spp., *Nicotiana benthamiana*, Beta spp., *Secale* spp., and *Triticum* spp.

* * * * *

SEQUENCE LISTING

```
<160> NUMBER OF SEQ ID NOS: 18

<210> SEQ ID NO 1
<211> LENGTH: 7
<212> TYPE: PRT
<213> ORGANISM: Artificial Sequence
<220> FEATURE:
<223> OTHER INFORMATION: NLS of the SV40 virus large T-antigen

<400> SEQUENCE: 1

Pro Lys Lys Lys Arg Lys Val
1               5

<210> SEQ ID NO 2
<211> LENGTH: 16
<212> TYPE: PRT
<213> ORGANISM: Artificial Sequence
<220> FEATURE:
<223> OTHER INFORMATION: Nucleoplasmin bipartite NLS

<400> SEQUENCE: 2

Lys Arg Pro Ala Ala Thr Lys Lys Ala Gly Gln Ala Lys Lys Lys Lys
1               5                   10                  15

<210> SEQ ID NO 3
<211> LENGTH: 9
<212> TYPE: PRT
<213> ORGANISM: Artificial Sequence
<220> FEATURE:
<223> OTHER INFORMATION: c-myc NLS

<400> SEQUENCE: 3

Pro Ala Ala Lys Arg Val Lys Leu Asp
1               5

<210> SEQ ID NO 4
<211> LENGTH: 11
<212> TYPE: PRT
<213> ORGANISM: Artificial Sequence
<220> FEATURE:
<223> OTHER INFORMATION: c-myc NLS
```

```
<400> SEQUENCE: 4

Arg Gln Arg Arg Asn Glu Leu Lys Arg Ser Pro
1               5                   10

<210> SEQ ID NO 5
<211> LENGTH: 38
<212> TYPE: PRT
<213> ORGANISM: Artificial Sequence
<220> FEATURE:
<223> OTHER INFORMATION: hRNPA1 M9 NLS

<400> SEQUENCE: 5

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
            20                  25                  30

Arg Asn Gln Gly Gly Tyr
        35

<210> SEQ ID NO 6
<211> LENGTH: 42
<212> TYPE: PRT
<213> ORGANISM: Artificial Sequence
<220> FEATURE:
<223> OTHER INFORMATION: IBB domain from importin-alpha

<400> SEQUENCE: 6

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
        35                  40

<210> SEQ ID NO 7
<211> LENGTH: 8
<212> TYPE: PRT
<213> ORGANISM: Artificial Sequence
<220> FEATURE:
<223> OTHER INFORMATION: Sequence derived from myoma T protein

<400> SEQUENCE: 7

Val Ser Arg Lys Arg Pro Arg Pro
1               5

<210> SEQ ID NO 8
<211> LENGTH: 8
<212> TYPE: PRT
<213> ORGANISM: Artificial Sequence
<220> FEATURE:
<223> OTHER INFORMATION: Sequence derived from myoma T protein

<400> SEQUENCE: 8

Pro Pro Lys Lys Ala Arg Glu Asp
1               5

<210> SEQ ID NO 9
<211> LENGTH: 8
<212> TYPE: PRT
<213> ORGANISM: Artificial Sequence
<220> FEATURE:
<223> OTHER INFORMATION: Sequence derived from human p53
<220> FEATURE:
<221> NAME/KEY: misc_feature
<222> LOCATION: (2)..(2)
```

```
<223> OTHER INFORMATION: Xaa can be any naturally occurring amino acid

<400> SEQUENCE: 9

Pro Xaa Pro Lys Lys Lys Pro Leu
1               5

<210> SEQ ID NO 10
<211> LENGTH: 12
<212> TYPE: PRT
<213> ORGANISM: Artificial Sequence
<220> FEATURE:
<223> OTHER INFORMATION: Sequence derived from mouse c-abl IV

<400> SEQUENCE: 10

Ser Ala Leu Ile Lys Lys Lys Lys Lys Met Ala Pro
1               5                   10

<210> SEQ ID NO 11
<211> LENGTH: 5
<212> TYPE: PRT
<213> ORGANISM: Artificial Sequence
<220> FEATURE:
<223> OTHER INFORMATION: Sequence derived from influenza virus NS1

<400> SEQUENCE: 11

Asp Arg Leu Arg Arg
1               5

<210> SEQ ID NO 12
<211> LENGTH: 7
<212> TYPE: PRT
<213> ORGANISM: Artificial Sequence
<220> FEATURE:
<223> OTHER INFORMATION: Sequence derived from influenza virus NS1

<400> SEQUENCE: 12

Pro Lys Gln Lys Lys Arg Lys
1               5

<210> SEQ ID NO 13
<211> LENGTH: 10
<212> TYPE: PRT
<213> ORGANISM: Artificial Sequence
<220> FEATURE:
<223> OTHER INFORMATION: Sequence derived from Hepatitis virus delta
      antigen

<400> SEQUENCE: 13

Arg Lys Leu Lys Lys Lys Ile Lys Lys Leu
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Sequence derived from mouse Mx1 protein

<400> SEQUENCE: 14

Arg Glu Lys Lys Lys Phe Leu Lys Arg Arg
1               5                   10

<210> SEQ ID NO 15
<211> LENGTH: 20
<212> TYPE: PRT
<213> ORGANISM: Artificial Sequence
<220> FEATURE:
```

```
<223> OTHER INFORMATION: Sequence derived from human poly(ADP-ribose)
      polymerase

<400> SEQUENCE: 15

Lys Arg Lys Gly Asp Glu Val Asp Gly Val Asp Glu Val Ala Lys Lys
1               5                   10                  15

Lys Ser Lys Lys
            20

<210> SEQ ID NO 16
<211> LENGTH: 17
<212> TYPE: PRT
<213> ORGANISM: Artificial Sequence
<220> FEATURE:
<223> OTHER INFORMATION: Sequence derived from steroid hormone receptors
      (human) glucocorticoid

<400> SEQUENCE: 16

Arg Lys Cys Leu Gln Ala Gly Met Asn Leu Glu Ala Arg Lys Thr Lys
1               5                   10                  15

Lys

<210> SEQ ID NO 17
<211> LENGTH: 11
<212> TYPE: PRT
<213> ORGANISM: Artificial Sequence
<220> FEATURE:
<223> OTHER INFORMATION: Sequence derived from HIV Tat

<400> SEQUENCE: 17

Tyr Gly Arg Lys Lys Arg Arg Gln Arg Arg Arg
1               5                   10

<210> SEQ ID NO 18
<211> LENGTH: 5
<212> TYPE: PRT
<213> ORGANISM: Artificial Sequence
<220> FEATURE:
<223> OTHER INFORMATION: Sequence derived from HIV Tat

<400> SEQUENCE: 18

Gly Arg Lys Lys Arg
1               5
```